US011453864B2

(12) United States Patent
Sontheimer et al.

(10) Patent No.: US 11,453,864 B2
(45) Date of Patent: Sep. 27, 2022

(54) DNASE H ACTIVITY OF NEISSERIA MENINGITIDIS CAS9

(71) Applicant: UNIVERSITY OF MASSACHUSETTS, Boston, MA (US)

(72) Inventors: Erik J. Sontheimer, Auburndale, MA (US); Yan Zhang, Shrewsbury, MA (US)

(73) Assignee: UNIVERSITY OF MASSACHUSETTS, Boston, MA (US)

( * ) Notice: Subject to any disclaimer, the term of this patent is extended or adjusted under 35 U.S.C. 154(b) by 554 days.

(21) Appl. No.: 15/758,394

(22) PCT Filed: Sep. 6, 2016

(86) PCT No.: PCT/US2016/050396
§ 371 (c)(1),
(2) Date: Mar. 8, 2018

(87) PCT Pub. No.: WO2017/044419
PCT Pub. Date: Mar. 16, 2017

(65) Prior Publication Data
US 2018/0355331 A1   Dec. 13, 2018

Related U.S. Application Data

(60) Provisional application No. 62/215,424, filed on Sep. 8, 2015.

(51) Int. Cl.
*C12N 9/22* (2006.01)
*C12N 15/11* (2006.01)
*A61K 38/00* (2006.01)

(52) U.S. Cl.
CPC .............. *C12N 9/22* (2013.01); *C12N 15/11* (2013.01); *A61K 38/00* (2013.01); *C12N 2310/20* (2017.05)

(58) Field of Classification Search
None
See application file for complete search history.

(56) References Cited

U.S. PATENT DOCUMENTS

| 3,817,837 | A | 6/1974 | Rubenstein et al. ............ 435/7.9 |
| 3,850,752 | A | 11/1974 | Schuurs et al. ............... 435/7.93 |
| 3,939,350 | A | 2/1976 | Kronick et al. ............... 250/365 |
| 3,996,345 | A | 12/1976 | Ullman et al. ................ 436/537 |
| 4,275,149 | A | 6/1981 | Litman et al. ................ 435/7.91 |
| 4,277,437 | A | 7/1981 | Maggio ......................... 422/401 |
| 4,366,241 | A | 12/1982 | Tom et al. .................... 435/7.91 |
| 5,705,188 | A | 1/1998 | Junichi et al. ................. 424/450 |
| 2014/0349405 | A1* | 11/2014 | Sontheimer ............ C07K 14/22 435/462 |

FOREIGN PATENT DOCUMENTS

| WO | WO/2013/142578 | 9/1913 |
| WO | WO/2015/089277 | 6/1915 |
| WO | WO/1997/030731 | 8/1997 |

OTHER PUBLICATIONS

Cong et al. (Multiplex genome engineering using CRISPR/Cas systems. Science 339, 819-823, 2013).*
Cho et al. (Targeted genome engineering in human cells with the Cas9 RNA-guided endonuclease. Nature Biotechnology 31, 230-232, 2013).*
Lee et al. (Development of neisseria meningitidis CRISPR/Cas9 systems for efficient and specific genome editing, Molecular Therapy, (May 2015) vol. 23, Supp. SUPPL. 1, pp. S132-S133. Abstract No. 331.).*
Anders, C. et al. (2014) "Structural basis of PAM-dependent target DNA recognition by the Cas9 endonuclease," *Nature* 513(7519), 569-573.
Anderson, M. L. M. et al. (1985) "Quantitative Filter Hybridization," in *Nucleic Acid Hybridisation: A Practical Approach* (Hames, B. D., et al., Eds.), pp. 73-111, Oxford University Press, USA.
Barrangou, R. et al. (2007) "CRISPR Provides Acquired Resistance Against Viruses in Prokaryotes," *Science* 315(5819), 1709.
Barrangou, R. et al. (2014) "CRISPR-Cas systems: Prokaryotes upgrade to adaptive immunity," *Molecular Cell* 54(2), 234-244.

(Continued)

*Primary Examiner* — Suzanne M Noakes
*Assistant Examiner* — Jae W Lee
(74) *Attorney, Agent, or Firm* — Medlen & Carroll, LLP

(57) ABSTRACT

Many strains of the human pathogen *Neisseria meningitidis* carry a compact Cas9 (NmeCas9) that can serve to limit genetic exchange via natural transformation. Cas9 orthologues (including NmeCas9) have recently been adopted for RNA-guided genome engineering and DNA binding, adding to the need to define better their activities and properties. The present invention examines DNA cleavage activities and substrate requirements of NmeCas9, including a set of unusually complex PAM recognition patterns. Unexpectedly, NmeCas9 is found able to cleave single-stranded DNA (ssDNA) targets in a manner that is RNA-guided but both PAM- and tracrRNA-independent. Beyond the requirement for guide-target pairing, this activity has no apparent sequence requirements, and the cleavage sites are measured from the 5' end of the DNA substrate's RNA-paired region. These results indicate that tracrRNA domains are not strictly required for enzymatic activation of NmeCas9, and expand the list of targeting activities exhibited by these revolutionary RNA-guided nucleases.

15 Claims, 28 Drawing Sheets

Specification includes a Sequence Listing.

(56) References Cited

OTHER PUBLICATIONS

Bernick, D. L. et al. (2012) "Comparative genomic and transcriptional analyses of CRISPR systems across the genus *Pyrobaculum*," *Frontiers in Microbiology 3*, 251.
Bhaya, D. et al. (2011) "CRISPR-Cas Systems in Bacteria and Archaea: Versatile Small RNAs for Adaptive Defense and Regulation," *Annual Reviev of Genetics 45*(1), 273-297.
Bikard, D. et al. (2012) "CRISPR Interference Can Prevent Natural Transformation and Virulence Acquisition during In Vivo Bacterial Infection," *Cell Host & Microbe 12*(2), 177-186.
Bikard, D. et al. (2013) "Programmable repression and activation of bacterial gene expression using an engineered CRISPR-Cas system," *Nucleic Acids Research 41*(15), 7429-7437.
Bolotin, A. et al. (2005) "Clustered regularly interspaced short palindrome repeats (CRISPRs) have spacers of extrachromosomal origin," *Microbiology 151*(8), 2551-2561.
Briner, Alexandra E. et al. (2014) "Guide RNA Functional Modules Direct Cas9 Activity and Orthogonality," *Molecular Cell 56*(2), 333-339.
Brouns, S. J. J. et al. (2008) "Small CRISPR RNAs Guide Antiviral Defense in Prokaryotes," *Science 321*(5891), 960-964.
Charpentier, E., et al. (2013) "Biotechnology: Rewriting a genome," *Nature 495*(7439), 50-51.
Chen, H. et al. (2014) "Cut Site Selection by the Two Nuclease Domains of the Cas9 RNA-guided Endonuclease," *Journal of Biological Chemistry 289*(19), 13284-13294.
Cho, S. W. et al. (2013) "Targeted genome engineering in human cells with the Cas9 RNA-guided endonuclease," *Nature Biotechnology 31*(3), 230-232.
Cong, L. et al. (2013) "Multiplex Genome Engineering Using CRISPR/Cas Systems," *Science (New York, N.Y.) 339*(6121), 819-823.
Deltcheva, E. et al. (2011) "CRISPR RNA maturation by trans-encoded small RNA and host factor RNase III," *Nature 477*(7340), 602-607.
Deveau, H. et al. (2008) "Phage Response to CRISPR-Encoded Resistance in *Streptococcus thermophilus,*" *Journal of Bacteriology 190*(4), 1390-1400.
Dienstag, J. L. (2008) "Hepatitis B Virus Infection," *New England Journal of Medicine 359*(14), 1486-1500.
Doudna, J. A. et al. (2014) "Genome editing. The new frontier of genome engineering with CRISPR-Cas9," *Science 346*(6213), 1258096.
Esvelt, K. M. et al. (2013) "Orthogonal Cas9 Proteins for RNA-Guided Gene Regulation and Editing," *Nature Methods 10*(11), 10.1038/nmeth.2681.
Fonfara, I. et al. (2014) "Phylogeny of Cas9 determines functional exchangeability of dual-RNA and Cas9 among orthologous type II CRISPR-Cas systems," *Nucleic Acids Research 42*(4), 2577-2590.
Garneau, J. E. et al. (2010) "The CRISPR/Cas bacterial immune system cleaves bacteriophage and plasmid DNA," *Nature 468*, 67.
Gasiunas, G. et al. (2012) "Cas9-crRNA ribonucleoprotein complex mediates specific DNA cleavage for adaptive immunity in bacteria," *Proceedings of the National Academy of Sciences of the United States of America 109*(39), E2579-E2586.
Gilbert, L. A. et al. (2013) "CRISPR-mediated modular RNA-guided regulation of transcription in eukaryotes," *Cell 154*(2), 442-451.
Gunderson, F. F. et al. (2013) "The CRISPR-Associated Gene cas2 of Legionella pneumophila Is Required for Intracellular Infection of Amoebae," *mBio 4*(2), e00074-00013.
Hale, C. et al. (2008) "Prokaryotic silencing (psi)RNAs in Pyrococcus furiosus," *RNA 14*(12), 2572-2579.
Hou, Z. et al. (2013) "Efficient genome engineering in human pluripotent stem cells using Cas9 from Neisseria meningitidis," *Proceedings of the National Academy of Sciences 110*(39), 15644-15649.
Hsu, P. D. et al. (2014) "Development and applications of CRISPR-Cas9 for genome engineering," *Cell 157*(6), 1262-1278.
Hsu, P. D. et al. (2013) "DNA targeting specificity of RNA-guided Cas9 nucleases," *Nature Biotechnology 31*(9), 827-832.
Hwang, W. Y. et al. (2013) "Efficient In Vivo Genome Editing Using RNA-Guided Nucleases," *Nature Biotechnology 31*(3), 227-229.
Jiang, F. et al. (2015) "Structural Biology. A Cas9-guide RNA complex preorganized for target DNA recognition," *Science 348*(6242), 1477-1481.
Jiang, W. et al. (2013) "CRISPR-assisted editing of bacterial genomes," *Nature Biotechnology 31*(3), 233-239.
Jinek, M. et al. (2012) "A programmable dual-RNA-guided DNA endonuclease in adaptive bacterial immunity," *Science 337*(6096), 816-821.
Jinek, M. et al. (2013) "RNA-programmed genome editing in human cells," *eLife 2*, e00471.
Jinek, M. et al. (2014) "Structures of Cas9 Endonucleases Reveal RNA-Mediated Conformational Activation," *Science 343*(6176).
Johnston, C. et al. (2014) "Bacterial transformation: distribution, shared mechanisms and divergent control," *Nature Reviews Microbiology 12*, 181.
Kawai, M. et al. (2005) "Genome Comparison In Silico in Neisseria Suggests Integration of Filamentous Bacteriophages by their Own Transposase," *DNA Research 12*(6), 389-401.
Kearns, N. A. et al. (2015) "Functional annotation of native enhancers with a Cas9-histone demethylase fusion," *Nature Methods 12*(5), 401-403.
Konermann, S. et al. (2013) "Optical control of mammalian endogenous transcription and epigenetic states," *Nature 500*(7463), 472-476.
Larson, M. H. et al. (2013) "CRISPR interference (CRISPRi) for sequence-specific control of gene expression," *Nature Protocols 8*(11), 2180-2196.
Louwen, R. et al. (2013) "A novel link between Campylobacter jejuni bacteriophage defence, virulence and Guillain-Barre syndrome," *European Journal of Clinical Microbiology and Infectious Diseases 32*(2), 207-226.
Maeder, M. L. et al. (2013) "CRISPR RNA-guided activation of endogenous human genes," *Nature Methods 10*(10), 977-979.
Makarova, K. S. et al. (2015) "An updated evolutionary classification of CRISPR-Cas systems," *Nature Reviews. Microbiology 73*(11), 722-736.
Mali, P. et al. (2013) "RNA-guided human genome engineering via Cas9," *Science 339*(6121), 823-826.
Marraffini, L. A. et al. (2008) "CRISPR Interference Limits Horizontal Gene Transfer in Staphylococci by Targeting DNA," *Science (New York, N.Y.) 322*(5909), 1843-1845.
Mojica, F. J. et al. (2005) "Intervening sequences of regularly spaced prokaryotic repeats derive from foreign genetic elements," *Journal of Molecular Evolution 60*(2), 174-182.
Mojica, F. J. M. et al. (2009) "Short motif sequences determine the targets of the prokaryotic CRISPR defence system," *Microbiology 155*(3), 733-740.
Nishimasu, H. et al. (2014) "Crystal Structure of Cas9 in Complex with Guide RNA and Target DNA," *Cell 156*(5), 935-949.
Nuñez, J. K. et al. (2014) "Cas1-Cas2 complex formation mediates spacer acquisition during CRISPR-Cas adaptive immunity," *Nature Structural & Molecular Biology 21*(6), 528-534.
Nuñez, J. K. et al. (2015) "Integrase-mediated spacer acquisition during CRISPR-Cas adaptive immunity," *Nature 519*, 193.
Pattanayak, V. et al. (2013) "High-throughput profiling of off-target DNA cleavage reveals RNA-programmed Cas9 nuclease specificity," *Nature Biotechnology 31*(9), 839-843.
Perez-Pinera, P. et al. (2013) "RNA-guided gene activation by CRISPR-Cas9-based transcription factors," *Nature Methods 10*(10), 973-976.
Pourcel, C. et al. (2005) "CRISPR elements in Yersinia pestis acquire new repeats by preferential uptake of bacteriophage DNA, and provide additional tools for evolutionary studies," *Microbiology 151*(3), 653-663.
Qi, L. S. et al. (2013) "Repurposing CRISPR as an RNA-Guided Platform for Sequence-Specific Control of Gene Expression," *Cell 152*(5), 1173-1183.
Ran, F. A. et al. (2015) "In vivo genome editing using *Staphylococcus aureus* Cas9," *Nature 520*(7546), 186-191.

(56) References Cited

OTHER PUBLICATIONS

Ran, F. A. et al. (2013) "Double Nicking by RNA-Guided CRISPR Cas9 for Enhanced Genome Editing Specificity," *Cell 154*(6), 1380-1389.

Ren, X. et al. (2014) "Enhanced Specificity and Efficiency of the CRISPR/Cas9 System with Optimized sgRNA Parameters in *Drosophila*," *Cell Reports 9*(3), 1151-1162.

Rotman, E. et al. (2014) "The Genetics of *Neisseria* Species," *Annual Review of Genetics 48*(1), 405-431.

Sampson, T. R. et al. (2014) "A CRISPR-Cas system enhances envelope integrity mediating antibiotic resistance and inflammasome evasion," *Proceedings of the National Academy of Sciences 111*(30), 11163.

Sampson, T. R. et al. (2013) "A CRISPR/Cas system mediates bacterial innate immune evasion and virulence," *Nature 497*, 254.

Sapranauskas, R. et al. (2011) "The *Streptococcus thermophilus* CRISPR/Cas system provides immunity in *Escherichia coli*," *Nucleic Acids Research 39*(21), 9275-9282.

Sontheimer, E. J. et al. (2015) "The Bacterial Origins of the CRISPR Genome-Editing Revolution," *Human Gene Therapy 26*(7), 413-424.

Sorek, R. et al. (2013) "CRISPR-Mediated Adaptive Immune Systems in Bacteria and Archaea," *Annual Review of Biochemistry 82*(1), 237-266.

Sternberg, S. H. et al. (2014) "DNA interrogation by the CRISPR RNA-guided endonuclease Cas9," *Nature 507*(7490), 62-67.

Stols, L. et al. (2002) "A New Vector for High-Throughput, Ligation-Independent Cloning Encoding a Tobacco Etch Virus Protease Cleavage Site," *Protein Expression and Purification 25*(1), 8-15.

Takashi, T. et al. (2009) "RibonucleaseH: molecular diversities, substrate binding domains, and catalytic mechanism of the prokaryotic enzymes," *FEBS Journal 276*(6), 1482-1493.

Van Der Oost, J. et al. (2014) "Unravelling the structural and mechanistic basis of CRISPR-Cas systems," *Nature Reviews Microbiology 12*(7), 479-492.

Vercoe, R. B. et al. (2013) "Cytotoxic Chromosomal Targeting by CRISPR/Cas Systems Can Reshape Bacterial Genomes and Expel or Remodel Pathogenicity Islands," *PLoS Genetics 9*(4), e1003454.

Wiedenheft, B. et al. (2012) "RNA-guided genetic silencing systems in bacteria and archaea," *Nature 482*(7385), 331-338.

Yosef, I et al. (2012) "Proteins and DNA elements essential for the CRISPR adaptation process in *Escherichia coli*," *Nucleic Acids Research 40*(12), 5569-5576.

Zhang, Y. et al. (2014) "Comparison of non-canonical PAMs for CRISPR/Cas9-mediated DNA cleavage in human cells," *Scientific Reports 4*, 5405.

Zhang, Y. et al. (2013) "Processing-Independent CRISPR RNAs Limit Natural Transformation in Neisseria meningitidis," *Molecular Cell 50*(4), 488-503.

PCT International SearchReport of International Application No. PCT/US2016/050396 dated Feb. 8, 2017.

\* cited by examiner

Figure 1A
SEQ ID NO: 152
SEQ ID NO: 153
SEQ ID NO: 154
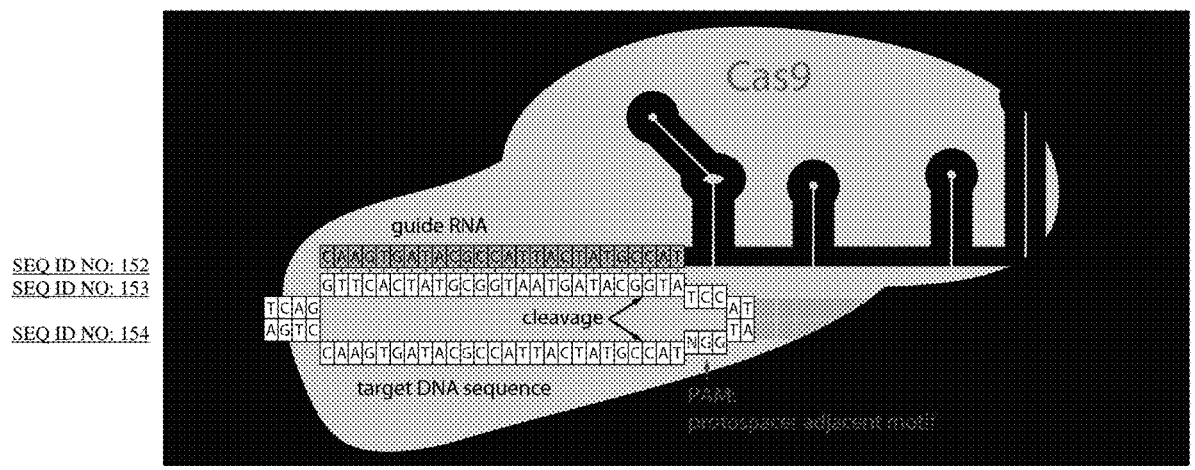
Figure 1B
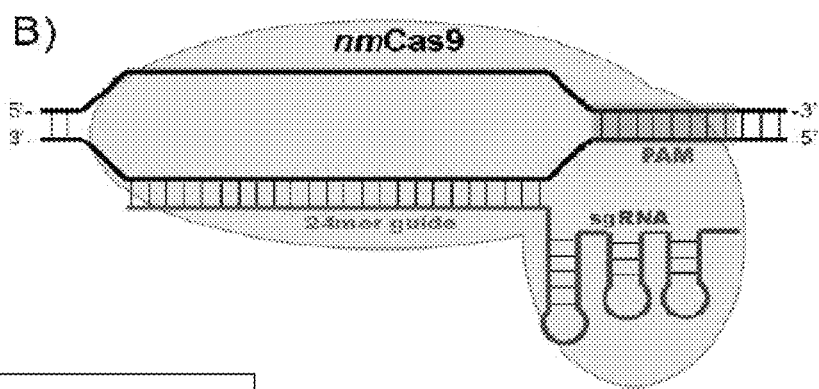
Figure 1A – 1B Figure 3A
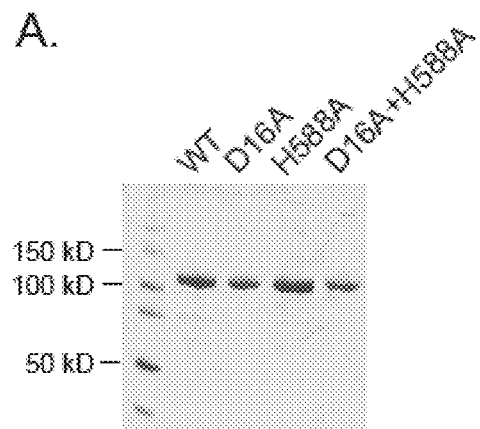
Figure 3B
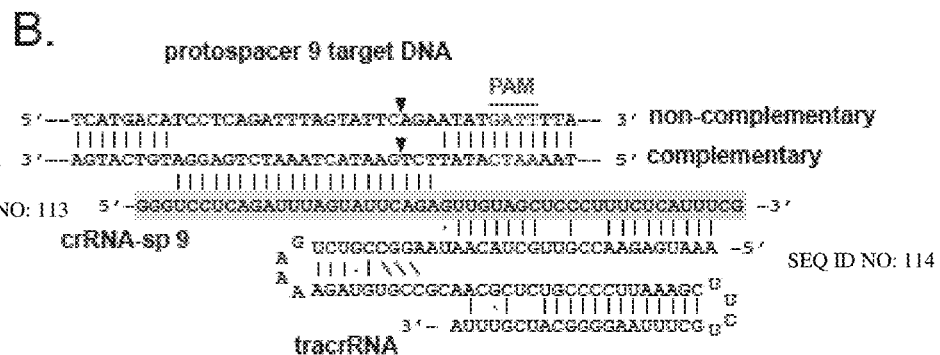
Figure 3A – 3B Figure 3C
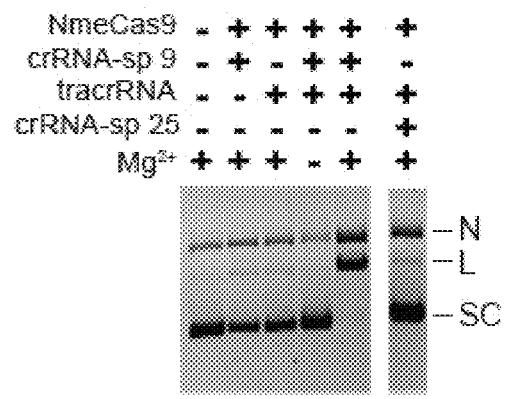
Figure 3D
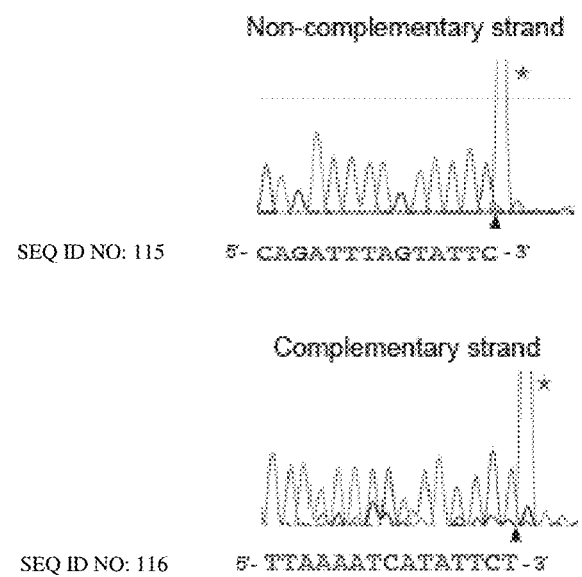
Figure 3C – 3D Figure 6A
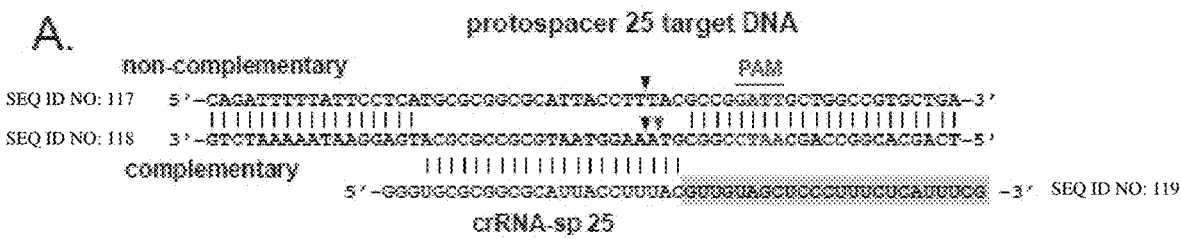
Figure 6B
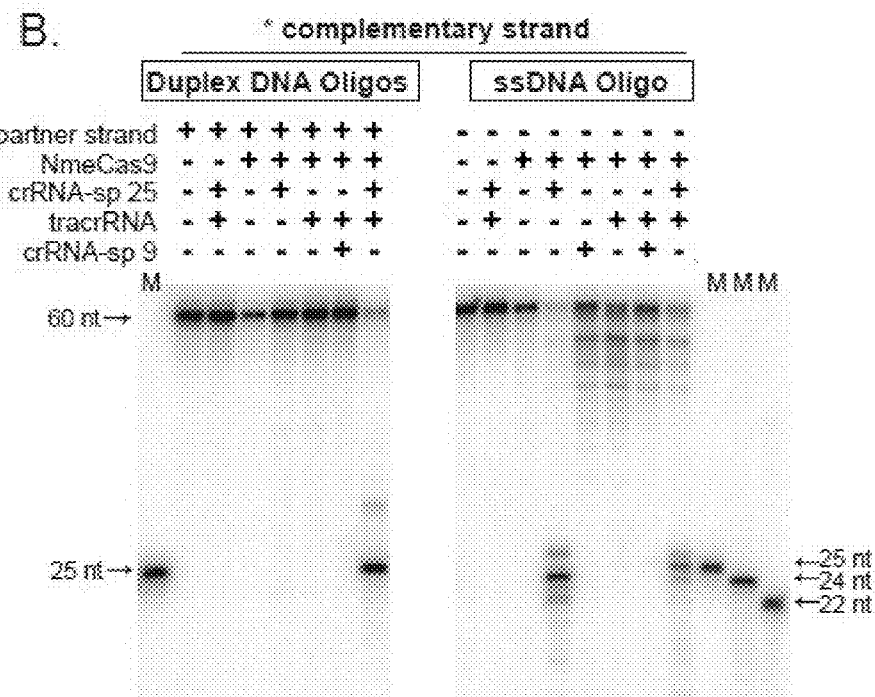
Figure 6A – 6B

Figure 6C
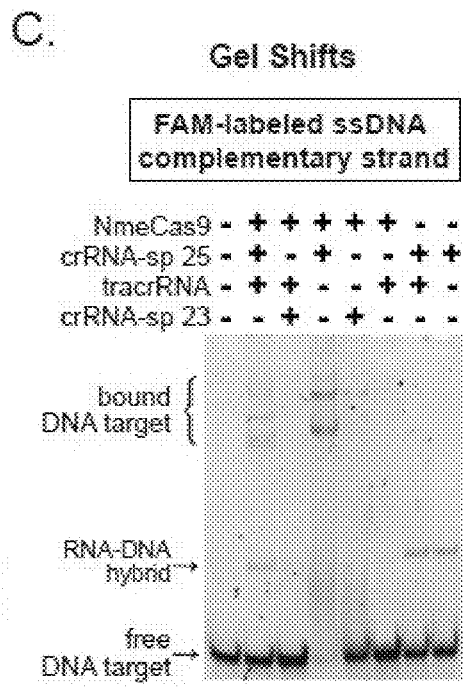
Figure 6D
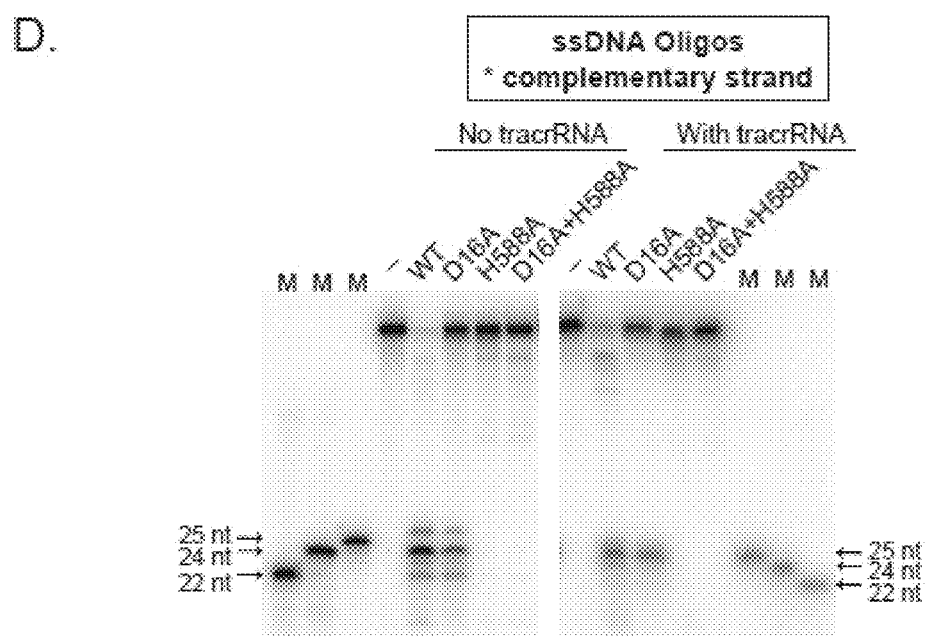
Figure 6C – 6D

FIG 8 A-B

Figure 10A
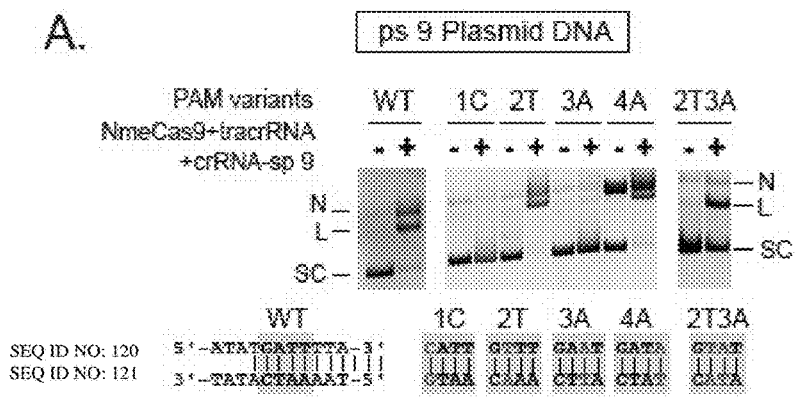
Figure 10B
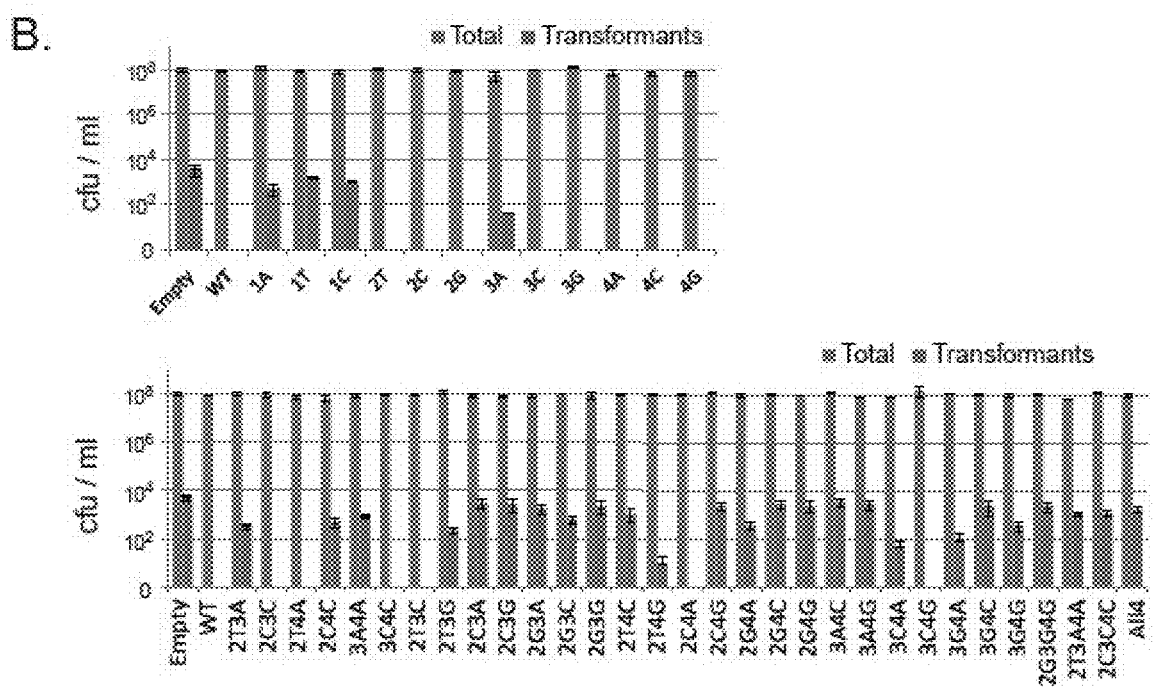
Figure 10A – 10B

Figure 10C
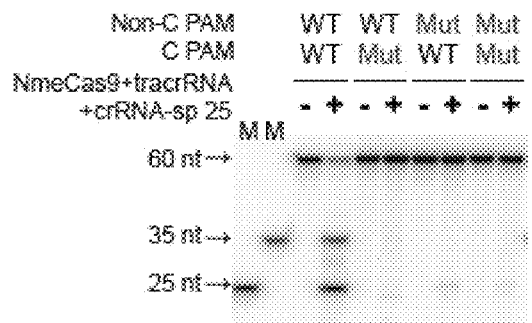
SEQ ID NO: 122
SEQ ID NO: 123
Figure 10D
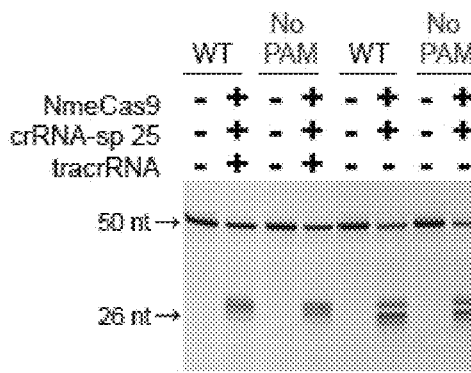
SEQ ID NO: 124        SEQ ID NO: 125
Figure 10C – 10D Figure 11A
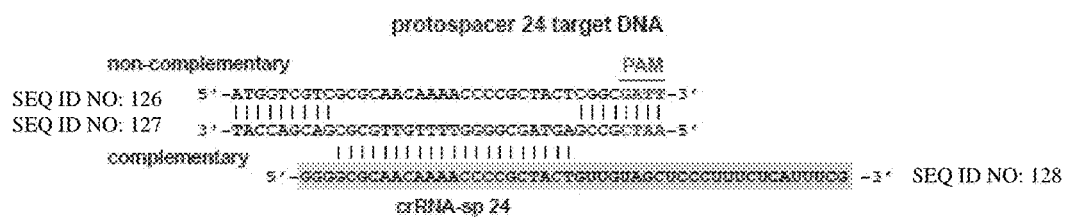
Figure 11B
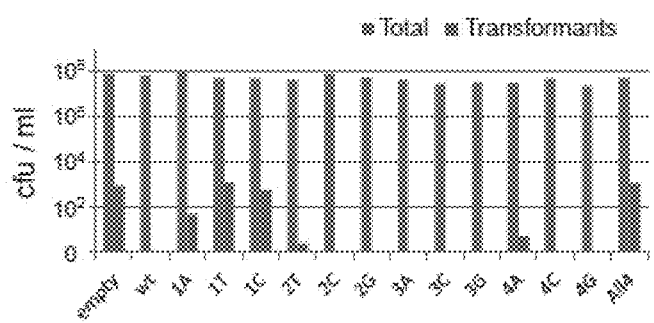
Figure 11A – 11B

Figure 13A
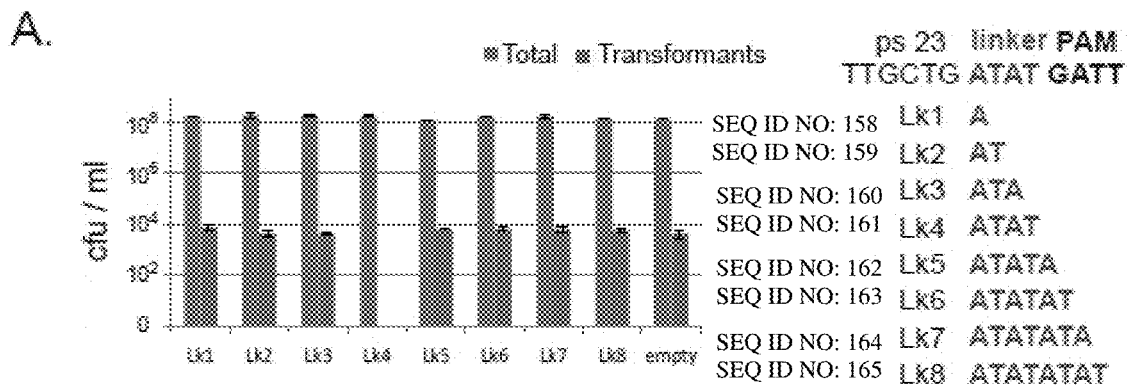
Figure 13B
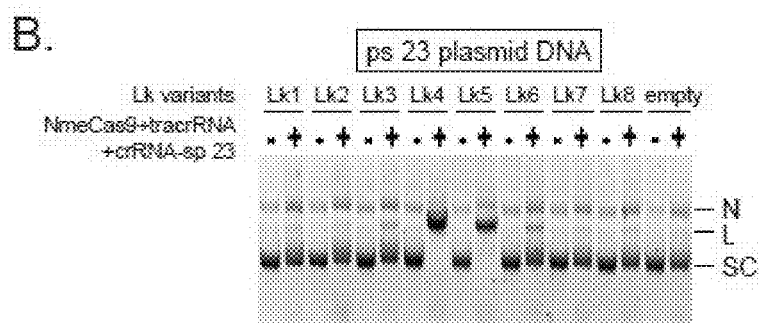
Figure 13A – 13B

Figure 13C
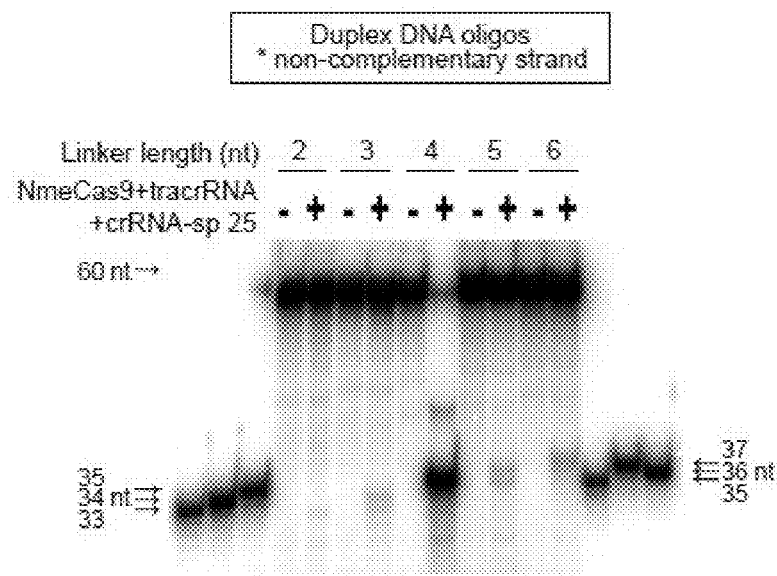
Figure 13D
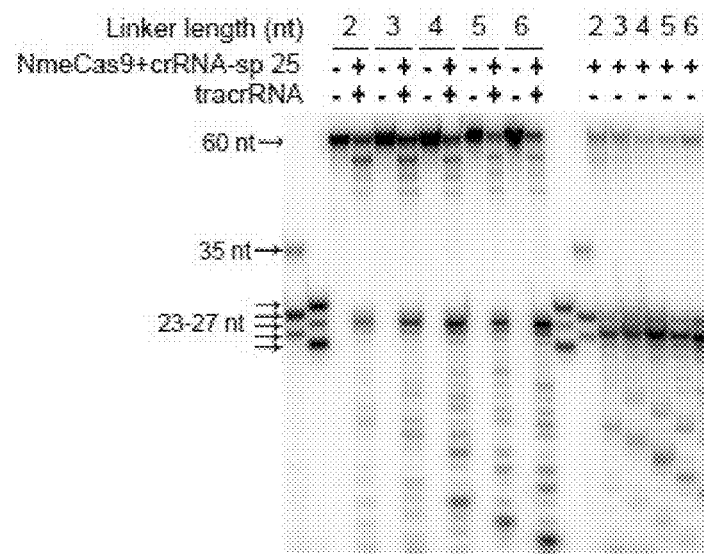
Figure 13C – 13D

Figure 14A
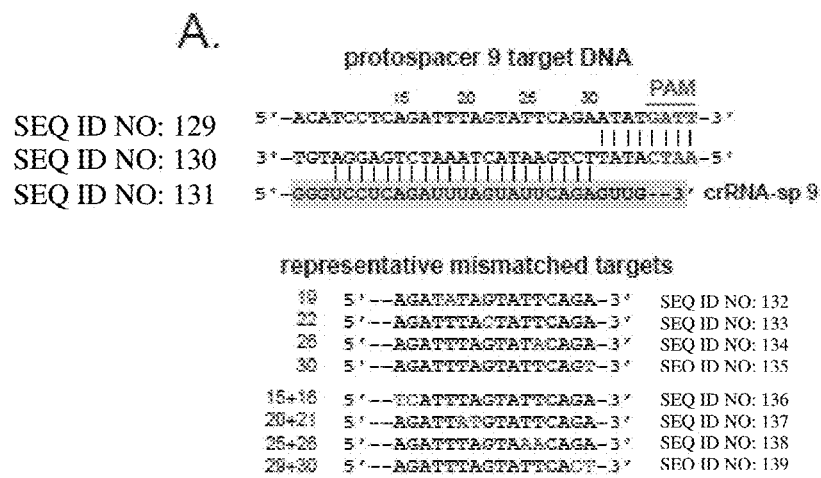
Figure 14B
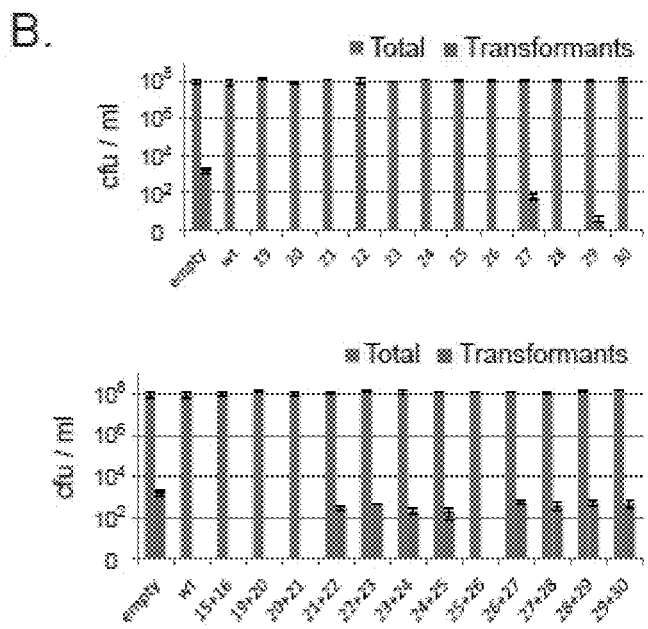
Figure 14A – 14B

Figure 15A
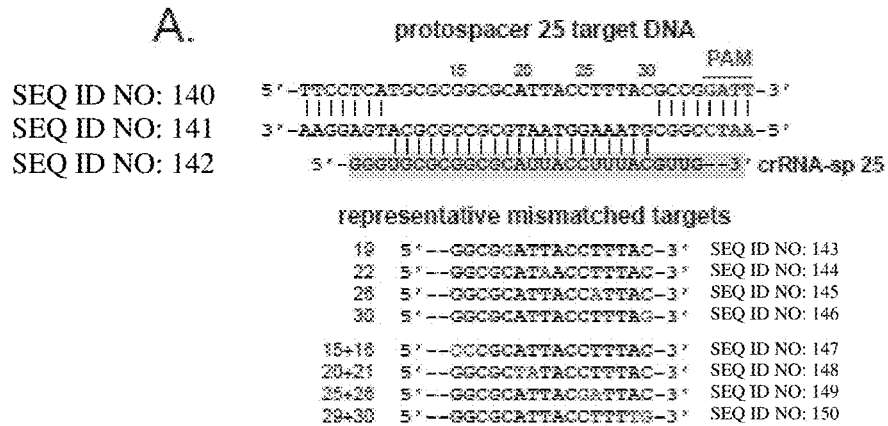
SEQ ID NO: 140
SEQ ID NO: 141
SEQ ID NO: 142
Figure 15B
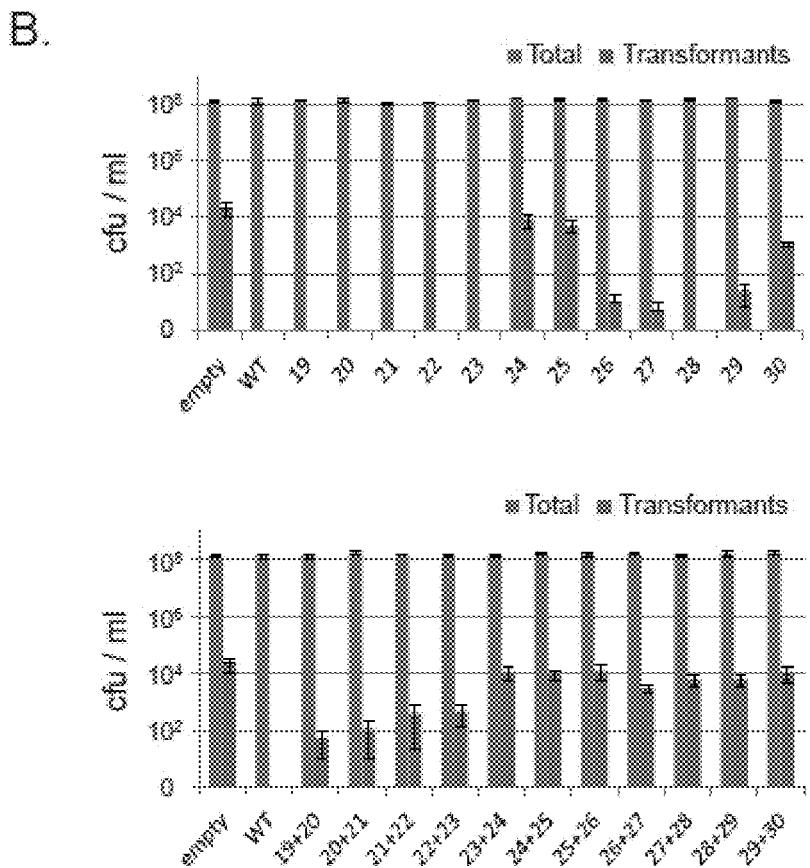
Figure 15A – 15B Figure 16A
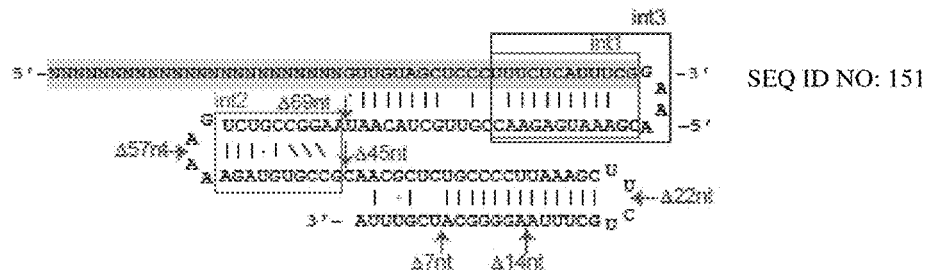 SEQ ID NO: 151
Figure 16B
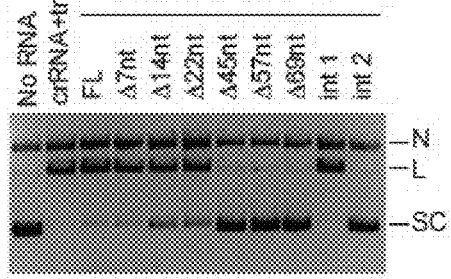
Figure 16C
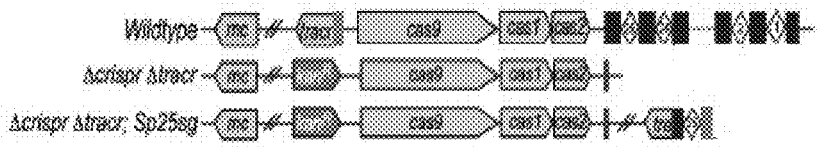
Figure 16A - 16C

Figure 17

| SEQ ID NOS: | Oligo Name | (*) | Sequence, 5'-3'(**) | Purpose |
|---|---|---|---|---|
| | **For generating *in vitro* transcription templates by annealing (T7 promoter in bold)** | | | |
| 21 | T7-tracrRNA Forw | F | TAATACGACTCACTATAGAAATGAGAACCGTTGCTAC AATAAGGCCGTCTGAAAAGATGTGCCGCAACGCTCTG CCCCTTAAAGCTTCTGCTTTAAGGGGCATCGTTTA | TracrRNA (Hou et al., 2013) |
| 22 | T7-tracrRNA AS | R | TAAACGATGCCCCTTAAAGCAGAAGCTTTAAGGGGCA GAGCGTTGCGGCACATCTTTTCAGACGGCCTTATTGT AGCAACGGTTCTCATTTCTATAGTGAGTCGTATTA | |
| 23 | T7-Sp25-R Forw | F | TAATACGACTCACTATAGGGTGCGCGGCGCATTACCT TTACGTTGTAGCTCCCTTTCTCATTTCG | CrRNA-sp25 |
| 24 | T7-Sp25-R AS | R | CGAAATGAGAAAGGGAGCTACAACGTAAAGGTAATGC GCCGCGCACCCTATAGTGAGTCGTATTA | |
| 25 | T7-Sp9-R Forw | F | TAATACGACTCACTATAGGGTCCTCAGATTTAGTATTC AGA GTTGTAGCTCCCTTTCTCATTTCG | CrRNA-sp9 |
| 26 | T7-Sp9-R AS | R | CGAAATGAGAAAGGGAGCTACAACTCTGAATACTAAAT CTGAGGACCCTATAGTGAGTCGTATTA | |
| 27 | T7-Sp23-R Forw | F | TAATACGACTCACTATAGGGTTTCATGGCGCGTTCTT GCTG GTTGTAGCTCCCTTTCTCATTTCG | CrRNA-sp23 |
| 28 | T7-Sp23-R AS | R | CGAAATGAGAAAGGGAGCTACAACCAGCAAGAACGC GCCATGAAACCCTATAGTGAGTCGTATTA | |
| 29 | T7-Sp25-12nt R Forw | F | TAATACGACTCACTATAGGGTGCGCGGCGCATTACCT TTACGTTGTAGCTCCC | CrRNA-sp25 12nt R |
| 30 | T7-Sp25-12nt R AS | R | GGGAGCTACAACGTAAAGGTAATGCGCCGCGCACCCTATAGTGAGTCGTATTA | |
| 31 | T7-Sp25-8nt R Forw | F | TAATACGACTCACTATAGGGTGCGCGGCGCATTACCT TTACGTTGTAGC | CrRNA-sp25 8nt R |
| 32 | T7-Sp25-8nt R AS | R | GCTACAACGTAAAGGTAATGCGCCGCGCACCCTATAG TGAGTCGTATTA | |
| 33 | T7-Sp25-4nt R Forw | F | TAATACGACTCACTATAGGGTGCGCGGCGCATTACCT TTACGTTG | CrRNA-sp25 4nt R |
| 34 | T7-Sp25-4nt R AS | R | CAACGTAAAGGTAATGCGCCGCGCACCCTATAGTGAG TCGTATTA | |
| 35 | T7-Sp25-0nt R Forw | F | TAATACGACTCACTATAGGGTGCGCGGCGCATTACCT TTAC | CrRNA-sp25 0nt R |
| 36 | T7-Sp25-0nt RAS | R | GTAAAGGTAATGCGCCGCGCACCCTATAGTGAGTCGT ATTA | |
| 37 | T7-Sp25-Sp.R Forw | F | TAATACGACTCACTATAGGGTGCGCGGCGCATTACCT TTACGTTTTAGAGCTATGCTGTTTTG | CrRNA-sp25 Sp.R |
| 38 | T7-Sp25-Sp.R AS | R | CAAAACAGCATAGCTCTAAAACGTAAAGGTAATGCGC CGCGCACCCTATAGTGAGTCGTATTA | |
| 39 | T7-Sp25-0nt R+3'Δ5nt F | F | TAATACGACTCACTATAGGGTGCGCGGCGCATTACC | CrRNA-sp25 0nt R+3'Δ5nt |
| 40 | T7-Sp25-0nt R+3'Δ5nt AS | R | GGTAATGCGCCGCGCACCCTATAGTGAGTCGTATTA | |
| 41 | T7-Sp25-0nt R+3'Δ5nt+5' 2nt extension F | F | TAATACGACTCACTATAGGGCATGCGCGGCGCATTAC C | CrRNA-sp25 0nt R+3'Δ5nt+5' 2nt extension |
| 42 | T7-Sp25-0nt R+3'Δ5nt+5' 2nt extension AS | R | GGTAATGCGCCGCGCATGCCCTATAGTGAGTCGTATT A | |
| 43 | T7-Sp25-0nt R+3'Δ5nt+5' 3nt extension F | F | TAATACGACTCACTATAGGGGCATGCGCGGCGCATT ACC | CrRNA-sp25 0nt R+3'Δ5nt+5' 3nt extension |
| 44 | T7-Sp25-0nt R+3'Δ5nt+5' 3nt extension AS | R | GGTAATGCGCCGCGCATGCCCCTATAGTGAGTCGTAT TA | |
| 45 | T7-Sp25-0nt R+5' 5nt extension F | F | TAATACGACTCACTATAGGGCCGCATGCGCGGCGCA TTACCTTTAC | CrRNA-sp25 0nt R+5' 5nt extension |
| 46 | T7-Sp25-0nt R+5' 5nt extension AS | R | GTAAAGGTAATGCGCCGCGCATGCGGCCCTATAGTG AGTCGTATTA | |
| 47 | T7-Sp25-0nt R+3' 10nt extension F | F | TAATACGACTCACTATAGGGTGCGCGGCGCATTACCT TTACATATGATTAT | CrRNA-sp25 0nt R+3' 10nt extension |
| 48 | T7-Sp25-0nt R+3' 10nt extension AS | R | ATAATCATATGTAAAGGTAATGCGCCGCGCACCCTAT AGTGAGTCGTATTA | |
| 49 | T7- C RNA target 25 Forw | F | CAAGTCTAATACGACTCACTATAGGGTCAGCACGGCC AGCAATCCGGCGTAAAGGTAATGCGCCGCGCATGAG GAATAAAAATCTG | To generate ssRNA bearing sequence antisense to sp25 |
| 50 | T7- C RNA target 25 AS | R | CAGATTTTTATTCCTCATGCGCCGCGCATTACCTTTAC GCCGGATTGCTGGCCGTGCTGACCCTATAGTGAGTC GTATTAGACTTG | |

Figure 17 cont.

| | | | | |
|---|---|---|---|---|
| 51 | T7-tdtm-spcrRNA Forw | F | TAATACGACTCACTATAGGTAATCGGGGATGTCGGCG GTTTTAGAGCTATGCTGTTTTG | Sp. crRNA-tdtm |
| 52 | T7-tdtm-spcrRNA AS | R | CAAAACAGCATAGCTCTAAAACCGCCGACATCCCCGA TTACCTATAGTGAGTCGTATTA | |
| 53 | T7-eGFP-spcrRNA Forw | F | TAATACGACTCACTATAGGGCGAGGAGCTGTTCACC GGTTTTAGAGCTATGCTGTTTTG | Sp. crRNA-eGFP |
| 54 | T7-eGFP-spcrRNA Forw | R | CAAAACAGCATAGCTCTAAAACCGGTGAACAGCTCCT CGCCCTATAGTGAGTCGTATTA | |
| | *For generating in vitro transcription templates by PCR* | | | |
| 55 | T7-tdsp Forw | F | TAATACGACTCACTATAGGTAATCGGGGATGTCGGCG | PCR up templates for Sp. sgRNA-tdtm & Sp. tracrRNA |
| 56 | T7-Sptracr Forw | F | TAATACGACTCACTATAGGTCAAAACAGCATAGCAAG TTAAAATAAGGC | |
| 57 | End of Sptracr AS | R | AGCACCGACTCGGTGCCACTTTTTC | |
| | *For in vitro cleavage/binding assays (Mutations, underlined; PAMs, highlighted in grey.)* | | | |
| 58 | Sp25-NC (Non Complementary strand) | F | CAGATTTTTATTCCTCATGCGCGGCGCATTACCTTTAC GCCGGATTGCTGGCCGTGCTGA | |
| 59 | Sp25-C (Complementary strand) | R | TCAGCACGGCCAGCAATCCGGCGTAAAGGTAATGCG CCGCGCATGAGGAATAAAAATCTG | |
| 60 | Sp25-NC PAM Mut | F | CAGATTTTTATTCCTCATGCGCGGCGCATTACCTTTAC GCCGCTAAGCTGGCCGTGCTGA | |
| 61 | Sp25-C PAM Mut | R | TCAGCACGGCCAGCTTAGCGGCGTAAAGGTAATGCG CCGCGCATGAGGAATAAAAATCTG | |
| 62 | FAM- sp25-C | R | /56-FAM/ATTCAGCACGGCATATAATCATATGTAAAGGT AATGCGCCGCGCATGCGG | |
| 63 | FAM- sp25-C NO PAM | R | /56-FAM/ATTCAGCACGGCATATATAGATATGTAAAGGT AATGCGCCGCGCATGCGG | |
| 64 | CrDNA25 | F | TCATGCGCGGCGCATTACCTTTACGTTGTAGCTCCCTT TCTCATTTCG | |
| 65 | FAM-extended crDNA25 | F | /56-FAM/CCACCTGCTGAAGGAATAGTGCGCGGCGCAT TACCTTTACGTTGTAGCTCCCTTTCTCATTTCG | |
| 66 | Control RNA | - | AAGTTTGAAGGTGATACCCTTGTTAATAGAATCGAGTT AA | |
| 67 | Sp25-LK6-NC | F | CAGATTTTTATTCCTCATGCGCGGCGCATTACCTTTAC ATATATGATTGCTGGCCGTGCT | |
| 68 | Sp25-LK6-C | R | AGCACGGCCAGCAATCATATATGTAAAGGTAATGCGC CGCGCATGAGGAATAAAAATCTG | |
| 69 | Sp25-LK5-NC | F | CAGATTTTTATTCCTCATGCGCGGCGCATTACCTTTAC ATATAGATTGCTGGCCGTGCTG | |
| 70 | Sp25-LK5-C | R | CAGCACGGCCAGCAATCTATATGTAAAGGTAATGCGC CGCGCATGAGGAATAAAAATCTG | |
| 71 | Sp25-LK4-NC | F | CAGATTTTTATTCCTCATGCGCGGCGCATTACCTTTAC ATATGATTGCTGGCCGTGCTGA | |
| 72 | Sp25-LK4-C | R | TCAGCACGGCCAGCAATCATATGTAAAGGTAATGCGC CGCGCATGAGGAATAAAAATCTG | |
| 73 | Sp25-LK3-NC | F | CAGATTTTTATTCCTCATGCGCGGCGCATTACCTTTAC ATAGATTGCTGGCCGTGCTGAA | |
| 74 | Sp25-LK3-C | R | TTCAGCACGGCCAGCAATCATGTAAAGGTAATGCGC CGCGCATGAGGAATAAAAATCTG | |
| 75 | Sp25-LK2-NC | F | CAGATTTTTATTCCTCATGCGCGGCGCATTACCTTTAC ATGATTGCTGGCCGTGCTGAAG | |
| 76 | Sp25-LK2-C | R | CTTCAGCACGGCCAGCAATCATGTAAAGGTAATGCGC CGCGCATGAGGAATAAAAATCTG | |
| 77 | FAM- Sp tdtm- C | R | /56-FAM/CCAAGGCGTACGTGAAGCACCCGCCGACAT CCCCGATTACC | |
| 78 | 37nt NCsp25 | F | CAGATTTTTATTCCTCATGCGCGGCGCATTACCTTTA | Size markers for oligo cleavage assays |
| 79 | 36nt NCsp25 | F | CAGATTTTTATTCCTCATGCGCGGCGCATTACCTTT | |
| 80 | 35nt NCsp25 | F | CAGATTTTTATTCCTCATGCGCGGCGCATTACCTT | |
| 81 | 34nt NCsp25 | F | CAGATTTTTATTCCTCATGCGCGGCGCATTACCT | |
| 82 | 33nt NCsp25 | F | CAGATTTTTATTCCTCATGCGCGGCGCATTACCT | |
| 83 | 25nt Csp25 | R | TCAGCACGGCCAGCAATCCGGCGTA | |
| 84 | 24nt Csp25 | R | TCAGCACGGCCAGCAATCCGGCGT | |
| 85 | 22nt Csp25 | R | TCAGCACGGCCAGCAATCCGGC | |
| | *To construct plasmids for strain creation and protein expression* | | | |
| 86 | CR US Forw | F | GCCTGCATTAGGCTTGTTTCATAG | For pYZEJS087 |
| 87 | CR US AS+SalISpeI | R | ACTAGTATAGTCGACACTTCGACGGGAAATCCTTATTT C | |

Figure 17 cont.

| | | | | |
|---|---|---|---|---|
| 88 | SallSpel +CR DS Forw | F | GTCGACTATACTAGTCAGCCGTTGCGATAAGCGAAC | |
| 89 | CR DS AS | R | TGGTGCAATTTCTGTGTTGGACGG | |
| 90 | AatII+TracrUPForw | F | | For pYZEJS079 |
| 91 | TracrPro+Sp25 AS | R | GTAAAGGTAATGCGCCGCGCATGAGTTTGGGATTCTA GCCGTTGTGAG | |
| 92 | Sp25+R Forw | F | TCATGCGCGGCGCATTACCTTTACGTTGTAGCTCCCTT TCTCATTTCGG | |
| 93 | PacI+tracrend AS | R | TCGCTTAATTAATAAACGATGCCCCTTAAAGCAGAAGC | |
| 94 | PacI+trdel1 AS | R | TCGCTTAATTAAAAGCTTTAAGGGGCAGAGCGTTG | For pYZEJS162 |
| 95 | PacI+trdel2 AS | R | TCGCTTAATTAACGGCACATCTTTTCAGACGGCC | For pYZEJS163 |
| 96 | PacI+trdel3 AS | R | TCGCTTAATTAATCAGACGGCCTTATTGTAGCAAC | For pYZEJS164 |
| 97 | PacI+trdel4 AS | R | TCGCTTAATTAAATTGTAGCAACGGTTCTCATTTC | For pYZEJS165 |
| 98 | PacI+trdel6 AS | R | TCGCTTAATTAATAAAGCAGAAGCTTTAAGGGGCAG | For pYZEJS176 |
| 99 | HinddelSendPacI Forw | F | AGCTTCTGCTTTAAGGGGCATTAAT | For pYZEJS175 |
| 100 | HinddelSendpacI AS | R | TAATGCCCCTTAAAGCAGA | |
| 101 | Int 1 AS | R | GGGAGCTACAACGTAAAGGTAATGCG | For pYZEJS177 |
| 102 | OL+int1F | F | CCTTTACGTTGTAGCTCCCCGTTGCTACAATAAGGCC GTCTG | |
| 103 | Int 2 AS | R | ATTGTAGCAACGGTTCTCATTTC | For pYZEJS178 |
| 104 | OL+int2F | F | ATGAGAACCGTTGCTACAATCAACGCTCTGCCCCTTAA AGCTTC | |
| 105 | Int 3 AS | R | TTTCGGGAGCTACAACGTAAAGGTAATGCG | For pYZEJS179 |
| 106 | OL+int3F | F | CCTTTACGTTGTAGCTCCCGAAACGTTGCTACAATAAG GCCGTCTG | |
| 107 | NmeCas9 Forw-RR | F | TACTTCAATCCAATGCCATGGCTGCCTTCAAACC | For pYZEJS265 |
| 108 | NmeCas9 AS-RR | R | TTATCCACTTCCAATGTTTTAACGGACAGGCGG | |
| 109 | PGCC2 FwbeforeMCS | F | GCTCGAATTCCGATCATATTCAATAACCC | PGCC2 based sequencing |
| 110 | PGCC2 ASafterMCS | R | AGAACCATCCGTTCTGCTCTATACCCTCG | |

To construct plasmids with protospacer mutants and NmeCas9 mutants

All pGCC2-, pYZEJS040- and pMCSG7- based plasmids carrying point mutations in the protospacers, PAM or NmeCas9 were created by QuickChange mutagenesis and confirmed by sequencing. The oligos used are not listed (a) F, Forward; R, Reverse.

(b) Bold, T7 promoter; highlighted in grey, PAMs; underlined, mutations.

DNASE H ACTIVITY OF NEISSERIA MENINGITIDIS CAS9

CROSS REFERENCE

The present application is 371 U.S. national stage entry of International Patent Appl. No. PCT/US16/50396, having an international filing date of Sep. 6, 2016, which claims benefit of U.S. Appl. No. 62/215,424, a provisional application filed Sep. 8, 2015.

STATEMENT OF GOVERNMENTAL SUPPORT

This invention was made with government support awarded by the National Institutes of Health (Grant Number R01 GM093769). The government has certain rights in the invention.

A sequence listing has been submitted in an ASCII text file named "18417lrg.txt", created on Jul. 20, 2018, consisting of 32,867 bytes, the entire content of which is herein incorporated by reference.

FIELD OF THE INVENTION

The present invention is related to the field of gene editing. In particular, a *Neisseria meningitidis* Cas9 (NmeCas9) enzyme that efficiently cleaves single-stranded DNA (ssDNA) in an RNA-guided, tracrRNA-independent, guide-sequence-non-specific manner. As such, NmeCas9 "DNase H" cleavage sites are measured from the 5' end of a ssDNA's RNA-paired region.

BACKGROUND OF THE INVENTION

Type II CRISPR-Cas systems in bacteria defend against invasive genomes by using a single protein, Cas9, as a dual RNA-guided nuclease that creates double-stranded (dsDNA) DNA breaks. Dual RNAs (CRISPR RNA (crRNA) and tracrRNA) are required for Cas9's DNA targeting activities observed to date. Targeting requires a short protospacer adjacent motif (PAM) as well as crRNA-DNA complementarity. Many strains of the human pathogen *Neisseria meningitidis* carry a compact Cas9 (NmeCas9) that can serve to limit genetic exchange via natural transformation. Cas9 orthologues (including NmeCas9) have recently been adopted for RNA-guided genome engineering and DNA binding, adding to the need to define better their activities and properties.

What is needed is a CRISPR Cas9 composition that meets single stranded DNA targeting and CRISPR substrate requirements for the selective cleavage of single stranded deoxyribonucleic acids.

SUMMARY OF THE INVENTION

The present invention is related to the field of gene editing. In particular, a *Neisseria meningitidis* Cas9 (NmeCas9) enzyme that efficiently cleaves single-stranded DNA (ssDNA) in an RNA-guided, tracrRNA-independent, guide-sequence-non-specific manner. As such, NmeCas9 "DNase H" cleavage sites are measured from the 5' end of a ssDNA's RNA-paired region.

In one embodiment, the present invention contemplates a composition comprising a *Neisseria meningitidis* Cas9 (NmeCas9) enzyme and a guide RNA (gRNA) sequence, wherein the sgRNA lacks a transactivating CRISPR RNA (tracrRNA) sequence. In one embodiment, the sgRNA sequence comprises a CRISPR RNA (crRNA) sequence. In one embodiment, the composition further comprises a single stranded deoxyribonucleic acid (ssDNA) sequence. In one embodiment, the composition does not comprise a double stranded deoxyribonucleic acid (dsDNA) sequence. In one embodiment, the ssDNA sequence comprises a protospacer adjacent motif (PAM). In one embodiment, the crRNA sequence comprises at least one complementary region to the PAM. In one embodiment, the ssDNA sequence lacks a PAM. In one embodiment, the crRNA sequence comprises at least one complementary sequence to the ssDNA. In one embodiment, the gRNA sequence is seventeen nucleotides. In one embodiment, the NmeCas9 protein comprises an intact HNH domain. In one embodiment, the crRNA sequence comprises a mutated CRISPR repeat region. In one embodiment, the crRNA sequence does not have a CRISPR repeat region. In one embodiment, the ssDNA comprises a linker sequence adjacent to the PAM. In one embodiment, the linker sequence is approximately 2-6 nucleotides. In one embodiment, the linker sequence is 4 nucleotides.

In one embodiment, the present invention contemplates a method, comprising; a) providing: i) a patient exhibiting at least one symptom of a virus infection; and ii) a pharmaceutical composition comprising a *Neisseria meningitidis* Cas9 (NmeCas9) enzyme and a guide RNA (gRNA) sequence, wherein the sgRNA lacks a transactivating CRISPR RNA (tracrRNA) sequence; and b) administering the pharmaceutical composition to the patient under conditions such that at least one symptom of the virus infection is reduced. In one embodiment, the gRNA sequence comprises a CRISPR RNA (crRNA) sequence. In one embodiment, the virus infection comprises a single stranded viral deoxyribonucleic acid sequence. In one embodiment, the administering of the pharmaceutical composition cleaves the single stranded viral deoxyribonucleic acid sequence. In one embodiment, the single stranded viral deoxyribonucleic acid is single stranded hepatitis B virus deoxyribonucleic acid. In one embodiment, the single stranded viral deoxyribonucleic acid is single stranded retrovirus deoxyribonucleic acid. In one embodiment, the single stranded retrovirus deoxyribonucleic acid is single stranded lentivirus deoxyribonucleic acid. In one embodiment, the single stranded retrovirus deoxyribonucleic acid is single stranded human immunodeficiency virus deoxyribonucleic acid.

In one embodiment, the present invention contemplates a method, comprising: a) providing: i) a composition comprising a *Neisseria meningitidis* Cas9 (NmeCas9) enzyme and a guide RNA (gRNA) sequence, wherein the gRNA lacks a transactivating CRISPR RNA (tracrRNA) sequence; and ii) a mixture comprising double stranded deoxyribonucleic acid sequences and single stranded deoxyribonucleic acid sequences; b) contacting the composition with said mixture; under conditions such that the single stranded deoxyribonucleic acid sequences are cleaved; and c) purifying the double stranded deoxyribonucleic acid sequences from the mixture. In one embodiment, the gRNA sequence comprises a CRISPR RNA (crRNA) sequence.

Definitions

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "edit" "editing" or "edited" refers to a method of altering a nucleic acid sequence of a polynucleotide (e.g., for example, a wild type naturally occurring nucleic acid sequence or a mutated naturally occurring sequence) by selective deletion of a specific genomic target. Such a specific genomic target includes, but is not limited to, a chromosomal region, a gene, a promoter, an open reading frame or any nucleic acid sequence.

As used herein, the term "specific genomic target" refers to a pre-identified nucleic acid sequence of any composition and/or length. Such a specific genomic target includes, but is not limited to, a chromosomal region, a gene, a promoter, an open reading frame or any nucleic acid sequence. In some embodiments, the present invention interrogates these specific genomic target sequences with complementary sequences of gRNA.

As used herein, the term "lentiviral vector" refers to a gene delivery vehicle adapted from lentiviruses, a subclass of Retroviruses. Lentiviruses have recently been adapted as gene delivery vehicles (vectors) thanks to their ability to integrate into the genome of non-dividing cells, which is the unique feature of Lentiviruses as other Retroviruses can infect only dividing cells. The viral genome in the form of RNA is reverse-transcribed when the virus enters the cell to produce DNA, which is then inserted into the genome at a random position by the viral integrase enzyme.

As used herein, the term "CRISPRs" or "Clustered Regularly Interspaced Short Palindromic Repeats" refers to an acronym for DNA loci that contain multiple, short, direct repetitions of base sequences. Each repetition contains a series of bases followed by 30 or so base pairs known as "spacer DNA". The spacers are short segments of DNA from a virus and may serve as a 'memory' of past exposures to facilitate an adaptive defense against future invasions.

As used herein, the term "Cas" or "CRISPR-associated (cas)" refers to genes often associated with CRISPR repeat-spacer arrays.

As used herein, the term "Cas9" refers to a nuclease from Type II CRISPR systems, an enzyme specialized for generating double-strand breaks in DNA, with two active cutting sites (the HNH and RuvC domains), one for each strand of the double helix. Jinek combined tracrRNA and spacer RNA into a "single-guide RNA" (sgRNA) molecule that, mixed with Cas9, could find and cleave DNA targets through Watson-Crick pairing between the guide sequence within the sgRNA and the target DNA sequence.

As used herein, the term "catalytically active Cas9" refers to an unmodified Cas9 nuclease comprising full nuclease activity.

As used herein, the term "effector domain" refers to a protein domain that can: 1) affect either transcriptional repression or activation, 2) catalytically modify histones, or 3) catalytically chemically modify DNA.

As used herein, the term "fluorescent protein" refers to a protein domain that comprises at least one organic compound moiety that emits fluorescent light in response to the appropriate wavelengths. For example, fluorescent proteins may emit red, blue and/or green light. Such proteins are readily commercially available including, but not limited to: i) mCherry (Clonetech Laboratories): excitation: 556/20 nm (wavelength/bandwidth); emission: 630/91 nm; ii) sfGFP (Invitrogen): excitation: 470/28 nm; emission: 512/23 nm; iii) TagBFP (Evrogen): excitation 387/11 nm; emission 464/23 nm.

As used herein, the term "sgRNA" refers to single guide RNA used in conjunction with CRISPR associated systems (Cas). sgRNAs contains nucleotides of sequence complementary to the desired target site. Watson-crick pairing of the sgRNA with the target site recruits the nuclease-deficient Cas9 to bind the DNA at that locus.

As used herein, the term "orthogonal" refers targets that are non-overlapping, uncorrelated, or independent. For example, if two orthogonal nuclease-deficient Cas9 gene fused to different effector domains were implemented, the sgRNAs coded for each would not cross-talk or overlap. Not all nuclease-deficient Cas9 genes operate the same, which enables the use of orthogonal nuclease-deficient Cas9 gene fused to a different effector domains provided the appropriate orthogonal sgRNAs.

As used herein, the term "phenotypic change" or "phenotype" refers to the composite of an organism's observable characteristics or traits, such as its morphology, development, biochemical or physiological properties, phenology, behavior, and products of behavior. Phenotypes result from the expression of an organism's genes as well as the influence of environmental factors and the interactions between the two.

As used herein, the term "promoter" refers to a region of DNA that initiates transcription of a particular gene. Promoters are located near the genes they transcribe, on the same strand and upstream of the transcribed DNA (towards the 3' region of the anti-sense strand, also called template strand and non-coding strand).

As used herein, the term "constitutive promoter" refers to promoters that are active in all circumstances in the cell.

As used herein, the term "inducible promoter" or "regulated promoter" refers to promoters that become active in response to specific stimuli.

"Nucleic acid sequence" and "nucleotide sequence" as used herein refer to an oligonucleotide or polynucleotide, and fragments or portions thereof, and to DNA or RNA of genomic or synthetic origin which may be single- or double-stranded, and represent the sense or antisense strand.

The term "an isolated nucleic acid", as used herein, refers to any nucleic acid molecule that has been removed from its natural state (e.g., removed from a cell and is, in a preferred embodiment, free of other genomic nucleic acid).

The terms "amino acid sequence" and "polypeptide sequence" as used herein, are interchangeable and to refer to a sequence of amino acids.

As used herein the term "portion" when in reference to a protein (as in "a portion of a given protein") refers to fragments of that protein. The fragments may range in size from four amino acid residues to the entire amino acid sequence minus one amino acid.

The term "portion" when used in reference to a nucleotide sequence refers to fragments of that nucleotide sequence. The fragments may range in size from 5 nucleotide residues to the entire nucleotide sequence minus one nucleic acid residue.

As used herein, the terms "complementary" or "complementarity" are used in reference to "polynucleotides" and "oligonucleotides" (which are interchangeable terms that refer to a sequence of nucleotides) related by the base-pairing rules. For example, the sequence "C-A-G-T," is complementary to the sequence "G-T-C-A." Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands has significant effects on the efficiency and strength of hybridization between nucleic acid strands. This is of particular importance in amplification reactions, as well as detection methods which depend upon binding between nucleic acids.

The terms "homology" and "homologous" as used herein in reference to nucleotide sequences refer to a degree of complementarity with other nucleotide sequences. There may be partial homology or complete homology (i.e., identity). A nucleotide sequence which is partially complementary, i.e., "substantially homologous," to a nucleic acid sequence is one that at least partially inhibits a completely complementary sequence from hybridizing to a target nucleic acid sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding the probe will not hybridize to the second non-complementary target.

The terms "homology" and "homologous" as used herein in reference to amino acid sequences refer to the degree of identity of the primary structure between two amino acid sequences. Such a degree of identity may be directed to a portion of each amino acid sequence, or to the entire length of the amino acid sequence. Two or more amino acid sequences that are "substantially homologous" may have at least 50% identity, preferably at least 75% identity, more preferably at least 85% identity, most preferably at least 95%, or 100% identity.

An oligonucleotide sequence which is a "homolog" is defined herein as an oligonucleotide sequence which exhibits greater than or equal to 50% identity to a sequence, when sequences having a length of 100 bp or larger are compared.

Low stringency conditions comprise conditions equivalent to binding or hybridization at 42° C. in a solution consisting of 5×SSPE (43.8 g/l NaCl, 6.9 g/l NaH$_2$PO$_4$.H$_2$O and 1.85 g/l EDTA, pH adjusted to 7.4 with NaOH), 0.1% SDS, 5×Denhardt's reagent {50×Denhardt's contains per 500 ml: 5 g Ficoll (Type 400, Pharmacia), 5 g BSA (Fraction V; Sigma)} and 100 µg/ml denatured salmon sperm DNA followed by washing in a solution comprising 5×SSPE, 0.1% SDS at 42° C. when a probe of about 500 nucleotides in length is employed. Numerous equivalent conditions may also be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol), as well as components of the hybridization solution may be varied to generate conditions of low stringency hybridization different from, but equivalent to, the above listed conditions. In addition, conditions which promote hybridization under conditions of high stringency (e.g., increasing the temperature of the hybridization and/or wash steps, the use of formamide in the hybridization solution, etc.) may also be used.

As used herein, the term "hybridization" is used in reference to the pairing of complementary nucleic acids using any process by which a strand of nucleic acid joins with a complementary strand through base pairing to form a hybridization complex. Hybridization and the strength of hybridization (i.e., the strength of the association between the nucleic acids) is impacted by such factors as the degree of complementarity between the nucleic acids, stringency of the conditions involved, the T$_m$ of the formed hybrid, and the G:C ratio within the nucleic acids.

As used herein the term "hybridization complex" refers to a complex formed between two nucleic acid sequences by virtue of the formation of hydrogen bounds between complementary G and C bases and between complementary A and T bases; these hydrogen bonds may be further stabilized by base stacking interactions. The two complementary nucleic acid sequences hydrogen bond in an anti-parallel configuration. A hybridization complex may be formed in solution (e.g., C$_0$ t or R$_0$ t analysis) or between one nucleic acid sequence present in solution and another nucleic acid sequence immobilized to a solid support (e.g., a nylon membrane or a nitrocellulose filter as employed in Southern and Northern blotting, dot blotting or a glass slide as employed in in situ hybridization, including FISH (fluorescent in situ hybridization)).

As used herein, the term "T$_m$" is used in reference to the "melting temperature." The melting temperature is the temperature at which a population of double-stranded nucleic acid molecules becomes half dissociated into single strands. As indicated by standard references, a simple estimate of the T$_m$ value may be calculated by the equation: T$_m$=81.5+0.41 (% G+C), when a nucleic acid is in aqueous solution at 1M NaCl. Anderson et al., "Quantitative Filter Hybridization" In: *Nucleic Acid Hybridization* (1985). More sophisticated computations take structural, as well as sequence characteristics, into account for the calculation of T$_m$.

As used herein the term "stringency" is used in reference to the conditions of temperature, ionic strength, and the presence of other compounds such as organic solvents, under which nucleic acid hybridizations are conducted. "Stringency" typically occurs in a range from about T$_m$ to about 20° C. to 25° C. below T$_m$. A "stringent hybridization" can be used to identify or detect identical polynucleotide sequences or to identify or detect similar or related polynucleotide sequences. For example, when fragments are employed in hybridization reactions under stringent conditions the hybridization of fragments which contain unique sequences (i.e., regions which are either non-homologous to or which contain less than about 50% homology or complementarity) are favored. Alternatively, when conditions of "weak" or "low" stringency are used hybridization may occur with nucleic acids that are derived from organisms that are genetically diverse (i.e., for example, the frequency of complementary sequences is usually low between such organisms).

As used herein, the term "probe" refers; to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the terms "restriction endonucleases" and "restriction enzymes" refer to bacterial enzymes, each of which cut double-stranded DNA at or near a specific nucleotide sequence.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

The term "transfection" or "transfected" refers to the introduction of foreign DNA into a cell.

As used herein, the terms "nucleic acid molecule encoding", "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the term "gene" means the deoxyribonucleotide sequences comprising the coding region of a structural gene and including sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into heterogeneous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenylation.

The term "label" or "detectable label" are used herein, to refer to any composition detectable by spectroscopic, photochemical, biochemical, immunochemical, electrical, optical or chemical means. Such labels include biotin for staining with labeled streptavidin conjugate, magnetic beads (e.g., Dynabeads®), fluorescent dyes (e.g., fluorescein, texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads. Patents teaching the use of such labels include, but are not limited to, U.S. Pat. Nos. 3,817,837; 3,850,752; 3,939,350; 3,996,345; 4,277,437; 4,275,149; and 4,366,241 (all herein incorporated by reference). The labels contemplated in the present invention may be detected by many methods. For example, radiolabels may be detected using photographic film or scintillation counters, fluorescent markers may be detected using a photodetector to detect emitted light. Enzymatic labels are typically detected by providing the enzyme with a substrate and detecting, the reaction product produced by the action of the enzyme on the substrate, and calorimetric labels are detected by simply visualizing the colored label.

BRIEF DESCRIPTION OF THE FIGURES

The accompanying figures, which are incorporated into and form a part of the specification, illustrate several embodiments of the present invention and, together with the description, serve to explain the principles of the invention. The figures are only for the purpose of illustrating a preferred embodiment of the invention and are not to be construed as limiting the invention.

The file of this patent contains at least one drawing executed in color. Copies of this patent with color drawings will be provided by the Patent and Trademark Office upon request and payment of the necessary fee.

FIG. 1 shows a schematic overview of a CRISPR system.

FIG. 1A: *S. pyogenes* Cas9 (SpyCas9) recognizes a target sequence through Watson-Crick pairing of 20 bases of the sgRNA and recognition of the neighboring PAM sequence (NGG) (SEQ ID NO: 8) by a Cas9 protein (Jinek et al., 2012).

FIG. 1B: *N. meningitidis* Cas9 (NmeCas9) utilizes a 24 base guide sequence in its sgRNA and the neighboring PAM sequence (NNNNGANN (SEQ ID NO: 1) or NNNNGTTN (SEQ ID NO: 2)) for target recognition.

FIG. 3 presents exemplary data showing that NmeCas9 functions as an RNA-guided DNA endonuclease.

FIG. 3A: A Coomassie-stained 10% denaturing PAGE of wild-type and mutant NmeCas9 proteins. WT: wild-type NmeCas9; D16A, H588A, and D16A+H558A: active site NmeCas9 mutants D16A, H588A, and D16A+H558A. The predicted molecular weight of NmeCas9 is ~110 kD. Weights of molecular markers are indicated.

FIG. 3B: A schematic showing the complex of the spacer (sp) 9 crRNA, the tracrRNA, and the target DNA duplex. Yellow, crRNA spacer; grey, crRNA repeat; red, GATT PAM (SEQ ID NO: 17); black arrows, predicted NmeCas9 cleavage sites.

FIG. 3C: Plasmid cleavage by NmeCas9 requires tracrRNA, the cognate crRNA and Mg2+. N, nicked; L, linearized; SC: supercoiled.

FIG. 3D: Sanger sequencing of an NmeCas9 linearized pGCC2-ps 9 plasmid. Black arrows indicate predicted cleavage sites and the green stars indicate the A overhangs added by the sequencing reactions.

FIG. 4A: Time course analysis for NmeCas9 cleavage. Cleavage by NmeCas9 is rapid under these conditions, nearing completion within five minutes. N, nicked; L, linearized; SC: supercoiled.

FIG. 4B: Effect of salt (KCl) concentration on NmeCas9 cleavage. The optimum KCl concentration for NmeCas9 cleavage is 0-300 mM, while KCl concentrations ≥400 mM are inhibitory. N, nicked; L, linearized; SC: supercoiled.

FIG. 5A: Schematic representation of the location of the RuvC and HNH domains in the primary sequence of NmeCas9.

FIG. 5B: Plasmid cleavage assays were performed using wild-type NmeCas9, as well as active site mutants D16A, H588A, and D16A+H588A. In the presence of Mg2+, the D16A and H588A mutants cause nicking of the plasmid, whereas the double mutant is inactive. The HNH domain is more flexible in its metal requirements since the D16A mutant can nick plasmids with Ca2+ or Ba2+, whereas the H588A mutant cannot. N, nicked; L, linearized; SC: supercoiled.

FIG. 5C: NmeCas9 uses the HNH and RuvC nuclease domains to cleave the crRNA-complementary and non-complementary strands, respectively. The oligonucleotide cleavage assay was performed using tracrRNA- and crRNA-programmed, wild-type and mutant NmeCas9 proteins at 37° C. for 30 min. Duplex DNA substrates were 5' $^{32}$P labeled on either strand. The D16A mutant only cleaves the complementary strand, whereas the H588A mutant only cleaves the non-complementary strand. M, size markers. The sizes of the substrates, cleavage products and markers are indicated.

FIG. 6 presents exemplary data showing that NmeCas9 exhibits tracrRNA-independent ssDNA cleavage activity.

FIG. 6A: Schematic representation of ps 25-containing DNA oligonucleotides and the sp 25 crRNA used in FIG. 6B, FIG. 6C and FIG. 6D. Red lettering, PAM; yellow, crRNA spacer; gray, crRNA repeat; black arrows, predominant cleavage sites for dual-RNA guided NmeCas9 cleavage; red arrow, predominant cleavage site for tracrRNA-independent NmeCas9 cleavage.

FIG. 6B: NmeCas9 cleaves ssDNA efficiently in a tracrRNA-independent manner. NmeCas9 complexed with small RNAs was assayed for cleavage of double- (left) or single- (right) stranded DNA targets for sp 25. The complementary strand was 5' $^{32}$P radiolabeled. M, size markers. The sizes of substrates, cleavage products and markers are indicated.

FIG. 6C: NmeCas9 binds an ssDNA target in vitro in a tracrRNA-independent manner. Electrophoretic mobility shift assays (EMSAs) were performed using a 5' FAM-labeled ssDNA substrate (100 nM), NmeCas9 (500 nM), and various small RNAs (500 nM) as indicated. Binding was performed in cleavage reaction buffer (but with Mg2+ omitted) at room temperature for 10 min, and then resolved by 5% native PAGE. NmeCas9 binds ssDNA when a cognate crRNA is present, even in the absence of tracrRNA.

FIG. 6D: An intact HNH domain plays a role in tracrRNA-independent cleavage of complementary strand ssDNA. Wildtype and active-site-mutant NmeCas9s were assayed for cleavage of ssDNA, in the absence (left) or presence (right) of tracrRNA. M, size marker. The sizes of substrates, cleavage products and markers are indicated.

FIG. 8C: NmeCas9 determines the DNase H cleavage sites by a ruler mechanism that measures from the 5' end of the DNA in the RNA-DNA hybrid, and requires a minimum 17-18 base paired region. All RNA guides have a 5'-terminal GGG trinucleotide to facilitate in vitro transcription, so the lengths of the DNA-RNA hybrid duplexes are 3 nt shorter than the RNA guides.

FIG. 8D: Inverting the backbone composition of the guide-substrate duplex also inverts the strand asymmetry of the cleavage activity. Replacing the crRNA with a crDNA abolishes activity, indicating that the guide must be an RNA. However, additionally replacing the ssDNA target with the corresponding ssRNA results in crDNA cleavage, reinforcing the conclusion that NmeCas9 exhibits DNase H activity. 1, 2' and 3' denote the control reactions including only the labeled DNA component for substrate pairs 1, 2, and 3, respectively.

FIG. 9A: NmeCas9 cleaves a FAM-labeled ssDNA target pre-incubated with SSB protein regardless of the presence or absence of tracrRNA. The FAM-labeled ssDNA oligonucleotide was targeted for sp 25. Cleavage reactions such that the ssDNA target was pre-incubated with increasing amounts of SSB in standard cleavage buffer before the addition of crRNA, tracrRNA and NmeCas9. The sizes of the substrates and cleavage products are indicated.

FIG. 9B: NmeCas9 cleaves a FAM-labeled ssDNA target pre-incubated with RecA protein, regardless of the presence or absence of tracrRNA. The FAM-labeled ssDNA oligonucleotide was targeted for sp 25. Cleavage reactions were performed such that the ssDNA target was pre-incubated with increasing amounts of RecA in standard cleavage buffer before the addition of crRNA, tracrRNA and NmeCas9. The sizes of the substrates and cleavage products are indicated.

FIG. 9C: FAM-labeled ssDNA targets are bound by higher concentrations of SSB or RecA after the pre-incubation, as revealed by EMSA.

FIG. 10 presents exemplary data showing that NmeCas9 functions with a range of PAM variants.

FIG. 10A: NmeCas9 cleavage of plasmids containing ps 9 and wild-type or mutant PAMs. NmeCas9 was programmed with tracrRNA and the sp 9 crRNA. Mutations in the PAM are indicated in red, and PAMs are in bold.

FIG. 10B: NmeCas9 targets a range of PAM variants in a cellular interference assay. Plasmids containing ps 25 and various PAM mutants were tested by natural transformation assays using wild-type MC8013 cells as recipients. The bar graphs are log-scale plots of colony-forming units (CFU)/ml (mean±s.e.m.) for total cells (blue bars) and erythromycin-resistant (ErmR) transformants (red bars) from three independent experiments. The positions and nt identities of the mutations are indicated for each PAM variant.

FIG. 10C: PAM residues are required on both strands to license NmeCas9 cleavage on a duplex DNA substrate. NmeCas9 programmed with tracrRNA and sp 25 crRNA were tested for oligonucleotide cleavage. Non-C, non-complementary strand; C, complementary strand. Duplex DNA oligos were 5' $^{32}$P-labeled on both strands. Mutant PAM sequences are shown (below the gel) in red, with the PAM region in bold.

FIG. 10D: NmeCas9 cleavage of ssDNA targets does not require a PAM. The oligonucleotide cleavage assay was performed with 5' FAM-labeled complementary ssDNA oligos (100 nM). NmeCas9 was programmed either with sp 25 crRNA alone or together with tracrRNA. PAM mutations are indicated (below the gel) in red, and PAMs are in bold. The "No PAM" oligonucleotide carries a triple mutation in the PAM.

FIG. 11 presents exemplary data showing that NmeCas9 has a strong preference for the 1st Guanine within PAM that is not a spacer-specific effect.

FIG. 11A: A schematic of the ps 24-containing DNA targets and sp 24 sgRNA. In red, PAM; highlighted in yellow, crRNA spacer; highlighted in gray, crRNA repeat.

FIG. 11B: pYZEJS040 derivatives with WT and mismatched targets for sp 24 were tested by natural transformation assays. Experiments were done twice with similar results, and the data shown here are from one representative experiment.

FIG. 13 presents exemplary data showing that NmeCas9 has minimal tolerance for protospacer-PAM linker length variation.

FIG. 13A: NmeCas9 can function with a 4 bp linker in bacterial cells. Left, cellular interference assay. Plasmids containing ps 23 and its linker length mutant derivatives were tested in natural transformation assays. Sequences of the linkers between ps 23 and its PAM in the mutants used are shown on the right. The linkers are in red.

FIG. 13B: The same plasmids as tested in FIG. 14A were assayed for cleavage in vitro by NmeCas9 programmed with sp 23 crRNA and tracrRNA. N, nicked; L, linearized; SC: supercoiled.

FIG. 13C: NmeCas9 cleavage of the non-complementary strand in DNA duplexes is much less efficient when the linker length varies, and the cut site moves in concert with the PAM. The duplex DNAs were 5' $^{32}$P labeled on the non-complementary strand only, and contain ps 25, a flanking GATT PAM (SEQ ID NO: 17) and a 2-6 nt linker in between. NmeCas9 was programmed with tracrRNA and sp 25 crRNA. M, size markers. The sizes of substrates, cleavage products and markers are indicated.

FIG. 13D: NmeCas9 cleavage of the complementary strand ssDNA is as efficient when linker length varies, and the cut sites are at a fixed position. The ssDNA targets were 5' $^{32}$P labeled, and contain ps 25, a flanking GATT PAM (SEQ ID NO: 17), and a 2-6 nt linker in between. NmeCas9 was programmed with sp 25 crRNA and with or without tracrRNA, as indicated. M, size markers. The sizes of substrates, cleavage products and markers are indicated.

FIG. 14 presents exemplary data shown NmeCas9's cleavage site requirements in Bacterial Cells and in vitro.

FIG. 14A: A schematic of ps 9-containing DNA targets and sp 9 crRNA. In red, PAM; highlighted in yellow, spacer 9 of the crRNA; highlighted in gray, crRNA repeat. Representative mismatched targets are shown below, with mutations marked in red. Positions of the mutated nts within ps 25 (counting from the PAM-distal end) are indicated on the left.

FIG. 14B: NmeCas9 tolerates most of the 1-nt but not 2-nt mismatches in the cleavage site during interference in bacteria. pGCC2 derivatives containing ps 9 with various 1-nt and 2-nt cleavage site mutations were tested by natural transformation assays.

FIG. 15 presents exemplary data showing that NmeCas9's cleavage site sequence requirements in bacterial cells are not spacer context-dependent.

FIG. 15A: A Schematic of ps 25-containing DNA targets and sp 25 crRNA. In red, PAM; highlighted in yellow, crRNA spacer; highlighted in gray, crRNA repeat. Representative mismatched targets are shown below, with mismatches marked in red and positions of the mutated nts indicated on the left.

FIG. 15B: NmeCas9 tolerates many 1-nt but not 2-nt mismatches in the cleavage site region of protospacer 25 during interference in bacteria. pYZEJS040 derivatives containing ps 25 with various 1-nt and 2-nt cleavage site mutations were assayed for interference using natural transformation assays.

FIG. 16 presents exemplary data showing NmeCas9 sgRNA requirements in vitro and in bacteria.

FIG. 16A: A schematic of a NmeCas9 sgRNA, a chimeric fusion in which the 3' end of the mature crRNA and the 5' end of the mature tracrRNA are connected by a GAAA tetraloop. Highlighted in yellow, crRNA spacer; highlighted in gray, crRNA repeat. Six 3' terminal truncations are indicated in red, and three internal deletions are indicated by colored boxes.

FIG. 16B: Full-length and variant sgRNAs were assayed for NmeCas9 cleavage of ps 9-containing plasmid in vitro. NmeCas9 was programmed with tracrRNA and sp 9 crRNA. N, nicked; L, linearized; SC: supercoiled.

FIG. 16C: Schematics of representative MC8013 isogenic strains. Relevant genotypes are given on the left. Grey boxes, genes; blue boxes, kanamycin-resistance marker; black rectangles, CRISPR repeats; white diamonds, CRISPR spacers; green boxes, tracrRNA promoter.

FIG. 17 shows exemplary oligonucleotides considered in the current invention. The oligonucleotides are used for generating in vitro transcription templates by annealing; for generating in vitro transcription templates by PCR; for in vitro cleavage/binding assays; to construct plasmids for strain creation and protein expression; and to construct plasmids with protospacer mutants and NmeCas9 mutants.

DETAILED DESCRIPTION OF THE INVENTION

Figure 2:
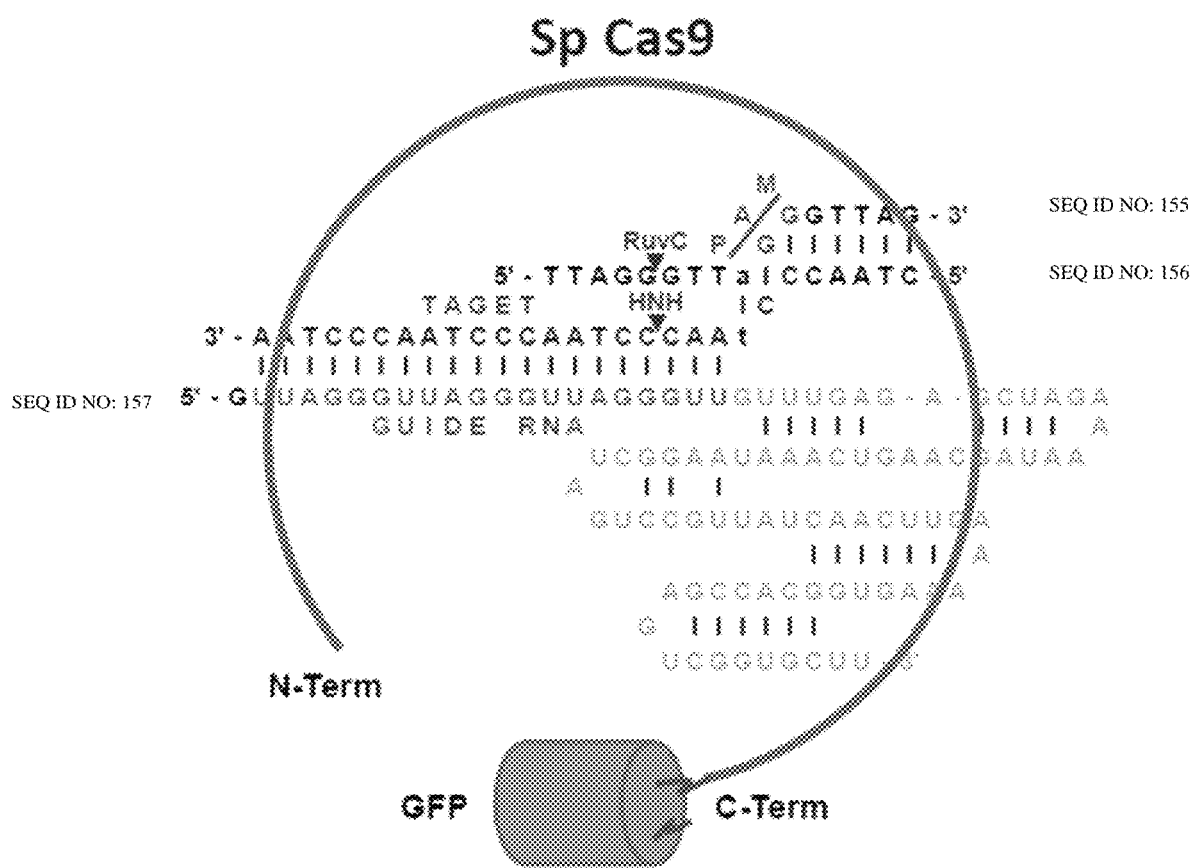
FIG. 2 illustrates one embodiment of an *S. pyogenes* Spy dCas9 binding configuration comprising a 20 mer target DNA sequence, an Spy sgRNA sequence and an NGG PAM sequence (SEQ ID NO: 8) attached to a green fluorescent protein (GFP).

The following detailed description, and the figures to which it refers, are provided for the purpose of describing and illustrating certain preferred embodiments or examples of the invention only, and no attempt has been made to exhaustively describe all possible embodiments or examples of the invention. Thus, the following detailed description and the accompanying figures shall not be construed to limit, in any way, the scope of the claims recited in this patent application and any patent(s) issuing there from.

The present invention is related to the field of gene editing. In particular, a *Neisseria meningitidis* Cas9 (Nme-Cas9) enzyme that efficiently cleaves single-stranded DNA (ssDNA) in an RNA-guided, tracrRNA-independent, guide-sequence-non-specific manner. As such, NmeCas9 "DNase H" cleavage sites are measured from the 5' end of a ssDNA's RNA-paired region.

In one embodiment, the present invention contemplates a recombinant NmeCas9 comprising DNase H activity. Although it is not necessary to understand the mechanism of an invention, it is believed that NmeCas9 DNase H activity clearly distinguishes NmeCas9 from other Cas9 orthologues characterized to date. In one embodiment, NmeCas9 efficiently catalyzes tracrRNA-independent cleavage of a single-stranded DNA (ssDNA) target. Although it is not necessary to understand the mechanism of an invention, it is believed that this activity can employ guide RNAs that lack CRISPR repeat-derived sequences, and are substantially shorter (~17-18 nt) than regular crRNAs (~45 nt) or sgRNAs (~100 nt). When programmed by RNA guides lacking tracrRNA domains or CRISPR repeats, NmeCas9 has a clear substrate preference, i.e. it cleaves only ssDNA, but not dsDNA. In one embodiment, the present invention contemplates a composition comprising an ssDNA-RNA paired region having DNase H cleavage sites that are measured from the 5' end. Although it is not necessary to understand the mechanism of an invention, it is believed that NmeCas9 single strand DNA cleavage does not require the presence of a PAM in a ssDNA target. Collectively, this activity is referred to herein as NmeCas9 DNase H activity that provides RNA-guided ssDNA cleavage activity that is PAM-independent and tracrRNA-independent.

Although it is not necessary to understand the mechanism of an invention, it is believed that NmeCas9 DNase H activity provides several advantages over similar systems conventional in the art. NmeCas9 DNase H activity has advantages over ZFNs and TALENs in that it only requires a new short guide RNA for each target site, while ZFNs and TALENs require a new pair of proteins for every target site. NmeCas9 DNase H activity can catalyze programmable ssDNA cleavage, thereby employing much shorter (~17-18 nt) RNA guides that do not contain any sequences derived from either a tracrRNA or a CRISPR repeat. When programmed without tracrRNA or CRISPR repeats, NmeCas9 has a clear substrate preference, i.e. cleaves only ssDNA, but not dsDNA. NmeCas9 DNase H activity has advantages over RNase H. RNase H is believed to degrade the RNA strand of a RNA-DNA hybrid with little or no sequence preference. In contrast, NmeCas9's DNase activity makes specific cuts and has the opposite nucleic acid specificity, in that it cleaves the DNA strand of the hybrid duplex and not the RNA strand. The DNase H cut sites are determined by a ruler mechanism measured from the 5' end of the ssDNA's RNA-paired region.

Unexpectedly, NmeCas9 was found to be able to cleave single-stranded DNA (ssDNA) targets in a manner that is RNA-guided but both PAM-independent and tracrRNA-independent. Beyond the requirement for guide-target pairing, this activity has no apparent sequence requirements, and cleavage sites are measured from the 5' end of the DNA substrate's RNA-paired region. These results indicate that tracrRNA domains are not strictly required for enzymatic activation of NmeCas9, and expand the list of targeting activities exhibited by these revolutionary RNA-guided nucleases.

In one embodiment, the present invention contemplates an NmeCas9 comprising DNase H activity (NmeCas9/DNase H) to provide a programmable, RNA-guided "restriction enzyme" that cleaves ssDNA, with no sequence constraints whatsoever in the target. In one embodiment, the NmeCas9/DNase H comprising a seventeen (17) nt RNA guide. While conventional Cas9s can cleave ssDNA they require a much longer single guide RNA, thereby making them considerably more expensive or cumbersome to obtain and employ.

In one embodiment, the present invention contemplates an NmeCas9/DNase H providing a programmable destruction of single-stranded DNA regions in a genome. In one embodiment, the single-stranded DNA regions comprise DNA viruses. In one embodiment, the DNA virus is Hepatitis B virus. Although it is not necessary to understand the mechanism of an invention, it is believed that because of the absence of a tracrRNA sequence, a NmeCase9/DNase H would not cleave unwanted and/or off-target lesions in the host cell genome. In one embodiment, the present invention contemplates an NmeCas9/DNase H providing a sequence non-specific clearance (i.e. not programmed by exogenous RNA guides) of retroviruses (such as lentivirus and human immunodeficiency virus; HIV) that rely on RNA-DNA hybrid intermediates.

I. Clustered Regularly Interspaced Short Palindromic Repeat (CRISPR) as a Gene Editing Platform Until recently, genome editing was difficult in mammalian cells. One way to improve genome-editing efficiency is to introduce a double-strand break (DSB) in the desired DNA region. Currently, there are three widely used platforms to introduce targeted DSBs in genomes of mammalian cells—ZFNs (Zinc Finger Nucleases, TALENs (Transcription activator-like effector nucleases), and the recently developed CRISPRs. Both ZFNs and TALENs are engineered by fusing site-specific DNA recognition domains to FokI endonucleases, and it takes weeks to design, express and validate a new pair of proteins for each target site. The CRISPR-Cas9 systems now provide revolutionary tools for facile, RNA-programmable genome engineering.

Recently, an RNA-guided adaptive immune system that is widespread in bacteria and archaea has been engineered for targeted DNA cleavage or gene regulation in prokaryotic and eukaryotic genomes. Wiedenheft, B. et al. (2012) "RNA-guided genetic silencing systems in bacteria and archaea," Nature 482(7385), 331-338; and Charpentier, E. and Doudna, J. A. (2013) "Biotechnology: Rewriting a genome," Nature 495(7439), 50-51. This system generally has three components: i) a Cas9 endonuclease; ii) a tracrRNA, and iii) a target-specifying crRNA. By fusing the crRNA and tracrRNA into a single transcript referred to as an sgRNA, the machinery can be further streamlined into a two-component system.

Genome editing and dsDNA cleavage by Cas9 endonucleases is facilitated by regions of sgRNAs that correspond to the tracrRNA and to the CRISPR repeat within crRNAs. Two Cas9 nuclease domains (i.e., for example, RuvC and HNH) each cleave one DNA target strand and thus induce a Double Stranded Break (DSB). The target DNA sequence that base-pairs with the crRNA is referred to as the "protospacer." Cleavage of dsDNAs by Cas9 also depends on the presence of a short motif called a protospacer adjacent motif (PAM) that flanks the target region recognized by crRNA base pairing. Type II CRISPR/Cas systems from different bacteria have distinct PAM requirements. For example, for *S. pyogenes* Cas9 (SpyCas9) the PAM is 5'-NGG3' (SEQ ID NO: 8), while for *N. meningitidis* (NmeCas9), the PAM is 5'-NNNNGATT3' (SEQ ID NO: 3) (in both cases the dash represents the terminal nucleotide of the crRNA-paired sequence).

CRISPR (clustered, regularly interspaced, short palindromic repeats) loci and CRISPR-associated (Cas) proteins provide an RNA-guided adaptive immune system for bacteria and archaea (Barrangou and Marraffini, 2014; van der Oost et al., 2014; Sontheimer and Barrangou, 2015). CRISPRs consist of ~24-48 base pair (bp) repeats separated by similarly sized, non-repetitive spacers, which often match the sequences of fragments of phage genomes or plasmids (Bolotin et al., 2005; Mojica et al., 2005; Pourcel et al., 2005). Genetic interference specified by CRISPR-Cas pathways can protect against phage infection (Barrangou et al., 2007), and can also limit horizontal gene transfer (Marraffini and Sontheimer, 2008; Bikard et al., 2012; Zhang et al., 2013).

CRISPR RNAs (crRNAs) (Brouns et al., 2008; Hale et al., 2008) are usually processed from a longer crRNA precursor (pre-crRNA). Each crRNA associates with one or more Cas proteins to form an interference complex that locates complementary "protospacer" regions in the foreign nucleic acids, and makes sequence-specific cuts in the invasive genetic element, preventing its establishment or expression (Barrangou and Marraffini, 2014; van der Oost et al., 2014; Sontheimer and Barrangou, 2015).

CRISPR-Cas systems are classified into five major types (I-V), based primarily on the identities of the Cas proteins involved in crRNA processing and interference (Makarova et al., 2015). The only Cas proteins shared by all five types are Cas1 and Cas2, both of which are important for acquiring new CRISPR spacers (Yosef et al., 2012; Nunez et al., 2014; Nunez et al., 2015), but dispensable for the interference function of existing spacers (Brouns et al., 2008). Type II systems are distinguished partially by the involvement of a single protein (Cas9), which includes RuvC and HNH nuclease domains, for interference (Sapranauskas et al., 2011; Gasiunas et al., 2012; Jinek et al., 2012), along with a transactivating CRISPR RNA (tracrRNA) (Deltcheva et al., 2011) that functions in both pre-crRNA processing and interference. The type II systems are further divided into subtypes II-A, -B, and -C, based in part on the presence or absence of additional spacer acquisition factors Csn2 and Cas4 (Makarova et al., 2015).

Some pathogenic bacteria carry type II systems that are not only involved in genome defense, but that also modulate bacterial physiology and pathogenicity (Gunderson and Cianciotto, 2013; Louwen et al., 2013; Sampson et al., 2013; Sampson et al., 2014). Interest in type II CRISPR-Cas systems has increased dramatically due to its successful adoption as an RNA-guided, locus-specific, genome editing and DNA binding platform in eukaryotes (Doudna and Charpentier, 2014; Hsu et al., 2014). Cas9 functions as an RNA-programmable DNA endonuclease using the HNH and RuvC nuclease domains to cleave the crRNA-complementary and non-complementary strands, respectively (Gasiunas et al., 2012; Jinek et al., 2012). The normally separate crRNA and tracrRNA cofactors can be fused into a single-guide RNA (sgRNA) without loss of activity (Jinek et al., 2012).

Target cleavage by Cas9 requires the presence of a short (usually 2-5 nt) protospacer adjacent motif (PAM) that flanks the target region specified by crRNAs (Deveau et al., 2008; Garneau et al., 2010; Gasiunas et al., 2012; Jinek et al., 2012), and the PAM sequence varies among Cas9 orthologs. CrRNA/target complementarity must be nearly perfect in the 7-12 nt "cleavage site" region proximal to the PAM (Sapranauskas et al., 2011; Gasiunas et al., 2012; Jinek et al., 2012). The application of CRISPR/Cas9 in genome editing has sparked interest in characterizing different type II systems to identify Cas9 orthologs with distinct and perhaps improved genome targeting capabilities. To date, the editing functions of Cas9s from *Streptococcus pyogenes* (SpyCas9, Type II-A) (Jinek et al., 2012; Cho et al., 2013; Cong et al., 2013; Hwang et al., 2013; Jiang et al., 2013; Jinek et al., 2013; Mali et al., 2013), *Streptococcus thermophilus* (Sth1Cas9 and Sth3Cas9, both Type II-A) (Gasiunas et al., 2012; Cong et al., 2013; Esvelt et al., 2013; Chen et al., 2014), and *N. meningitidis* (NmeCas9, Type II-C) (Esvelt et al., 2013; Hou et al., 2013) are best characterized.

NmeCas9 (Zhang et al., 2013) is of interest because it is almost 300 amino acids smaller than the commonly used SpyCas9, and this reduced size may facilitate its delivery via virus or mRNA-based vectors. More recently, a second Cas9 in this smaller size range from 6 *Staphylococcus aureus* (SauCas9, Type II-A) has also been adopted for genome editing (Ran et al., 2015). Certain pairs of Cas9 proteins and their respective guide RNAs are orthogonal (i.e., a guide RNA loads into the intended cognate Cas9 but not into the orthologous Cas9) (Esvelt et al., 2013; Briner et al., 2014; Fonfara et al., 2014), facilitating multiplexed applications.

The structures of apo-SpyCas9 (Jinek et al., 2014), and its complexes with an sgRNA (Jiang et al., 2015) or an sgRNA and an ssDNA target (Nishimasu et al., 2014), show that the protein consists of two main lobes, a recognition lobe and a nuclease lobe, and that the RNA-DNA heteroduplex is bound at the interface of the two lobes. The structure of SpyCas9 with an sgRNA and a partially duplexed target DNA revealed the molecular basis for SpyCas9's recognition of its 5'-NGG-3' (SEQ ID NO: 8) PAM (Anders et al., 2014). The GG dinucleotide present in the non-crRNA-complementary strand is recognized by major groove interactions mediated by two arginines in the C-terminal domain of SpyCas9 (Anders et al., 2014). These high-resolution structures will likely assist with protein/nucleic acid engineering for developing a refined Cas9/sgRNA complex with improved genome editing capabilities.

The structure of a more compact type II-C Cas9 from *Actinomyces naeslundii* (AnaCas9) has been reported (Jinek et al., 2014), but relevant functional information for that protein (e.g. editing efficiency and PAM specificity) is limited. Accordingly, there is a significant need to understand better the properties of the more compact Cas9s such as NmeCas9 and others from Type II-C.

The data presented herein defines mechanistic requirements and/or features of NmeCas9 for target DNA cleavage and cellular interference. The data show that NmeCas9 has many characteristics in common with SpyCas9, Sth1Cas9, Sth3Cas9, and SauCas9 (characterized as Cas9 orthologs), including cleavage site specificity, mismatch sensitivity, and protospacer-PAM linker length dependence.

In contrast, NmeCas9 differs from SpyCas9 in that mutation of either strand of the target PAM inhibits doublestranded (ds) DNA target cleavage. Most strikingly, even in the absence of its tracrRNA cofactor, NmeCas9 can efficiently cleave single-stranded target DNA (ssDNA) in a crRNA-guided fashion, and this "DNase H-like" activity depends upon an intact HNH domain. Thus, NmeCas9 has target recognition capabilities that have not been observed previously in other orthologs and that could be useful for engineering applications.

Clustered regularly interspaced short palindromic repeat (CRISPR) RNA sequences and CRISPR-associated (Cas) genes generate catalytic protein-RNA complexes that utilize the incorporated RNA to generate sequence-specific double strand breaks at a complementary DNA sequence (Bhaya et al., 2011). The Cas9 nuclease from *Streptococcus pyogenes* (hereafter, Cas9) can be guided to specific sites in the human genome through base-pair complementation between a 20 nucleotide guide region of an engineered single-guide RNA (sgRNA) and a genomic target sequence (Mali et al., 2013b; Cho et al., 2013; Cong et al., 2013; Jinek et al., 2013). A catalytically-inactive programmable RNA-dependent DNA-binding protein (dCas9) can be generated by mutating the endonuclease domains within Cas9, which can modulate transcription in bacteria or eukaryotes either directly (Qi et al., 2013; Bikard et al., 2013) or through an incorporated effector domain (Gilbert et al., 2013a; Mali et al., 2013a; Konermann et al., 2013; Maeder et al., 2013; and Perez-Pinera et al., 2013).

CRISPR-based defense systems are found broadly in bacterial and archaeal systems. Type II systems employ a single protein, Cas9, to facilitate RNA-guided cleavage of a target DNA sequence complementary to the sgRNA and the protospacer adjacent motif (PAM) recognized by Cas9, where both elements must be recognized to achieve efficient DNA cleavage. Sorek, R. et al. (2013) "CRISPR-Mediated Adaptive Immune Systems in Bacteria and Archaea," Annu. Rev. Biochem. 82(1), 237-266; and Hsu, P. D. et al. (2013) "DNA targeting specificity of RNA-guided Cas9 nucleases," Nat. Biotechnol. 31(9), 827-832; see also FIG. 1A. The Cas9 nuclease from *S. pyogenes* (hereafter, SpyCas9) can be targeted to a specific sequence through Watson-Crick pairing between a 20 nucleotide guide region of an engineered single-guide RNA (sgRNA) and a target sequence. The *N. meningitidis* Cas9 (NmeCas9) recognizes a larger PAM element and employs a different (orthogonal) guide RNA. Hou, Z. et al. (2013) "Efficient genome engineering in human pluripotent stem cells using Cas9 from *Neisseria meningitidis*," P.N.A.S. 110(39), 15644-15649; and Zhang, Y. et al. (2013) "Processing-Independent CRISPR RNAs Limit Natural Transformation in *Neisseria meningitidis*," Mol. Cell 50(4), 488-503; see also FIG. 1B.

Various systems involving CRISPR-Cas systems have been described. For example, a prokaryotic type II CRISPR-Cas systems can be adapted to enable targeted genome modifications across a range of eukaryotes. Mali, P. et al. (2013). The reference describes an engineered system to enable RNA-guided genome regulation in human cells by tethering transcriptional activation domains either directly to a nuclease-null Cas9 protein or to an aptamer-modified single guide RNA (sgRNA). Using this functionality a transcriptional activation-based assay was developed to determine the landscape of off-target binding of sgRNA:Cas9 complexes and compared it with the off-target activity of transcription activator-like (TALs) effectors.

A CRISPR targeting process that relies on CRISPR components is sequence-specific and, upon simultaneous introduction of a plurality of custom guide RNA (gRNAs), can effect multiplex editing of target loci. Mali, et al. (2013). The reference describes engineering the type II bacterial CRISPR system to function with custom (gRNA) in human cells. For the endogenous AAVS1 locus, targeting rates of 10 to 25% in 293T cells was obtained, 13 to 8% in K562 cells, and 2 to 4% in induced pluripotent stem cells. The reference describes the results as establishing an RNA-guided editing tool for facile, robust, and multiplexable human genome engineering.

An approach that combines a Cas9 nickase mutant with paired guide RNAs to introduce targeted double-strand breaks. Ran, F. A. et al. (2013) "Double Nicking by RNA-Guided CRISPR Cas9 for Enhanced Genome Editing Specificity," Cell 154(6), 1380-1389. Because individual nicks in the genome are repaired with high fidelity, simultaneous nicking via appropriately offset guide RNAs is required for double-stranded breaks and extends the number of specifically recognized bases for target cleavage. The reference describes that using paired nicking can reduce off-target activity by 50- to 1,500-fold in cell lines and to facilitate gene knockout in mouse zygotes without sacrificing on-target cleavage efficiency. The reference speculates that the versatile strategy enables a wide variety of genome editing applications that require high specificity.

A CRISPR-Cas system from *Neisseria meningitides* has been used to demonstrate efficient targeting of an endogenous gene in three hPSC lines using homology-directed repair (HDR). Hou, et al. (2013). The Cas9 RNA-guided endonuclease from *N. meningitidis* (NmeCas9) recognizes a 5'-NNNNGATT-3' (SEQ ID NO: 3) protospacer adjacent motif (PAM) different from those recognized by Cas9 proteins from *S. pyogenes* and *S. thermophilus* (SpyCas9 and SthCas9, respectively). Similar to SpyCas9, NmeCas9 is able to use a single-guide RNA (sgRNA) to direct its activity. Because of its distinct protospacer adjacent motif, the *N. meningitidis* CRISPR-Cas machinery increases the sequence contexts amenable to RNA-directed genome editing.

A "CRISPRi system" derived from the *Streptococcus pyogenes* CRISPR pathway has been described, requiring only the coexpression of a catalytically inactive Cas9 protein (lacking nuclease activity) and a customizable single guide RNA (sgRNA). Larson, M. H. et al. (2013) "CRISPR interference (CRISPRi) for sequence-specific control of gene expression," Nat. Protoc. 8(11), 2180-2196. The Cas9-sgRNA complex binds to DNA elements complementary to the sgRNA and causes a steric block that halts transcript elongation by RNA polymerase, resulting in the repression of the target gene.

The present invention may utilize as targets any one of a number of CRISPR repetitive tandem repeat sequences. See, Table 1.

TABLE 1

Exemplary Types Of CRISPR Tandem Repetitive Targets

| Genomic Location | Repeat Sequence Template |
|---|---|
| Telomeres | TTAGGG (SEQ ID NO: 4) |
| Pericentromeric (Satellite II/III) | ATTCC (SEQ ID NO: 5) |

TABLE 1-continued

Exemplary Types Of CRISPR Tandem Repetitive Targets

| Genomic Location | Repeat Sequence Template |
|---|---|
| Expansions | CTG (SEQ ID NO: 6); GGGGCC (SEQ ID NO: 7) |
| Subtelomeric/Acrocentric (chromosome specific) | 10-100 base pairs |

The present invention provides compositions and methods for genomic editing using orthogonal Cas9 variants from three bacterial species; *S. pyogenes*, *N. meningitidis* (Nme) and *S. thermophilus* (Sth1) which have been used for gene editing in human cells without cross-talk in cognate sgRNA binding. Esvelt K M, et al. Orthogonal Cas9 proteins for RNA-guided gene regulation and editing. Nat. Methods 10(11):1116-1121. See, Table 2. Recognition Sequences

| Cas9 Bacterial Source | Target DNA Sequence Size | sgRNA Source | PAM Sequences |
|---|---|---|---|
| *S. pyogenese* (Spy Cas9) | 9-20 mers | Spy sgRNA | NGG (SEQ ID NO: 8) NAG (SEQ ID NO: 9) NGT (SEQ ID NO: 10) |
| *N. meningitidis* (Nme Cas9) | 20-24 mers | Nme sgRNA | NNNNGATT (SEQ ID NO: 3) NNNNGTTT (SEQ ID NO: 11) NNNNGCTT (SEQ ID NO: 12) |
| *S. thermophilus* (Sth Cas9) | 20 mers | St1 sgRNA | NNAGAAW (SEQ ID NO: 13) NNGGAAW (SEQ ID NO: 14) NNAGGAW (SEQ ID NO: 15) NNAGGGW (SEQ ID NO: 16) |

In one embodiment, a binding configuration of an *S. pyogenes* dCas9 comprises a 20 mer target DNA sequence, an Spy sgRNA sequence and an NGG PAM sequence (SEQ ID NO: 8). FIG. 2.

IV. In Vitro NmeCas9 Double-Stranded DNA Cleavage Activity

Figure 3E:
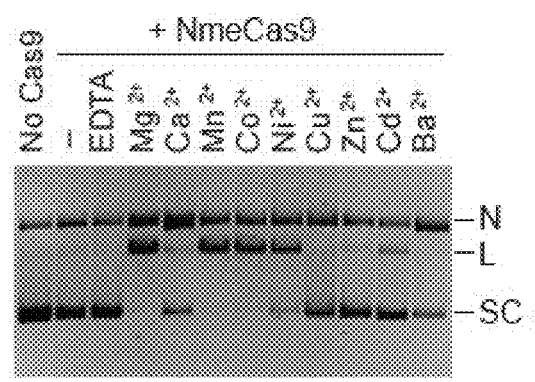
FIG. 3E: Divalent metal ion specificity of NmeCas9. Plasmid cleavage assay was performed as in FIG. 3C, except that dual RNAs were used for all lanes. The EDTA control shows the absolute requirement of divalent metal for the reaction. Divalent metals Mg2+, Mn2+, Co2+, and Ni2+ support NmeCas9-mediated double stranded DNA cleavage, while divalent metals Ca2+ and Ba2+ support plasmid nicking, suggesting that they only function within one of the two active sites. Metals Cu2+, Zn2+, and Cd2+ support little or no NmeCas9 activity.

To define the biochemical properties of NmeCas9 (*N. meningitidis* strain 8013; MC8013), the protein was over-expressed and purified *E. coli* BL21(DE3) Rosetta cells. Zhang et al., 2013. RuvC (D16A) and HNH (H588A) domain active site mutants, as well as the corresponding double mutant (D16A, H588A) were also purified. See, FIG. 3A. In vitro transcription was used to generate a tracrRNA and a crRNA containing spacer 9 (sp 9) from strain 8013. The complex of these RNAs, when paired with protospacer 9 (ps 9) target DNA (including the PAM region), is depicted. See, FIG. 3B. This protospacer 9 target sequence was previously validated as a functional target in CRISPR interference of DNA transformation (Zhang et al., 2013).

Plasmid cleavage assays showed that NmeCas9 cleaves dsDNA containing the matched protospacer and the reaction requires the cognate crRNA, tracrRNA, and magnesium. See, FIG. 3C. Sanger sequencing of the linearized plasmid identified the primary cleavage site to be between the 3rd and 4th nts of the protospacer counting from the PAM-proximal end. See, FIG. 3D.

Figure 4:
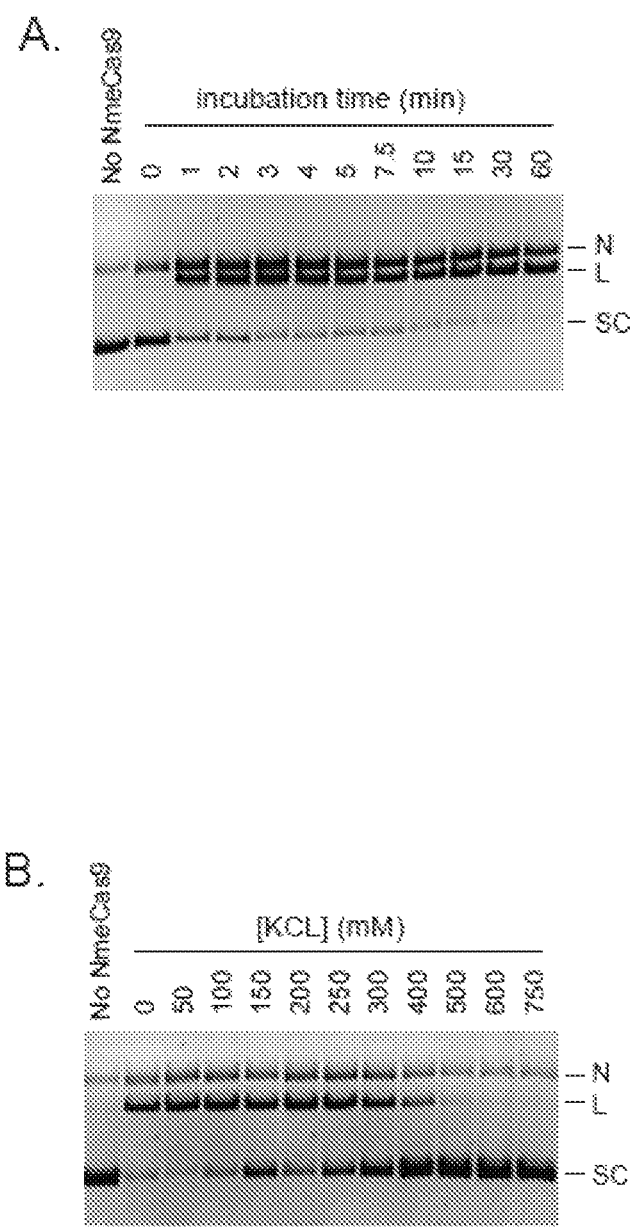
FIG. 4 presents exemplary data showing a biochemical characterization of NmeCas9-catalyzed plasmid DNA cleavage.

In a time course experiment, cleavage of the plasmid is substantially complete after 5 min of incubation. See, FIG. 4A. NmeCas9 exhibited robust activity at salt (KCl) concentration lower than 300 nM, and minimal or no activity above 500 nM. See, FIG. 4B. Divalent metal ion specificity of NmeCas9's DNA cleavage activity was also tested. See, FIG. 3E. Divalent metals such as Mg2+, Mn2+, Co2+, and Ni2+ support cleavage of both strands, whereas Ca2+ and Ba2+ only support plasmid nicking, suggesting that they can function with only one of the endonuclease domains of NmeCas9. Other metals such as Cu2+, Zn2+ and Cd2+ support little or no NmeCas9 cleavage.

Figure 5:
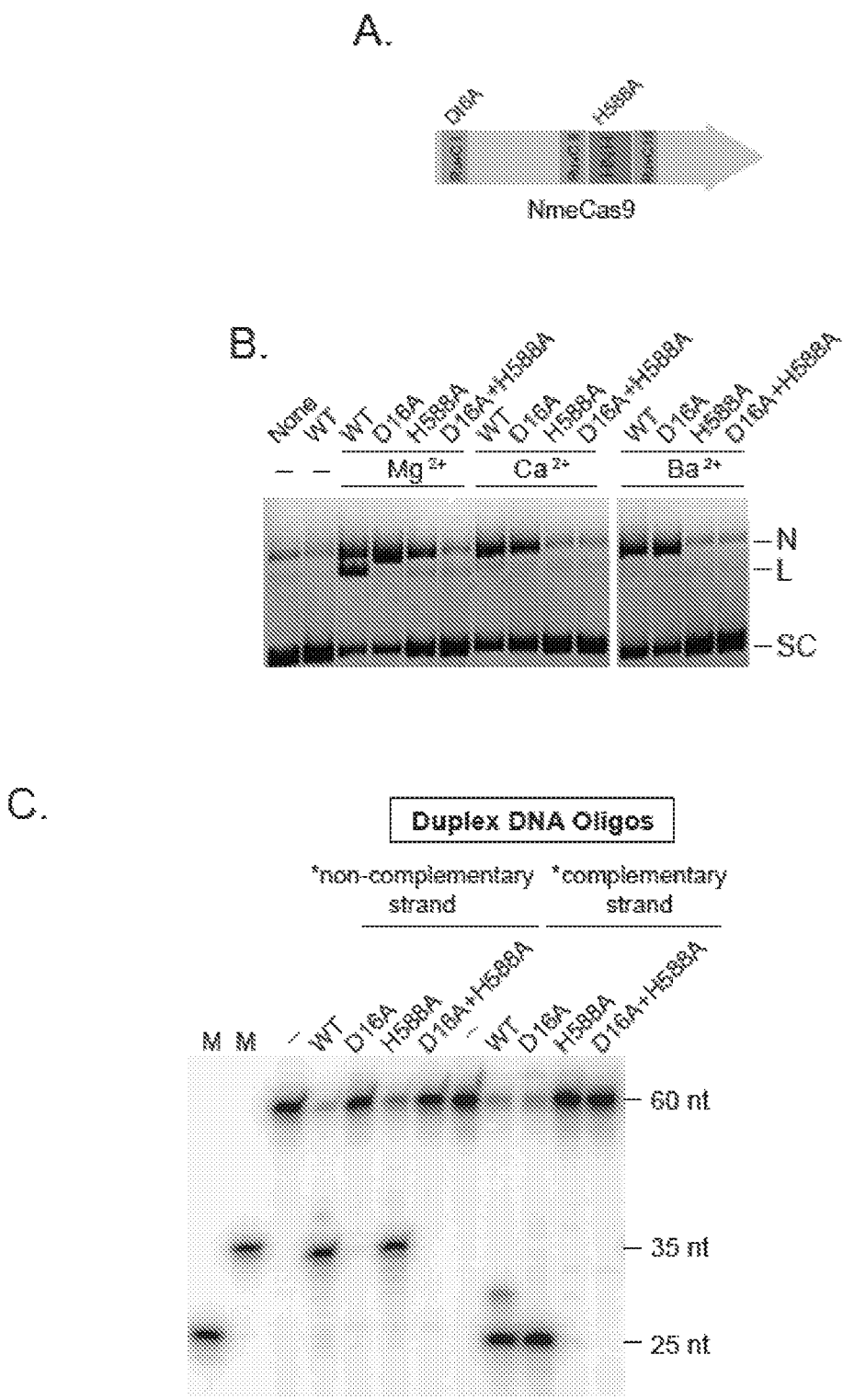
FIG. 5 presents exemplary data showing strand specificity of NmeCas9's two metal-dependent nuclease domains

A schematic representation of the domain organization of NmeCas9 is shown where three RuvC motifs together comprise an active RuvC domain. See, FIG. 5A. Based on sequence alignments, residues D16 (in the RuvC-I domain) and H588 (in the HNH domain) of NmeCas9 are essential active site residues of the enzyme (Esvelt et al., 2013; Zhang et al., 2013; Kearns et al., 2015). To test the involvement of these residues in NmeCas9 catalytic activity in vitro, mutant proteins D16A, H588A, and the double mutant (D16A, H588A) were expressed and purified. See, FIG. 3A. The plasmid cleavage assays showed that D16A and H588A mutants could each nick the plasmid, whereas the double mutant was inactive. Whereas Mg2+ supported the activity of both RuvC and HNH domains, divalent metals such as Ca2+ and Ba2+ only supported the catalytic activity of the HNH domain. See, FIG. 5B.

To determine the strand specificities of the catalytic domains and to test NmeCas9 activities on additional protospacers, synthetic oligonucleotides were designed corresponding to targets of MC8013 spacer. The crRNA-complementary or non-complementary strand of the annealed oligonucleotide duplex were radioactively labeled and the cleavage activity was tested for the wild-type and mutant proteins. The D16A mutant only cleaved the complementary strand in the target DNA duplex, indicating that the RuvC domain is responsible for the non-complementary strand cleavage. Similarly, the H588A mutant only cleaved the non-complementary strand, suggesting that the HNH domain is responsible for complementary strand cleavage. See, FIG. 5C.

Collectively, these experiments confirm that NmeCas9, like all other Cas9 orthologs studied to date, is an RNA-guided DNA endonuclease requiring tracrRNA, a cognate crRNA, and a divalent metal ion for activity. The HNH and the RuvC domains each cleave the crRNA-complementary and non-complementary DNA strands, respectively, targeting 3-4 bp into the protospacer, and each domain has different metal cofactor requirements.

Figure 7:
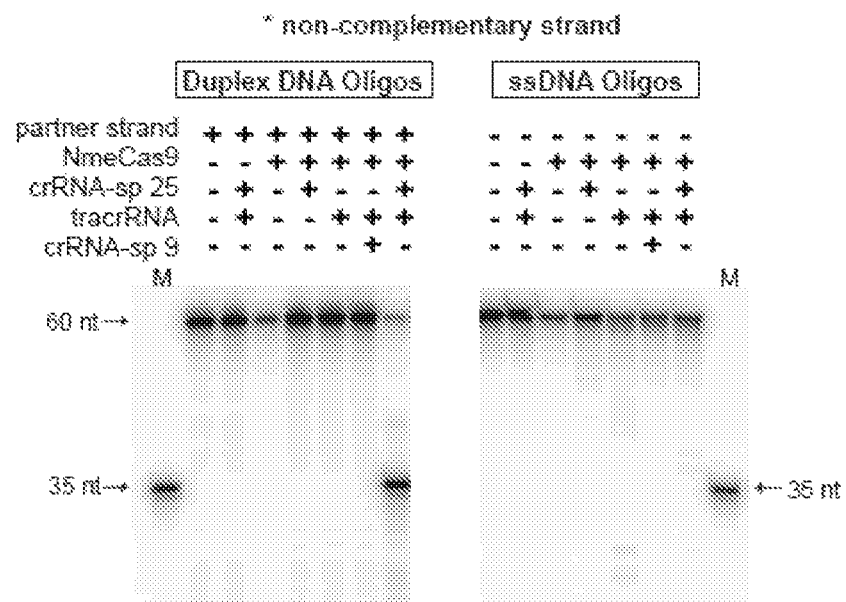
FIG. 7 presents exemplary data showing that NmeCas9 cleavage of the non-complementary strand requires the tracrRNA. NmeCas9/RNA complexes were assayed for cleavage of double- (left) or single- (right) stranded DNA substrates bearing a previously verified functional target for sp 25. The non-complementary strand was 5' $^{32}$P-labeled. M, size markers. The sizes of the substrates, cleavage products and markers are indicated.

V. NmeCas9 Cleaves ssDNA Targets in a CrRNA-Programmed but TracrRNA-Independent Fashion It is generally believed that conventional Cas9 endonucleases require both crRNA and tracrRNA to cleave their DNA targets. Jinek et al., 2012; Chen et al., 2014; and Fonfara et al., 2014. For example, a conventionally constructed NmeCas9 requires both RNAs to cleave either a supercoiled plasmid DNA or alternatively a 60 bp, fully duplexed dsDNA substrate. See, FIG. 3C and FIG. 7, respectively. The data shown herein demonstrate that no cleavage was observed when either NmeCas9, tracrRNA, or cognate crRNA (sp 25) was omitted from the reaction. Cleavage of both strands of the DNA duplex only occurred when both tracrRNA and cognate crRNA were included with NmeCas9. See, FIG. 6B and FIG. 7, respectively. This result indicates that conventionally constructed NmeCas9 requires dual RNAs to cleave duplex DNAs, consistent with previously studied Cas9 orthologues.

When using the complementary strand ssDNA substrate, NmeCas9 also catalyzed cleavage when programmed with both cognate crRNA (sp 25) and tracrRNA. See, FIG. 6B. The most predominant product was 25 nt, indicating cleavage between the third and fourth nts of the protospacer, though smaller amounts of cleavage were also observed one nt upstream and downstream from this site. Surprisingly, robust cleavage of the complementary strand was also achieved when NmeCas9 is programmed with the cognate crRNA alone, i.e. without the tracrRNA. This tracrRNA-independent mode of ssDNA cleavage was dependent on the complementary crRNA spacer, since cleavage is not observed when a non-cognate crRNA (sp 9) or no crRNA is present. Interestingly, the cleavage pattern of the "no tracrRNA" reaction is different from the pattern observed when the tracrRNA was included in the reaction. See, FIG. 6B. In the former case, several 22-26 nt products were observed, with the 24 nt form dominating, whereas in the latter case 24-26 nt products were observed with the 25 nt form dominating. This cleavage pattern reflects a 1-nt shift of the primary NmeCas9 cut site in the PAM-proximal direction when tracrRNA was omitted from the reaction. See, FIGS. 6A and 6B, respectively.

An electrophoretic mobility shift assay (EMSA) was performed to investigate whether both RNAs were required for stable ssDNA binding by NmeCas9. All divalent metal ions were omitted from the binding reaction to render NmeCas9 catalytically inactive. A 50-nt, fluorescently labelled, ssDNA target (containing ps 25 and the PAM) was bound by NmeCas9 when a cognate crRNA (sp 25) and the tracrRNA were both present, but not when a non-cognate crRNA (sp 23) was used instead. A robust ssDNA target binding occurred when NmeCas9 was programmed with a cognate crRNA alone, but not with the tracrRNA alone, or with a non-cognate crRNA alone. See, FIG. 7C. These results indicate that sequence-specific binding of an ssDNA target by NmeCas9 can occur in a tracrRNA-independent manner, and that divalent cations are not required for NmeCas9's target binding ability. RNA binding studies demonstrated NmeCas9 binding to a variety of RNA substrates (e.g., crRNA, tracrRNA and tRNAs), showing that NmeCas9 has nonspecific RNA-binding activity (data not shown). However, the tracrRNA-independent, crRNA-guided ssDNA cleavage shows that crRNA is sufficient to engage NmeCas9 in an enzymatically productive fashion. See, FIG. 6C.

To investigate which of the two nuclease motifs is responsible for cleaving ssDNA in a tracrRNA-dependent and tracrRNA-independent manner, D16A and H588A "nickases" were tested in the ssDNA oligo cleavage assay. Both modes of ssDNA cleavage, regardless of tracrRNA presence, were retained by the D16A nickase mutant but lost by the H588A nickase mutant, and the D16A+H588A double mutant. See, FIG. 6D. These results indicate that NmeCas9 uses the HNH domain to cut the complementary strand in ssDNA targets, as it does in duplex DNA substrates. The mature crRNAs for NmeCas9 contain a 24 nt sequence derived from CRISPR spacers and a 24 nt sequence derived from the CRISPR repeats. Zhang et al., 2013; see, also FIG. 6A.

Figure 8A:
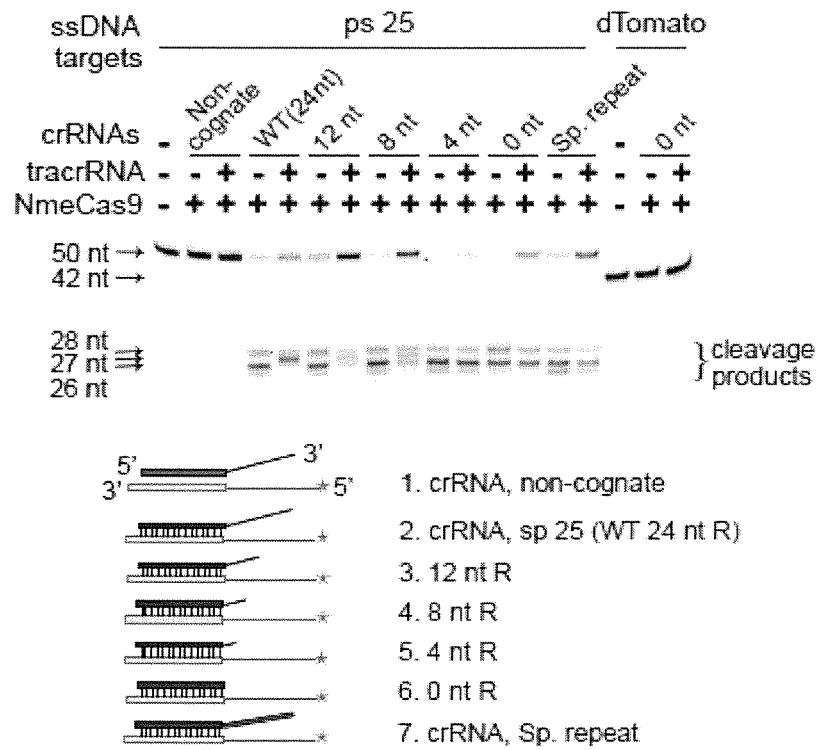
FIG. 8A: NmeCas9-catalyzed, crRNA-guided, tracrRNA-independent ssDNA cleavage does not require specific CRISPR repeats. Sp 25-specific crRNAs with repeat variants were assayed for NmeCas9-directed cleavage of an ssDNA target. In the absence of tracrRNA, the cleavage of ssDNA is not affected by alteration or complete deletion of the CRISPR repeat region of the crRNA. Here the cleavage reactions were performed using a 5' FAM-labeled ssDNA bearing an sp 25 target. The sizes of substrates and cleavage products are indicated. The panel of RNAs and substrates examined are depicted below the gel image and are colored as follows: DNA, brown lines and boxes with brown borders; RNA, black lines and boxes with black borders; ps 25, yellow; sp 25 sequences, red; sp 23 sequences, green; *S. pyogenes* (Spy) repeat, blue; 5' labels, stars. The non-cognate target is a 42-nt 5' FAM-labeled ssDNA from the dTomato gene.

To define a minimal region of CRISPR repeats required for tracrRNA-independent, ssDNA cleavage, serial 3' deletions of the crRNA repeat were created. In all of these guide sequences, a 24 nt spacer sequence remained intact, but CRISPR repeats were progressively truncated from 24 nt to 12, 8, 4, and 0 nt, respectively. The ability of each truncated RNA to guide NmeCas9-catalyzed cleavage of a cognate, 50 nt fluorescently-labelled ssDNA target was assayed, with or without tracrRNA. See, FIG. 8A. Surprisingly, in the absence of tracrRNA, the cleavage pattern of the ssDNA target was not affected by the serial 3' truncations of CRISPR repeat, nor by replacement of the 24 nt *N. meningitidis* repeat with a 20 nt *S. pyogenes* repeat (crRNA, Spy repeat).

These results show that the CRISPR repeat within the crRNA is dispensable for the tracrRNA-independent ssDNA cleavage by NmeCas9. The sp 25-containing target was not cleaved by NmeCas9 with a non-cognate crRNA, and the mutant sp 25 guide that lacks all repeat residues failed to direct NmeCas9 cleavage of a non-cognate ssDNA target specific to the dTomato fluorescent reporter gene. Hou et al., 2013; see, also FIG. 8A. These observations indicate that a base-paired RNA-DNA hybrid is necessary for the tracrRNA-independent activity of NmeCas9. This activity is reminiscent of the RNase H activity that cleaves the RNA strand of an RNA-DNA hybrid duplex (with little or no sequence preference), except that NmeCas9's activity has the opposite nucleic acid specificity (i.e. it cleaves the DNA strand of the hybrid duplex), and it cleaves at specific locations. Tadokoro and Kanaya, 2009. In one embodiment, the present invention contemplates that this tracrRNA-independent, RNA-guided ssDNA cleavage activity as DNase H-like.

In contrast to the tracrRNA-independent activity, progressive truncations of the CRISPR repeat in the presence of the tracrRNA lead to marked changes in the cleavage pattern. A 3' deletion of half or two-thirds of the repeat caused a shift from a pattern with one dominating product (i.e., for example, a 27 nt product, indicating cleavage between the 3rd and 4th nts of the protospacer) to a pattern with three to four species, ranging in size between approximately 25-28 nts. Further shortening of the repeat to 4 or 0 nts, or replacement of the *N. meningititidis* repeat by the *S. pyogenes* repeat, each resulted in a cleavage pattern identical to that of the tracrRNA-independent cleavage with 26 and 28 nt products dominating. See, FIG. 8A. These data suggest that the repeat/anti-repeat base pairing within a crRNA/tracrRNA duplex may play a role in dual RNA-mediated ssDNA cleavage by NmeCas9.

Figure 8B:
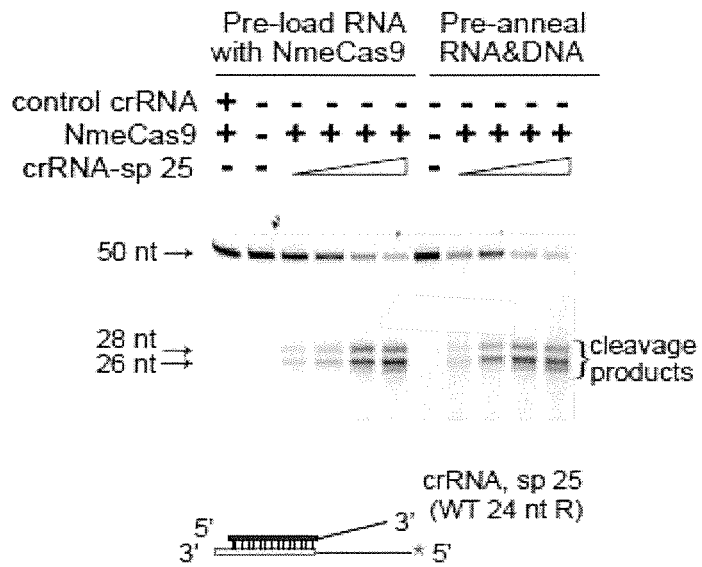
FIG. 8B: ssDNA target cleavage by NmeCas9 is as efficient when crRNA is pre-annealed to DNA substrates (right), as compared to crRNA that is given the opportunity to pre-load into NmeCas9 (left). Sp 25 crRNA (25, 50, 250, and 500 nM) is pre-annealed with ssDNA substrates (50 nM) in cleavage buffer at 37° C. for 10 min. Pre-loading of crRNA (25, 50, 250, and 500 nM) with NmeCas9 (500 nM) is done in cleavage buffer at 37° C. for 10 min.

To determine whether NmeCas9's DNase H activity requires a pre-loaded guide RNA, it was tested whether it can cleave the ssDNA in an RNA-DNA hybrid that was pre formed in solution, in the absence of the enzyme. TracrRNA-independent ssDNA cleavage was assayed using guide RNAs that were either pre-annealed with the ssDNA target before the addition of NmeCas9, or pre-incubated with NmeCas9 before the addition of DNA target. See, FIG. 8B, right and FIG. 8B, left, respectively. The cleavage patterns were similar under these two conditions, reinforcing the idea that NmeCas9 has a DNase H activity that cleaves the DNA strand of a RNA-DNA hybrid.

Rules governing DNase H cleavage site selection were investigated by assaying a panel of RNA guides with various extensions or truncations compared to the sp 25 guide that lacks all repeat residues (0 nt R). See, FIG. 8C. Cleavage sites were found to move in concert with the 5' end of the ssDNA's RNA-paired region. See, FIG. 8C, compare substrates 4 and 5 vs. 6 and 7, and vs. 8. However, cleavage sites did not move in concert with the 3' end of the RNA-paired region. See, FIG. 8C, compare substrates 4 vs. 5, and 6 vs. 7. This observation indicates that the cleavage sites of NmeCas9's DNase H activity may be set by a ruler mechanism that measures from the 5' end of the ssDNA's RNA paired region. This activity requires a minimum of 17-18 bps of RNA-DNA hybrid duplex, since the activity was lost when a 16 nt guide RNA was used. See, FIG. 8C, compare substrates 3, 4, and 5. A DNA guide that contains sequences identical to the sp 25 crRNA did not support NmeCas9's ssDNA cleavage activity at all, regardless of the tracrRNA's presence. See, FIG. 8D, substrate 2. Finally, when the nucleic acid identities of the guide and the target were reversed (i.e., with a crDNA "guide" and a presumptive ps 25-containing ssRNA "target"), it was the crDNA that was cleaved, at positions close to the 5' end of the RNA-paired region. See, FIG. 8D, substrate 3. These results reveal an RNA-directed ssDNA cleavage activity of NmeCas9 that does not depend upon tracrRNA or a PAM, or on any guide sequences that are specific to the *N. meningitidis* crRNAs.

Meningococcal cells are constitutively competent for natural transformation, which requires the degradation of one of the two DNA strands during uptake into the cytoplasm. Rotman and Seifert, 2014. The internalized ssDNA is then thought to associate with RecA protein, single-strand binding protein (SSB), or both, to protect against nuclease degradation and to facilitate the identification of complementary chromosomal sequences for homologous recombination. Johnston et al., 2014.

Figure 9:
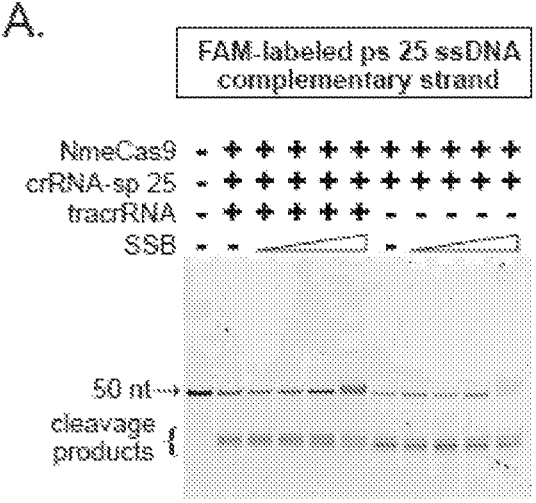
FIG. 9 presents exemplary data showing that NmeCas9 cleaves ssDNA pre-bound with SSB or RecA proteins.
Figure 9:
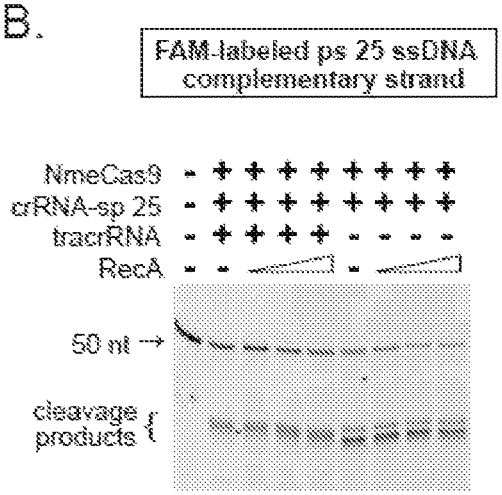
Figure 9:
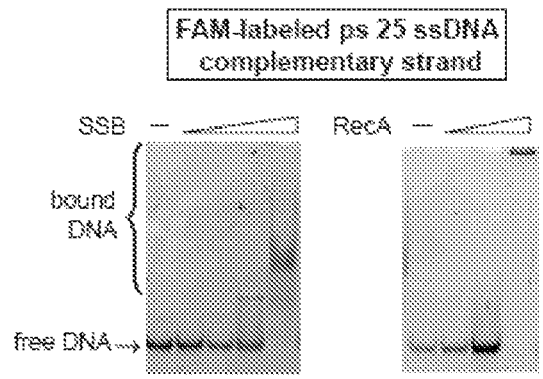

It has previously been demonstrated that natural transformation in *N. meningitidis* is subject to CRISPR interference, though these tests did not address the question of whether protospacer DNA targeting occurred during uptake, during or after recombination into the chromosome, or some combination of these. Zhang et al., 2013. To determine whether ssDNA bound by SSB or RecA can serve as a substrate for NmeCas9's tracrRNA-independent, crRNA guided cleavage activity, increasing amounts of purified SSB or RecA proteins were added to the cleavage reactions. See, FIGS. 9A and 9B, respectively. No inhibition of Cas9 cleavage was observed by a RecA protein at any concentration, and only modest inhibition of cleavage at the highest concentration of SSB. EMSA assays confirmed that the ssDNA substrate was bound by both SSB and RecA proteins under these conditions. See, FIGS. 9A-C, respectively.. These results suggest that tracrRNA-independent, crRNA-guided cleavage can proceed with substrates that more closely approximate the protein-bound ssDNAs thought to exist within cells.

VI. NmeCas9 PAM Specificity

Type I and II CRISPR/Cas systems generally have a protospacer adjacent motif (PAM) flanking the target region. Deveau et al., 2008; and Mojica et al., 2009. PAMs for Cas9 endonucleases are usually short (i.e., for example, approximately 2-5 nt) and located 3' of the target relative to the non-complementary strand, while the PAM sequences and lengths vary among Cas9 orthologues. Deveau et al., 2008; Gasiunas et al., 2012; Jinek et al., 2012; Esvelt et al., 2013; Zhang et al., 2013; Chen et al., 2014; Fonfara et al., 2014; and Ran et al., 2015. Previously, bioinformatics was used to define a PAM for NmeCas9 as 5'-NNNNGATT-3' (SEQ ID NO: 3) and showed that a double mutation in the middle of the PAM (GATT (SEQ ID NO: 17) to GTAT (SEQ ID NO: 18)) abolishes interference during *Neisseria* transformation. See, FIG. 3B; and Zhang et al., 2013. A single A to C mutation (GATT (SEQ ID NO: 17) to GCTT (SEQ ID NO: 19)) is also well-tolerated for a NmeCas9-mediated genome editing in human ES cells. Hou et al., 2013. Furthermore, a library depletion experiment in *E. coli* indicated that the NmeCas9 PAM has a very strong preference for guanine at the first position. Esvelt et al., 2013.

To understand better the rules governing NmeCas9 PAM specificity for target cleavage, a series of variant PAMs were engineered and tested using both in vitro and cellular approaches. First, each nucleotide base (e.g., each single nt) of the GATT PAM (SEQ ID NO: 17) was mutated to its Watson-Crick complement in the context of a ps 9 plasmid, and assayed plasmid cleavage by NmeCas9 in vitro. The 2A to 2T and 4T to 4A mutations were readily cleaved (like the wild-type PAM), while the 1G to 1C and 3T to 3A mutations abolished cleavage. See, FIG. 10A. The 2Δ3T to 2T3A partial cleavage defect is in agreement with the loss of cellular interference observed previously with the GTAT (SEQ ID NO: 18) mutant PAM, indicating that the in vitro and cellular results are consistent. Zhang et al., 2013.

A cellular transformation interference assay was then performed to study 1 nt PAM variants in the context of ps 25. Twelve single-nt variants were created in a GATT PAM (SEQ ID NO: 17), and the ability of each mutant to license CRISPR interference was tested in MC8013 cells during natural transformation, as described previously. Zhang et al., 2013. The data show that a ps25 plasmid with a wild-type PAM elicited interference, as reflected by the complete loss of transformants compared to the empty plasmid. See, FIG. 10B, upper panel. All three variants at the first guanine of the PAM led to major interference defects. In contrast, eight of the nine single-nt mutations in the other three PAM nts were permissive for interference. Only the T to A mutation at position 3 exhibited a modest defect, See, FIG. 10B, upper panel. These results are largely consistent with the in vitro cleavage assay. See, FIG. 10A. Collectively, these data suggest that NmeCas9 has a stringent preference for the guanine within the GATT PAM (SEQ ID NO: 17), and a high degree of tolerance for most single-nt variants at the 2nd, 3rd and 4th PAM positions. The same series of PAM variants in the context of a different protospacer (ps 24) yielded very similar results. See, FIG. 11. Consequently, it appears that NmeCas9 has a strong preference for a guanine at the first position, as well as tolerance of different nts at other PAM positions in bacteria which are not spacer context-dependent.

Although the guanine in the GATT PAM (SEQ ID NO: 17) clearly plays a role, additional testing revealed some dependence on the other positions. For example, twenty-seven (27) possible 2 nt variants were constructed in the other three PAM nts, and assayed for their abilities to license CRISPR interference of transformation in N. meningitidis. Interestingly, two-thirds (18/27) of these 2 nt variants exhibited intermediate to severe interference defects. See, FIG. 10B, lower panel. In contrast, 6/27 (GCCT, GTTA, GACC, GTCT, GCTA and GACG) double mutants were fully functional, and three more (GTTG, GACA, GAGA) exhibited a partial decrease in transformation efficiency. See, FIG. 10B, lower panel. All three representative triple mutants (e.g., GGGG, GTAA, and GCCC) displayed severe defects. See, FIG. 10B, lower panel.

Figure 12:
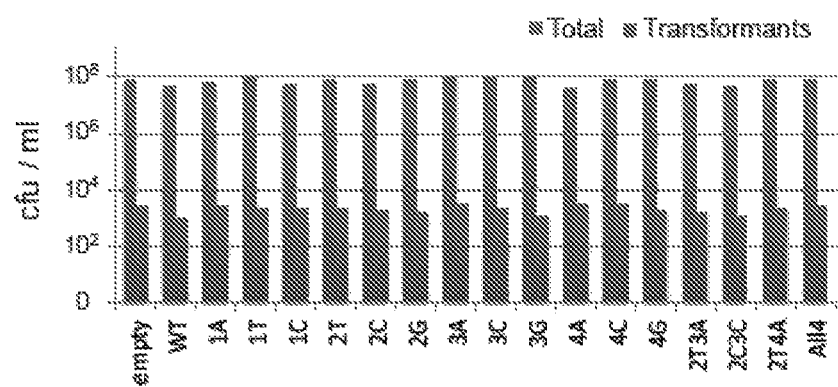
FIG. 12 presents exemplary data showing that interference defects for PAM variants are not due to deficiencies in natural transformation. Single-nt PAM variants and selected two-nt PAM variants of PYZEJS040 derivatives were analyzed by natural transformation assay using an interference-defective strain of MC8013 (cas9::Tn) as the recipient. Zhang et al., 2013. In the absence of CRISPR interference, all pYZEJS040 derivatives tested were as efficiently transformed as the empty vector. Experiments were done twice with similar results, and the data shown here are from one representative experiment.

The data show that ps25 plasmids with single-nt PAM mutants, as well as plasmids with representative double mutants and the quadruple mutant, efficiently transformed an isogenic strain carrying a transposon disruption of Cas9 indicating that the PAM variations affect interference, not transformation itself. See, FIG. 12; and Zhang et al., 2013. Previously, the functional PAM specificities derived from a library depletion approach proved to be complex (GANN, GTTN, GNNT>GTNN, GNTN) (Esvelt et al., 2013). Our individual tests help to reinforce most of these previously defined PAM specificities and also reveal further complexities, as some PAM variants that match one of those motifs (e.g. GAAG, GAAC, and GAGC) are completely defective.

Extensive biochemical and structural studies of SpyCas9 revealed unequivocally that its PAM consensus is required only on the crRNA-noncomplementary strand of duplex DNA targets. Jinek et al., 2012; Anders et al., 2014; and Sternberg et al., 2014. To address the strand specificity of PAM recognition by NmeCas9, an oligonucleotide cleavage assay was used to test three DNA duplexes where all 4 nts of the PAM were mutated in either the complementary strand, the non-complementary strand, or both. The 35 nt product for non-complementary strand cleavage disappeared when the PAM was disrupted on either target strand, or on both. Similarly, the 25 nt product of complementary strand cleavage was abolished or greatly diminished by mutations in the PAM on either target strand, or on both. See, FIG. 10C. These observations demonstrated that, unlike SpyCas9, NmeCas9 requires a PAM element on both strands of the duplex DNA substrates, or that recognition elements on one strand or the other can only be engaged in the context of a base-paired configuration.

To address the PAM requirement for ssDNA target recognition, ssDNA oligonucleotide cleavage was compared using two fluorescent ssDNA substrates, one with a wild-type PAM and the other with no PAM. The "No PAM" substrate was cleaved as efficiently by NmeCas9 as the wild-type counterpart, regardless of whether the tracrRNA is present. See, FIG. 10D. This observation suggests that the PAM is not necessary for NmeCas9-mediated ssDNA cleavage, in line with previous reports for SpyCas9 and SthCas9. Gasiunas et al., 2012; Jinek et al., 2012; and Nishimasu et al., 2014.

VII. Limited Tolerance for NmeCas9 Protospacer/PAM Linker Length Variation

For most of the type II CRISPR-Cas systems in which the PAM has been defined, a short (i.e., for example, approximately 1-4 nts), non-conserved linker separates a PAM and an adjacent protospacer. Deveau et al., 2008; Gasiunas et al., 2012; Jinek et al., 2012; Esvelt et al., 2013; Zhang et al., 2013; Chen et al., 2014; Fonfara et al., 2014; and Ran et al., 2015. The actual length of this linker varies among individual Cas9 orthologs. So far there have been only two examples of in vivo linker length flexibility: i) Sth1 Cas9 of strain DGCC7710 (Briner et al., 2014; Ran et al., 2015); and ii) SthCas9 of strain LMG18311 (Chen et al., 2014). Each of these strains can tolerate linker length extensions from 2 nt to 3 nt.

NmeCas9 was then tested for tolerance of linker length variations during interference in N. meningitidis cells. First, a potential target for spacer 23 of MC8013 was constructed in which the PAM and protospacer 23 were separated by a 4 nt "ATAT" linker. See, FIG. 13A, right panel. This construct was verified as fully functional in CRISPR interference using the natural transformation assay. See, FIG. 13A, left panel, LK4. Then the alternating A/T linker region was shortened or extended to separate a PAM sequence from a protospacer by 1 to 8 nts. See, FIG. 13A, right panel. Because the first nt of the GATT PAM (SEQ ID NO: 17) plays a role in targeting, the lack of guanine in the linker ensure that the linker variants are all deprived of any potential functional PAM variants. Mutant plasmids (e.g., for example, LK1-3, LK5-8) transformed the cells as efficiently as the empty plasmid, indicating that they were unable to elicit NmeCas9-mediated CRISPR interference. See, FIG. 13A, left panel. These data suggest that cellular interference by NmeCas9 performs efficiently with a 4 nt linker.

To determine whether linker length variations affect in vitro plasmid cleavage by NmeCas9, a set of linker mutant plasmids were analyzed. The wild-type 4 nt linker allowed efficient plasmid linearization, as did a 5 nt linker. See, FIG. 13B. The remaining linker mutants permitted only weak (e.g., 3 and 6 nts) or background (e.g., 1, 2, 7, 8 nts) cleavage. See, FIG. 13B. These observations suggest that an optimal 4 nt linker length observed during cellular interference is not an intrinsic feature of NmeCas9's target recognition activity in vitro.

Cas9 endonucleases induce mostly blunt-ended double-strand breaks between the 3rd and 4th base pairs at a PAM-proximal end of protospacers. Garneau et al., 2010; Gasiunas et al., 2012; Jinek et al., 2012; Hou et al., 2013; Chen et al., 2014; Fonfara et al., 2014; and Ran et al., 2015; See also, FIG. 3D. Type II-A SthCas9 from strain LMG18311 showed that its HNH and RuvC nuclease domains use different mechanisms to determine their cleavage sites on the two DNA strands: i) an RuvC domain cut is measured from a PAM; and ii) an HNH domain cut is at a fixed position within the protospacer without reference to a PAM. Chen et al., 2014. To determine whether the Type II-C NmeCas9 employs a similar mechanism, cleavage sites were mapped with strand-specific, end-labelled, oligonucleotide substrates bearing ps25 and its GATT PAM (SEQ ID NO: 17), separated by different linker lengths (e.g., between approximately 2-6 bp). When the label was on the non-complementary strand, thereby allowing RuvC domain activity to be assessed, NmeCas9 efficiently cleaved a 4 bp linker substrate to generate a 35 nt product. Although NmeCas9 cleavage efficiency was much lower with the other variant linker length substrates, the RuvC cleavage site moved in concert. See, FIG. 13C. These results revealed that a RuvC domain of NmeCas9 determines the cleavage site on the non-complementary strand by a "ruler" mechanism, cutting primarily between the 7th and 8th nts 5' of the GATT PAM (SEQ ID NO: 17).

To study the HNH domain of NmeCas9, radiolabeled, single-stranded DNA oligonucleotides corresponding to the complementary strand of sp 25 targets were used as substrates. Five ssDNA molecules with 2-6 nt linkers were tested in NmeCas9 cleavage reactions, with or without tracrRNA. For the dual RNA-mediated reactions, the most prominent products are consistently 25 nt, suggesting that neither extending (e.g., approximately 5 and/or 6 nts) nor shortening (e.g., approximately 2 and/or 3 nts) of the 4-nt linker altered the cleavage site selected by the HNH domain. The same holds true for a tracrRNA-independent mode of ssDNA cleavage, since the most dominant products were consistently 24 nt for all different substrates.

Also observed were several smaller-sized products, potentially reflecting minor cleavage events occurring 5' of the predominant NmeCas9 cleavage sites. Furthermore, as the length of the linker increased, the sizes of these minor products decreased accordingly. See, FIG. 13D.

VIII. Targeting by NmeCas9 has Relaxed Stringency for Complementarity within the Cleavage Site Both In Vitro and in Bacteria SpyCas9 requires near-perfect complementarity to the cleavage site (e.g., for example, an ~7-12 PAM-proximal bps of a protospacer) for CRISPR interference and efficient genome editing. Jinek et al., 2012; Cho et al., 2013; Cong et al., 2013; Hwang et al., 2013; Jiang et al., 2013; Jinek et al., 2013; and Mali et al., 2013. Previous studies of NmeCas9 targets showed that a 2 nt mismatch at the cleavage site of a protospacer abrogated interference, while a 2 nt mismatch further from the PAM (outside the cleavage site) did not abrogate interference. Zhang et al., 2013. Perfect cleavage site complementarity was suggested when studying NmeCas9-catalyzed genome editing in human ES cells. Hou et al., 2013.

Figure 14C:
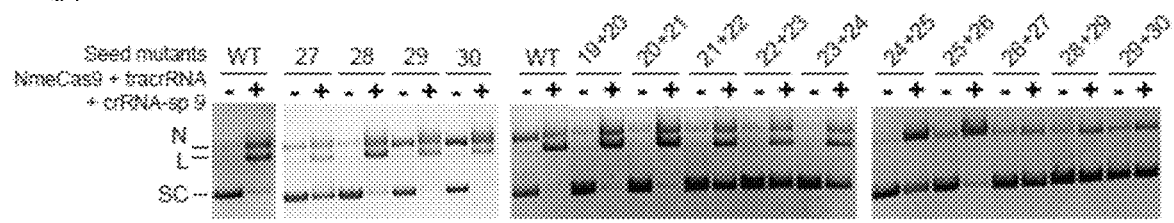
FIG. 14C: NmeCas9 tolerates many 1-nt but not 2-nt mismatches in the cleavage site in vitro. Representatives of the plasmids tested in FIG. 15B were analyzed in vitro by a plasmid cleavage assay using NmeCas9, sp 9 crRNA, and tracrRNA. N, nicked; L, linearized; SC: supercoiled.

To understand better NmeCas9 targeting requirements at the cleavage site, serial, single nt, protospacer mutations were created in a 12 nt cleavage site using a previously validated target for spacer 9 of MC8013. See, FIG. 14A. Plasmids containing these cleavage site mutant protospacers were transformed into N. meningitidis cells and assayed for CRISPR interference. Unexpectedly, the majority (11/12) of these cleavage site mutations had minimal impact on interference, while only one cleavage site mutation (e.g., in the fourth bp, counting from the PAM-proximal end) exhibited an intermediate interference defect. See, FIG. 14B, upper panel.

This same set of mutant plasmids was also subjected to in vitro NmeCas9 cleavage analysis. Corroborating the in vivo results, a cleavage site mutation at the fourth bp of the protospacer led to a significant cleavage defect. See, FIG. 14C, "27". To further investigate cleavage site requirements, eleven double mutants of the same protospacer were constructed and tested by both the natural transformation assay and in vitro plasmid cleavage. These double mutants each carry 2 nt consecutive mismatches in the cleavage site. See, FIG. 14A. A majority (8/11) of these mutants resulted in a loss of interference during transformation and defective plasmid cleavage. See, FIG. 14B, lower panel; and FIG. 14C, respectively. Analogous transformation experiments in a context of a different protospacer (e.g., ps 25 of MC8013) yielded similar results. See, FIG. 15.

Taken together, the above results suggest that NmeCas9 cleavage site requirements are somewhat relaxed in N. meningitidis cells and in vitro compared to the cleavage site requirements observed during genome editing in mammalian cells. Hou et al., 2013.

IX. Functional Anatomy Of NmeCas9's RNA Guides

An sgRNA, which is an engineered, chimeric fusion of mature crRNA and tracrRNA, is capable of directing Cas9 catalyzed programmable DNA cleavage and genome editing. Jinek et al., 2012; Cho et al., 2013; Cong et al., 2013; Hwang et al., 2013; Jiang et al., 2013; Jinek et al., 2013; and Mali et al., 2013. Previous reports in human ES and iPS cells showed that an sgRNA works as efficiently as dual crRNA and tracrRNA in NmeCas9-directed genome editing. Hou et al., 2013. To further dissect sgRNA structural and sequence requirements for NmeCas9, it was first established that sgRNA functions in vitro and then a series of 3'-terminal and internal sgRNA deletions were analyzed. See, FIG. 16A. A full-length 145-nt sgRNA, corresponding to sp 9 of MC8013), directed sequence-specific NmeCas9-catalyzed plasmid cleavage, with efficiency comparable to a parallel reaction with separate crRNA and tracrRNA. See, FIG. 16B, 3 left-most lanes).

A recent report established six structural modules—spacer, lower stem, bulge, upper stem, nexus, and the hairpins—within the sgRNAs for SpyCas9 and other type II-A systems. Briner et al., 2014. An sgRNA for NmeCas9 contains equivalents of these features. To begin defining these features in a type II-C system, serial sgRNA deletions were created with 7, 14, 22, 45, 57, and 69 nts removed from the 3' end of the RNA and tested their plasmid cleavage activities in vitro. See, FIG. 16A. The Δ7 nt substrate showed no NmeCas9 cleavage defects and the Δ14 nt and Δ22 nt RNAs exhibited modest cleavage defects, whereas the Δ45 nt, Δ57 nt and Δ69 nt sgRNAs were completely defective. See, FIG. 16B. These results suggest that the 3' terminal 7 nts are dispensable for cleavage, partial or total disruption (Δ14 nt, Δ22 nt) of the terminal hairpin modestly impedes NmeCas9 function, and complete removal (Δ45 nt, Δ57 nt and Δ69 nt) of the hairpin, or nexus plus the hairpin, abolishes NmeCas9 cleavage.

To further define sub-regions of NmeCas9 sgRNA that are internally required for targeting, sgRNA variants were generated with most of the nexus (e.g., int 2) or upper stem (e.g., int 1) deleted. See, FIG. 16A. Severe NmeCas9 cleavage defects were observed for the nexus deletion (e.g., int 2), whereas no defects were detected for the upper stem deletion (e.g., int1). FIG. 16B. This result shows that the nexus of the NmeCas9 sgRNA plays a role in NmeCas9 function, while the upper stem is dispensable, similar to the type II-A systems. Briner et al., 2014.

To determine whether the same modular requirements apply during cellular interference, a "clean" strain was created by deleting the crispr and tracrRNA loci from the chromosome, both of which play a role in transformation interference. See, FIG. 16C, FIG. 16D; and Zhang et al. 2013. A sp 25-specific full-length sgRNA under the control of the native tracrRNA promoter was then constructed in the pGCC2 plasmid and integrated into the chromosomal nics locus in the ΔcrisprΔtracr strain background. See, FIG. 16C. This sgRNA complementation restored CRISPR interference against a protospacer 25-containing plasmid during natural transformation, whereas control complementation using the empty pGCC2 vector in the nics locus did not. See, FIG. 16D. These data indicate that expressing the full-length sgRNA fully compensates for the loss of both cognate crRNA and tracrRNA in *N. meningitidis* cells. 3' truncations and internal deletions parallel to those analyzed in vitro in FIG. 16B were created in this cellular context, and their abilities to restore CRISPR interference were assayed in the ΔcrisprΔtracr mutant. Among all the variants tested, only two (e.g., Δ7 nt and int1) exhibited full rescue of CRISPR interference, suggesting that in vivo, NmeCas9 is only tolerant of small 3' terminal deletions or the removal of the upper stem, but not to the other deletions or truncations during transformation.

Figure 16D:
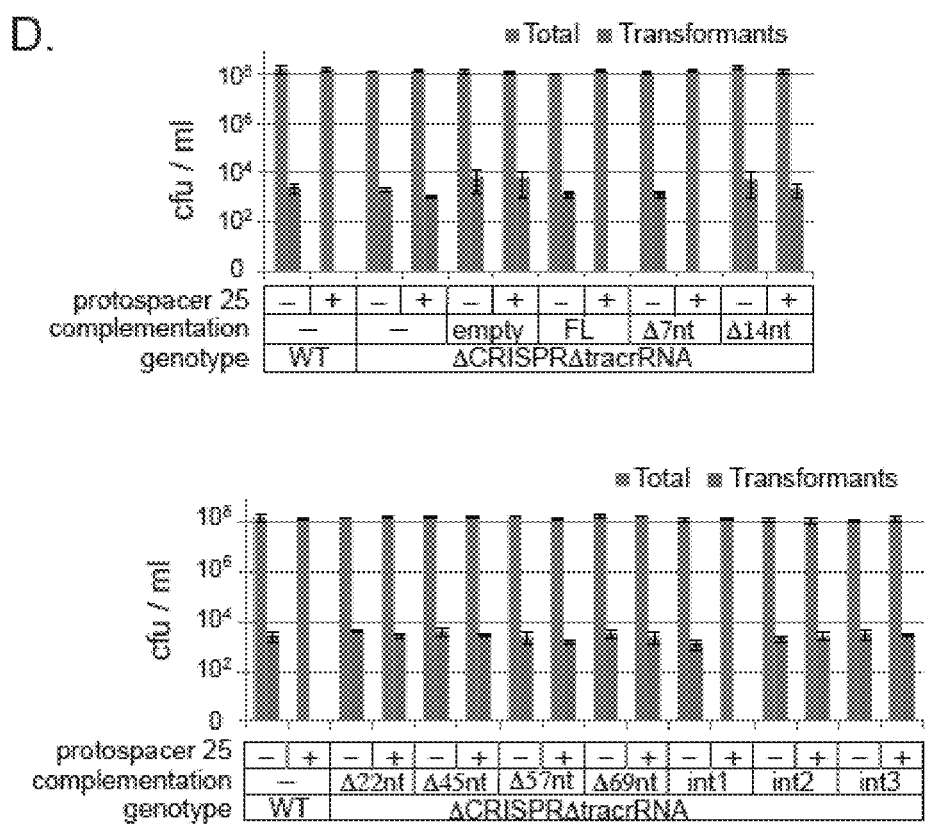
FIG. 16D: Definition of sgRNA regions that are required for transformation interference. pYZEJS040 (−) and its ps 25-containing derivative (+) were introduced into MC8013-derived strains by natural transformation. Relevant genotypes and sgRNA complementation variants are indicated at the bottom.

See, FIG. 16D. The GAAA tetraloop inserted to connect the crRNA and tracrRNA was retained in the int1 variant, and further deletion of this tetraloop from int1 that generates int3 and abolishes sgRNA function. See, FIG. 16A and FIG. 16D, respectively. These results suggest that the structure of the bulge region plays a role in function, since forcing it to comprise a terminal loop results in a non-functional sgRNA.

X. NmeCas9 PAM And Cleavage Site Specificity

Successful dsDNA targeting by type II CRISPR-Cas systems involves not only crRNA/protospacer complementarity, but also the presence of a PAM in the target. The well-characterized SpyCas9 requires a consensus NGG PAM (SEQ ID NO: 8) in both bacterial and eukaryotic cells, although the less optimal NAG (SEQ ID NO: 9) variant could also function. Hsu et al., 2013; Jiang et al., 2013; and Zhang et al., 2014. In some embodiments, the present invention contemplates that NmeCas9 has a strong preference for G at the first position of the GATT PAM (SEQ ID NO: 17), both in its native cellular environment and in vitro, corroborating findings from an earlier study of orthogonal Cas9s using *E. coli* as a surrogate. Esvelt et al., 2013. For non-guanosine PAM residues, comprehensive mutagenesis in *Neisseria* cells was carried out where functional PAM variants were identified that carry 1 nt or 2 nt deviations from a consensus GATT PAM (SEQ ID NO: 17). Some variants fit one of the minimal consensus PAMs defined previously yet were non-functional, indicating that PAM recognition rules may be even more complex than previously thought, and illustrating the value of deconvoluting the specificities defined by library depletion experiments. Esvelt et al., 2013. A previous study of NmeCas9-mediated genome editing in human ES and iPS cells only identified one functional PAM variant (GCTT) (SEQ ID NO: 19) in this biological context. (Hou et al., 2013).

The actual sequences and lengths of PAMs vary among different type II systems. Deveau et al., 2008; Gasiunas et al., 2012; Jinek et al., 2012; Esvelt et al., 2013; Zhang et al., 2013; Chen et al., 2014; Fonfara et al., 2014; and Ran et al., 2015. A subset of Cas9 orthologs, including but not limited to, *S. pyogenes, S. mutants, S. thermophilus* and *N. meningitidis*, use PAMs that begin with one or two guanosines. Deveau et al., 2008; Jinek et al., 2012; Zhang et al., 2013; Chen et al., 2014; and Fonfara et al., 2014. SthCas9 from LMG18311 requires a GYAAA PAM (SEQ ID NO: 20) and, like NmeCas9, tolerates single-nt PAM mutations in all positions except for a first G. Chen et al., 2014. However, effects of 2-nt (or more) variants from this PAM consensus were not defined. Structural analyses showed that SpyCas9 uses two conserved arginine residues to recognize the two guanosines in the GG PAM. Anders et al., 2014. These two arginines are not well conserved in Cas9s from many type II-C and some type II-A systems.

A surprising degree of insensitivity was observed regarding cleavage site mismatches during natural transformation, in stark contrast to the stringent requirement for cleavage site complementarity during NmeCas9-mediated mammalian genome editing. Hou et al., 2013. For example, with SpyCas9, single cleavage site mismatches disrupt transformation interference by the native CRISPR-Cas system, though much greater cleavage site mismatch tolerance was observed with SpyCas9 in vitro, especially at elevated enzyme concentrations. Jinek et al., 2012; and Pattanayak et al., 2013. This latter observation, along with the stringent requirement for cleavage site pairing in human cells (Hou et al., 2013), suggests that bacterial mismatch tolerance observed herein could reflect cellular NmeCas9 expression levels rather than a greater intrinsic nonspecificity of the enzyme.

XI. TracrRNA-Independent DNase H Activity Of NmeCas9

Until the present invention, the art considered that tracrRNA, or a tracrRNA-derived portion of an sgRNA was an essential component for Cas9 activity. Bernick et al., 2012; Barrangou and Marraffini, 2014; Doudna and Charpentier, 2014; Hsu et al., 2014; van der Oost et al., 2014; and Sontheimer and Barrangou, 2015. The tracrRNA-equivalent part of an sgRNA base-pairs with the crRNA repeat, forms multiple 3' hairpins, and is contacted extensively by Spy-Cas9, as revealed by recent structural reports. Anders et al., 2014; Nishimasu et al., 2014; and Jiang et al., 2015. The tracrRNA also contains a "nexus" stem-loop that imparts specificity and enforces orthogonality among Cas9/tracrRNA pairs. Briner et al., 2014.

Figure 8:
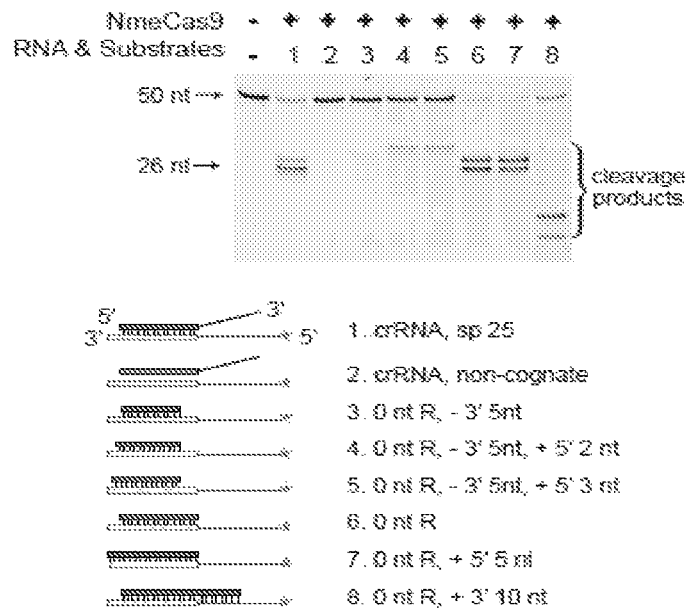
FIG. 8 presents exemplary data showing guide sequence independence and cleavage site selection for NmeCas9's DNase H activity.
Figure 8:
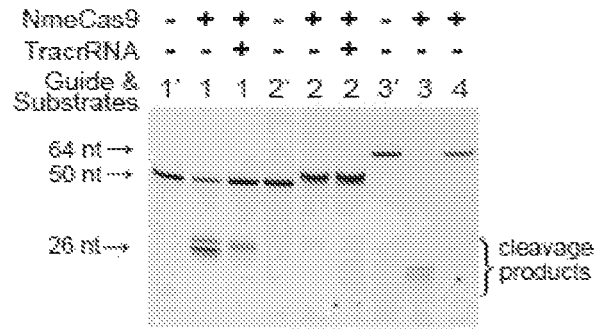
Figure 8:
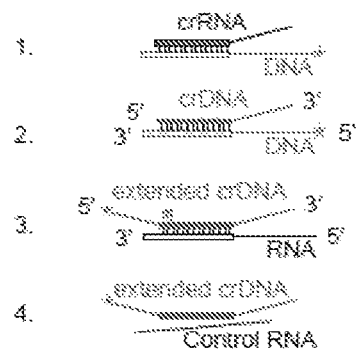

In one embodiment, the present invention contemplates an NmeCas9 that cleaves ssDNA molecules efficiently in the absence of a tracrRNA. See, FIG. 6 and FIG. 8. Compared to the cut sites observed for dual-RNA- or sgRNA-programmed Cas9 reactions, the predominant cut site for the DNase H activity is shifted 1 nt towards the PAM-proximal end of the protospacer, although additional, secondary cuts are also observed. Overall, NmeCas9-directed ssDNA cleavage appears to be as efficient as cleavage of dsDNAs (plasmids or oligonucleotide duplexes). See, FIGS. 3, 6 and 8. These observations are in stark contrast to other Cas9 orthologs biochemically characterized to date. For the well-characterized SpyCas9 and Sth3Cas9, ssDNA cleavage is much less efficient than dsDNA cleavage. Gasiunas et al., 2012; Jinek et al., 2012; and Sternberg et al., 2014.

Structural analyses provide hints of a possible enzymatic basis for tracrRNA-independent DNase H activity herein observed for NmeCas9. The structure of NmeCas9 is not known, and the only Type II-C Cas9 to be structurally characterized is AnaCas9, and this data in the apo form only (i.e. without bound guides or targets). Jinek et al., 2014. In contrast, crystal structures of SpyCas9 have been solved in the apo state (Jinek et al., 2014), with bound sgRNA (Jiang et al., 2015), and with sgRNA recognizing a fully single-stranded (Nishimasu et al., 2014) or partially double-stranded (Anders et al., 2014) DNA target. Collectively, these crystal structures reveal that the apo enzyme is found in an unproductive conformation and that sgRNA binding to SpyCas9 induces extensive domain movements (including the HNH domain) that lead to catalytic activation. The HNH domain of apo-SpyCas9 faces outwards away from the body of the nuclease lobe, and it appears to be autoinhibited, in addition to being poorly ordered in the crystal. Jinek et al., 2014. Although the HNH domain of apo-AnaCas9 is located in an equivalent position to that of apo-SpyCas9, it has fewer contacts with the C-terminal domain and it is more ordered. In the SpyCas9 complex structures the guide/target heteroduplex is trapped in a tunnel formed by the RuvC, HNH and REC domains, at the interface between the two lobes of the protein. Anders et al., 2014; and Nishimasu et al., 2014. Furthermore, residues in the tunnel do not interact with any of the tracrRNA regions in the sgRNA/SpyCas9 structures, suggesting that an RNA/DNA hybrid stem could easily be recognized and accommodated by NmeCas9 even in the absence of tracrRNA and positioned in a manner such that the HNH domain can engage the DNA strand. Anders et al., 2014; Nishimasu et al., 2014; and Jiang et al., 2015. Given the flexibility of the HNH domain, it is not surprising that the cleavage location is slightly shifted in the absence of tracrRNA, as probably many of the interactions needed to properly position the DNA in the active sites are absent. Finally, the absence of tracrRNA results in the cleavage of only ssDNA and not dsDNA. Nonetheless, the known flexibility of the HNH domains and the absence of the PAM-interacting CTD insertion, together with the largely modular nature of the interactions with crRNA and tracrRNA, could explain the observed NmeCas9 DNase H activity.

These unusual biochemical features of NmeCas9 are intriguing in light of known modes of genetic exchange in meningococci and many other bacteria. Natural transformation proceeds through the internalization of exogenous DNAs in single-stranded forms without strand preference, followed by integration into host chromosomes by homology-based recombination. Internalized ssDNAs are coated with RecA and ssDNA-binding proteins that facilitate homology searches along the bacterial chromosome in preparation for homologous recombination, and the data presented herein show that these proteins do not inhibit Cas9 activity in vitro. The heterologous sequences remain single-stranded in the recombination intermediates, and then become double stranded after chromosomal replication. Johnston et al., 2014.

It is not known which of these stages of transformation are subject to CRISPR interference, though fully recombined, genomic dsDNA is clearly susceptible, in keeping with Cas9's well-established capacity for genome editing. Bikard et al., 2012; Jiang et al., 2013; and Vercoe et al., 2013. In addition, either DNA strand can be randomly internalized during transformation, yet a crRNA that is complementary to only one strand completely blocks transformation. Bikard et al., 2012; and Zhang et al., 2013. This result indicates that targeting during the pre-recombination ssDNA phases, if it occurs, is not obligatory. Nonetheless, the data presented herein demonstrates that NmeCas9 can potentially target ssDNA regardless of whether tracrRNA availability provides a route toward sequence-specific transformation interference in a manner that does not require a lethal chromosome breakage event. The ability to target a chromosome in a tracrRNA-dependent manner would then enable any transformed "escapers" from earlier ssDNA-targeting phases to subject to a second round of restriction. It was previously found that a Δtracr strain exhibited a complete rather than partial loss of transformation interference, indicating that conditions under which tracrRNA-independent ssDNA interference could occur, if any, have yet to be identified. Zhang et al., 2013. In addition to transforming DNA, another potential natural ssDNA target could be the genomic ssDNA of filamentous phages, such as those reported previously in meningococci. Kawai et al., 2005.

The tracrRNA-independent nature of the NmeCas9 ssDNA cleaving activity is also intriguing, especially since little is known about the regulation of tracrRNA expression and whether there are contexts in which tracrRNA accumulation is downregulated. There are some strains of bacteria that contain Type II CRISPR-Cas loci without an annotated tracr locus, though this could simply reflect limitations in the ability to recognize and predict small RNA coding sequences from genomic data alone. Makarova et al., 2015. However, it is generally believed that Type II CRISPR-Cas loci has only a single tracrRNA transcription unit, whereas there are much larger numbers of CRISPR repeats (i.e., for example, up to 105 in a strain of *Mycoplasma* gallisepticum) in Type II pre-CRISPR RNAs. Accordingly, a complete use of a CRISPR locus' transcriptional output would require a substantial molar excess of tracrRNA, which could be challenging to generate, especially for large CRISPR loci. This problem could be exacerbated even further in the case of *N. meningitidis* (and at least some other Type II-C systems), because pre-crRNAs are generated from numerous promoters (e.g., one for each CRISPR repeat), potentially increasing the stoichiometric imbalance between the tracrRNA and the crRNA repeats. Zhang et al., 2013. Thus, it is straightforward to envision potential benefits of tracrRNA-independent functions, such as the RNA-guided ssDNA cleaving activity during interference with natural ssDNAs such as those that enter the cell during natural transformation.

In one embodiment, the present invention contemplates that NmeCas9 DNase H activity could provide a programmable, RNA-guided restriction enzyme that cleaves ssDNA. In one embodiment, the NmeCas9 lacks a tracrRNA sequence. Although it is not necessary to understand the mechanism of an invention, it is believed that when an RNA guide sequence is used in the absence of tracrRNA, NmeCas9 functions as a sequence-specific DNase with clear substrate preference in that NmeCas9 cuts ssDNA efficiently, but does not cut dsDNA. This unique feature distinguishes NmeCas9 from other Cas9 orthologs biochemically characterized to date as site-specific and ssDNA-specific DNases are uncommon in the art. This ssDNA-selective activity could also have utility within eukaryotic cells, for instance in destroying single-stranded regions of the genomes of certain DNA viruses such as Hepatitis B virus. Dienstag, 2008. In the absence of the tracrRNA, NmeCas9 could be used for such a purpose with little or no risk of collateral damage to the host cell's dsDNA genome.

XII. Pharmaceutical Compositions

The present invention further provides pharmaceutical compositions (e.g., comprising the compounds described above). The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient (s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

Agents that enhance uptake of oligonucleotides at the cellular level may also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on $EC_{50}s$ found to be effective in in vitro and in vivo animal models or based on the examples described herein. In general, dosage is from 0.01 µg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the compound is administered in maintenance doses, ranging from 0.01 µg to 100 g per kg of body weight, once or more daily, to once every 20 years.

XIII. Kits

In one embodiment, the present invention contemplates kits for the practice of the methods of this invention. The kits preferably include one or more containers containing a composition comprising a composition comprising a *Neisseria meningitidis* Cas9 (NmeCas9) enzyme and a guide RNA (gRNA) sequence, wherein the gRNA lacks a trans-activating CRISPR RNA (tracrRNA) sequence.; a second container comprising a gRNA sequence comprises a CRISPR RNA (crRNA) sequence and a set of instructions for administering the composition to a patient with a single stranded deoxyribonucleic acid virus infection. In one embodiment, the crRNA sequence comprises at least one complementary sequence to the viral single stranded deoxyribonucleic acid. The kit can optionally include additional containers having a composition comprising a gRNA sequence that is seventeen nucleotides. The kit can optionally include additional containers having a composition comprising a crRNA sequence with a mutated CRISPR repeat region. The kit can optionally include additional containers having a composition comprising a crRNA sequences that does not have a CRISPR repeat region.

The kit can optionally include enzymes capable of performing PCR (i.e., for example, DNA polymerase, Taq polymerase and/or restriction enzymes). The kit can optionally include a delivery vehicle for said vectors (e.g., a liposome). The reagents may be provided suspended in the excipient and/or delivery vehicle or may be provided as a separate component which can be later combined with the excipient and/or delivery vehicle. The kit may optionally contain additional therapeutics to be co-administered with the vectors to affect the desired transcriptional regulation.

The kits may also optionally include appropriate systems (e.g. opaque containers) or stabilizers (e.g. antioxidants) to prevent degradation of the reagents by light or other adverse conditions.

The kits may optionally include instructional materials. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXPERIMENTAL

The following examples are provided in order to demonstrate and further illustrate certain preferred embodiments and aspects of the present invention and are not to be construed as limiting the scope thereof.

Example I

Bacterial Strains, Plasmids and Oligonucleotides

*N. meningitidis* 8013 (MC8013), mutant derivatives plasmids and oligonucleotides are listed in the Tables below.

Meningococcal strains were grown on GC Medium Base (GCB) (Difco) plates with appropriate antibiotics and Kellogg's supplements I and II (Sigma). All solid cultures were incubated at 37° C. in a 5% $CO_2$ humidified atmosphere.

TABLE 3

Bacterial Strains

| Strain names | Relevant genotypes | Source |
|---|---|---|
| *N. meningitidis* 8013 | Wild type | Dr. Hank Seifert lab collection |
| | ΔcrisprΔtracr | This study |
| | ΔcrisprΔtracripGCC2 | This study |
| | ΔcrisprΔtracripGCC2-Sp25 sgRNA FL | This study |
| | ΔcrisprΔtracripGCC2-Sp25 sgRNA Δ7nt | This study |
| | ΔcrisprΔtracripGCC2-Sp25 sgRNA Δ14nt | This study |
| | ΔcrisprΔtracripGCC2-Sp25 sgRNA Δ22nt | This study |
| | ΔcrisprΔtracripGCC2-Sp25 sgRNA Δ45nt | This study |
| | ΔcrisprΔtracripGCC2-Sp25 sgRNA Δ57nt | This study |
| | ΔcrisprΔtracripGCC2-Sp25 sgRNA Δ69nt | This study |
| | ΔcrisprΔtracripGCC2-Sp25 sgRNA int1 | This study |
| | ΔcrisprΔtracripGCC2-Sp25 sgRNA int2 | This study |
| | ΔcrisprΔtracripGCC2-Sp25 sgRNA int3 | This study |
| | caz9::Tn | Zhang et al., 2013 |

TABLE 4

Plasmids

| Plasmids | Relevant characteristics | Source |
|---|---|---|
| Plasmids for creating the ΔcrisprΔtracr strain | | |
| pYZEJS067 | pSmartHC Amp/Δcrispr/SalI + SpeI | This study |
| pYZEJS068 | pSmartHC Amp/Δcrispr/CAT + rpsL | This study |
| Plasmids for creating the sgRNA complementation strains in ΔcrisprΔtracr background | | |
| pYZEJS001 | pGCC2 empty | Dr. Hank Seifert lab collection |
| pYZEJS079 | pGCC2/promoter + Sp25 sgRNA FL | This study |
| pYZEJS162 | pGCC2/promoter + Sp25 sgRNA Δ22nt | This study |
| pYZEJS163 | pGCC2/promoter + Sp25 sgRNA Δ45nt | This study |
| pYZEJS164 | pGCC2/promoter + Sp25 sgRNA Δ57nt | This study |
| pYZEJS165 | pGCC2/promoter + Sp25 sgRNA Δ69nt | This study |
| pYZEJS175 | pGCC2/promoter + Sp25 sgRNA Δ7nt | This study |
| pYZEJS176 | pGCC2/promoter + Sp25 sgRNA Δ14nt | This study |
| pYZEJS177 | pGCC2/promoter + Sp25 sgRNA int1 | This study |
| pYZEJS178 | pGCC2/promoter + Sp25 sgRNA int2 | This study |
| pYZEJS179 | pGCC2/promoter + Sp25 sgRNA int3 | This study |
| Plasmids for purification of NmeCas9 proteins | | |
| pYZEJS265 | pMCSG7/NmeCas9 wt | This study |
| pYZEJS266 | pMCSG7/NmeCas9 D16A | This study |
| pYZEJS267 | pMCSG7/NmeCas9 H588 | This study |
| pYZEJS268 | pMCSG7/NmeCas9 D16A + H588A (dm) | This study |
| Plasmids for cellular interference assays | | |
| pYZEJS040 | pSTblue-1/siaA + CAT + ctrA | Zhang et al., 2013 |
| pYZEJS101 | pYZEJS040-protospacer25 wt (short) | This study |
| pYZEJS102 | pYZEJS040-protospacer25 1A | This study |
| pYZEJS103 | pYZEJS040-protospacer25 1T | This study |
| pYZEJS104 | pYZEJS040-protospacer25 1C | This study |
| pYZEJS105 | pYZEJS040-protospacer25 2T | This study |
| pYZEJS106 | pYZEJS040-protospacer25 2C | This study |
| pYZEJS107 | pYZEJS040-protospacer25 2G | This study |
| pYZEJS108 | pYZEJS040-protospacer25 3A | This study |
| pYZEJS109 | pYZEJS040-protospacer25 3C | This study |
| pYZEJS110 | pYZEJS040-protospacer25 3G | This study |

TABLE 4-continued

Plasmids

| Plasmids | Relevant characteristics | Source |
|---|---|---|
| pYZEJS111 | pYZEJS040-protospacer25 4A | This study |
| pYZEJS112 | pYZEJS040-protospacer25 4C | This study |
| pYZEJS113 | pYZEJS040-protospacer25 4G | This study |
| pYZEJS114 | pYZEJS040-protospacer25 2T3A | This study |
| pYZEJS115 | pYZEJS040-protospacer25 1C2T3A4A | This study |
| pYZEJS116 | pYZEJS040-protospacer25 2C3C | This study |
| pYZEJS117 | pYZEJS040-protospacer25 2T4A | This study |
| pYZEJS118 | pYZEJS040-protospacer25 2C4C | This study |
| pYZEJS119 | pYZEJS040-protospacer25 3A4A | This study |
| pYZEJS120 | pYZEJS040-protospacer25 3C4C | This study |
| pYZEJS121 | pYZEJS040-protospacer25 2T3A4A | This study |
| pYZEJS122 | pYZEJS040-protospacer25 2C3C4C | This study |
| pYZEJS125 | pYZEJS040-protospacer25 2T3C | This study |
| pYZEJS126 | pYZEJS040-protospacer25 2T3G | This study |
| pYZEJS127 | pYZEJS040-protospacer25 2C3A | This study |
| pYZEJS128 | pYZEJS040-protospacer25 2C3G | This study |
| pYZEJS129 | pYZEJS040-protospacer25 2G3A | This study |
| pYZEJS130 | pYZEJS040-protospacer25 2G3C | This study |
| pYZEJS131 | pYZEJS040-protospacer25 2G3G | This study |
| pYZEJS132 | pYZEJS040-protospacer25 2T4C | This study |
| pYZEJS133 | pYZEJS040-protospacer25 2T4G | This study |
| pYZEJS134 | pYZEJS040-protospacer25 2C4A | This study |
| pYZEJS135 | pYZEJS040-protospacer25 2C4G | This study |
| pYZEJS136 | pYZEJS040-protospacer25 2G4A | This study |
| pYZEJS137 | pYZEJS040-protospacer25 2G4C | This study |
| pYZEJS138 | pYZEJS040-protospacer25 2G4G | This study |
| pYZEJS139 | pYZEJS040-protospacer25 3A4C | This study |
| pYZEJS140 | pYZEJS040-protospacer25 3A4G | This study |
| pYZEJS141 | pYZEJS040-protospacer25 3C4A | This study |
| pYZEJS142 | pYZEJS040-protospacer25 3C4G | This study |
| pYZEJS143 | pYZEJS040-protospacer25 3G4A | This study |
| pYZEJS144 | pYZEJS040-protospacer25 3G4C | This study |
| pYZEJS145 | pYZEJS040-protospacer25 3G4G | This study |
| pYZEJS146 | pYZEJS040-protospacer25 2G3G4G | This study |
| Plasmids for cellular interference and in vitro cleavage assays | | |
| pYZEJS241 | pYZEJS040-protospacer23-lk1 | This study |
| pYZEJS242 | pYZEJS040-protospacer23-lk2 | This study |
| pYZEJS243 | pYZEJS040-protospacer23-lk3 | This study |
| pYZEJS244 | pYZEJS040-protospacer23-lk4 | This study |
| pYZEJS245 | pYZEJS040-protospacer23-lk5 | This study |
| pYZEJS246 | pYZEJS040-protospacer23-lk6 | This study |
| pYZEJS247 | pYZEJS040-protospacer23-lk7 | This study |
| pYZEJS248 | pYZEJS040-protospacer23-lk8 | This study |
| Plasmids for cellular interference assays | | |
| pYZEJS070 | pYZEJS040-protospacer24 wt | This study |
| pYZEJS081 | pYZEJS040-protospacer24 1A | This study |
| pYZEJS082 | pYZEJS040-protospacer24 1T | This study |
| pYZEJS083 | pYZEJS040-protospacer24 1C | This study |
| pYZEJS084 | pYZEJS040-protospacer24 2T | This study |
| pYZEJS085 | pYZEJS040-protospacer24 2C | This study |
| pYZEJS086 | pYZEJS040-protospacer24 2G | This study |
| pYZEJS087 | pYZEJS040-protospacer24 3A | This study |
| pYZEJS088 | pYZEJS040-protospacer24 3C | This study |
| pYZEJS089 | pYZEJS040-protospacer24 3G | This study |
| pYZEJS090 | pYZEJS040-protospacer24 4A | This study |
| pYZEJS091 | pYZEJS040-protospacer24 4C | This study |
| pYZEJS092 | pYZEJS040-protospacer24 4G | This study |
| pYZEJS094 | pYZEJS040-protospacer24 1C2T3A4A | This study |
| Plasmids for in vitro cleavage, S1, S6 (also used in cellular interference assays | | |
| pYZEJS012 | pGCC2/protospacer 9 wt | Zhang et al., 2013 |
| pYZEJS095 | pGCC2/protospacer 9 1C | This study |
| pYZEJS096 | pGCC2/protospacer 9 2T | This study |
| pYZEJS097 | pGCC2/protospacer 9 3A | This study |
| pYZEJS098 | pGCC2/protospacer 9 4A | This study |
| pYZEJS023 | pGCC2/protospacer 9 2T3A | Zhang et al., 2013 |
| pYZEJS147 | pGCC2/protospacer 9 seed 19 | This study |
| pYZEJS148 | pGCC2/protospacer 9 seed 20 | This study |
| pYZEJS149 | pGCC2/protospacer 9 seed 21 | This study |
| pYZEJS150 | pGCC2/protospacer 9 seed 22 | This study |
| pYZEJS151 | pGCC2/protospacer 9 seed 23 | This study |
| pYZEJS152 | pGCC2/protospacer 9 seed 24 | This study |
| pYZEJS153 | pGCC2/protospacer 9 seed 25 | This study |
| pYZEJS154 | pGCC2/protospacer 9 seed 26 | This study |

TABLE 4-continued

Plasmids

| Plasmids | Relevant characteristics | Source |
|---|---|---|
| pYZEJS155 | pGCC2/protospacer 9 seed 27 | This study |
| pYZEJS156 | pGCC2/protospacer 9 seed 28 | This study |
| pYZEJS157 | pGCC2/protospacer 9 seed 29 | This study |
| pYZEJS158 | pGCC2/protospacer 9 seed 30 | This study |
| pYZEJS020 | pGCC2/protospacer 9 seed 15 + 16 | Zhang et al., 2013 |
| pYZEJS181 | pGCC2/protospacer 9 seed 19 + 20 | This study |
| pYZEJS182 | pGCC2/protospacer 9 seed 20 + 21 | This study |
| pYZEJS183 | pGCC2/protospacer 9 seed 21 + 22 | This study |
| pYZEJS184 | pGCC2/protospacer 9 seed 22 + 23 | This study |
| pYZEJS185 | pGCC2/protospacer 9 seed 23 + 24 | This study |
| pYZEJS186 | pGCC2/protospacer 9 seed 24 + 25 | This study |
| pYZEJS187 | pGCC2/protospacer 9 seed 25 + 26 | This study |
| pYZEJS188 | pGCC2/protospacer 9 seed 26 + 27 | This study |
| pYZEJS021 | pGCC2/protospacer 9 seed 27 + 28 | Zhang et al., 2013 |
| pYZEJS189 | pGCC2/protospacer 9 seed 28 + 29 | This study |
| pYZEJS190 | pGCC2/protospacer 9 seed 29 + 30 | This study |
| Plasmids for cellular interference assays | | |
| pYZEJS192 | pYZEJS040-protospacer25 seed 19 | This study |
| pYZEJS193 | pYZEJS040-protospacer25 seed 20 | This study |
| pYZEJS194 | pYZEJS040-protospacer25 seed 21 | This study |
| pYZEJS195 | pYZEJS040-protospacer25 seed 22 | This study |
| pYZEJS196 | pYZEJS040-protospacer25 seed 23 | This study |
| pYZEJS197 | pYZEJS040-protospacer25 seed 24 | This study |
| pYZEJS198 | pYZEJS040-protospacer25 seed 25 | This study |
| pYZEJS199 | pYZEJS040-protospacer25 seed 26 | This study |
| pYZEJS200 | pYZEJS040-protospacer25 seed 27 | This study |
| pYZEJS201 | pYZEJS040-protospacer25 seed 28 | This study |
| pYZEJS202 | pYZEJS040-protospacer25 seed 29 | This study |
| pYZEJS203 | pYZEJS040-protospacer25 seed 30 | This study |
| pYZEJS208 | pYZEJS040-protospacer25 seed 19 + 20 | This study |
| pYZEJS209 | pYZEJS040-protospacer25 seed 20 + 21 | This study |
| pYZEJS210 | pYZEJS040-protospacer25 seed 21 + 22 | This study |
| pYZEJS211 | pYZEJS040-protospacer25 seed 22 + 23 | This study |
| pYZEJS212 | pYZEJS040-protospacer25 seed 23 + 24 | This study |
| pYZEJS213 | pYZEJS040-protospacer25 seed 24 + 25 | This study |
| pYZEJS214 | pYZEJS040-protospacer25 seed 25 + 26 | This study |
| pYZEJS215 | pYZEJS040-protospacer25 seed 26 + 27 | This study |
| pYZEJS216 | pYZEJS040-protospacer25 seed 27 + 28 | This study |
| pYZEJS217 | pYZEJS040-protospacer25 seed 28 + 29 | This study |
| pYZEJS218 | pYZEJS040-protospacer25 seed 29 + 30 | This study |

Example 2

Mutant Strain Construction

Mutant strains were generated by transformation with appropriately constructed plasmids, and confirmed by PCR and DNA sequencing. The unmarked Δcrispr strain was created by a two-step transformation strategy as previously described for creating the unmarked Δcas9 strain. Dienstag, 2008. For generation of the ΔcrisprΔtracr strain, a Δcrispr strain was transformed with genomic DNA (gDNA) isolated from the Δtracr strain, followed by KanR selection. Zhang et al., 2013. For complementation of sgRNA variants, wt and variant copies of the sgRNA were cloned into pGCC2 and transformed the resulting plasmids into the ΔcrisprΔtracr strain.

Mutant strains were confirmed by PCR and DNA sequencing. To create the unmarked Δcrispr strain, a streptomycin-resistant (SmR) strain was transformed with plasmid pSmartHCAmp/Δcrispr/CAT-rpsL, in which a dual-marker cassette [CAT (chloramphenicol acetyltransferase, conferring chloramphenicol resistance) (CmR) and wild-type rpsL] replaced the crispr locus. The resulting SmS CmR transformants were transformed with plasmid pSmartH-CAmp/Δcrispr/SalI+SpeI. SmR CmS colonies were screened by PCR to confirm replacement of the dual marker cassette with the unmarked crispr deletion. To generate complementation strains expressing sgRNAs, sp 25 sgRNA variants were generated and cloned into plasmid pGCC2, transformed the resulting plasmids into the parental ΔcrisprΔtracr strain, and selected erythromycin-resistant (ErmR) transformants.

Example 3

Natural Transformation

Natural transformation assays were performed in MC8013 and mutant derivatives as previously described. Zhang et al., 2013. Antibiotic-resistant cfu/ml and total cfu/ml were reported from three independent experiments (mean+/−s.e.m.), except where noted.

Example 4

In Vitro Transcription

RNAs were generated by in vitro transcription using a MEGAscript T7 kit (Ambion) and gel purified. Transcription templates were gel-purified PCR products, linearized plasmids, or annealed DNA oligonucleotides carrying the T7 promoter sequence.

Example 5

Recombinant NmeCas9 Expression and Purification

NmeCas9 genes of MC8013 were cloned into the pMCSG7 vector using Ligation Independent Cloning. Stols et al., 2002. The resulting NmeCas9 protein contains an N-terminal His6-tag, followed by a Tobacco Etch Virus (TEV) protease site to remove the His-tag by TEV cleavage. For protein expression, the plasmid was transformed into BL21(DE3) Rosetta cells.

The cells were grown in terrific broth medium at 36° C. to an OD600 of ~0.8, transferred to ice to reduce the temperature to around 16° C., induced with 0.5 mM β-D-1-thiogalactopyranoside (IPTG), and grown overnight at 16° C. for protein expression. Cell pellets were re-suspended in re-suspension buffer (50 mM TRIS pH 8, 500 mM NaCl, 10% glycerol, and 5 mM imidazole) and stored at −80° C.

For purification, cells were thawed and protease inhibitors [Benzimidine (1 mM), Pepstatin (1 µg/ml), and PMSF (1 mM)] were added to the cell suspension. The cells were then incubated while sequentially adding Lysozyme (0.625 mg/ml), Brij58 (0.1%), and DNase (0.02 mg/mL, along with 10 mM MgCl2), with 30 minutes of gentle rocking at 4° C. for each step. This was followed by a gentle sonication of the cells.

The cell lysate was spun at 35,000 rpm for 30 minutes and the supernatant was filtered through a 0.2 µm filter. The salt concentration of the supernatant was adjusted to 1M NaCl, and 0.2% Polyethyleneimine (PEI) was added slowly to the supernatant while stirring at 4° C., for a total period of 30 minutes. The solution was spun at 18,000 rpm at 4° C. for 30 minutes, during which NmeCas9 separated into the supernatant. Solid ammonium sulfate was added to the supernatant to a final concentration of 50% (29.1 g for a 100 ml solution) and stirred at 4° C. for 30 minutes. The solution was spun at 18,000 rpm for 30 minutes and the majority of NmeCas9 settled in the pellet. The pellet was solubilized in Buffer A (re-suspension buffer supplemented with salt to a final 1 M NaCl concentration, along with 1 mM PMSF). The protein solution was loaded onto a Ni-NTA column that was equilibrated with the same buffer. After loading, the column was washed with around 500 mL of Buffer A to remove any unbound or loosely bound contaminating protein followed by 100 mL Buffer A supplemented with 20 mM Imidazole, and finally with Buffer A with 350 mM Imidazole to elute the protein.

Protein was dialyzed into S-column buffer (20 mM HEPES pH 7.5, 250 mM KCl, 10% glycerol, 1 mM DTT, and 1 mM PMSF) and simultaneously incubated with TEV protease [(1:50 (mg/ml)] to cleave the His-tag. The protein was passed through a Ni-NTA column to deplete the His-tag and the uncleaved NmeCas9. The flow-through from the Ni-NTA column was loaded onto a MonoS column and eluted by a salt gradient from 250 mM to 1.5 M KCl. The pure fractions were pooled and dialyzed into S200-column buffer (20 mM HEPES pH 7.5, 500 mM KCl, 10% glycerol, 1 mM DTT, and 1 mM PMSF). The protein was concentrated and loaded onto a gel filtration column (S200). Pure NmeCas9 protein fractions were pooled, concentrated to around 20 mg/ml, and stored at −80° C.

Example 6

Plasmid DNA Cleavage

Plasmid DNA (300 ng, ~9 nM) was incubated with NmeCas9 protein (50-500 nM) and preannealed crRNA:tracrRNA duplex (1:1, 50-500 nM) in standard cleavage buffer [20 mM HEPES (pH 7.5), 150 mM KCl, 10% glycerol, 1 mM DTT, and 10 mM MgCl2] at 37° C. for 5-30 min. Other divalent metals were also tested at 10 mM. The reactions were resolved by 0.6-1% agarose gels and visualized by ethidium bromide staining.

Example 7

Oligonucleotide Cleavage Assay 10 pmol of gel-purified DNA oligonucleotides (IDT) were 32P-labeled with T4 PNK (NEB) and [γ-32P]-ATP (PerkinElmer), and cleaned up by MicroBio Spin 6 columns (BioRad). Duplex DNA (100 nM) substrates were generated by annealing of equimolar amounts of two oligos. DNA oligonucleotides (IDT) [5-10 nM for 32P-labeled, or 25-50 nM for 6-carboxyfluorescein (FAM)-labeled oligos] were incubated with NmeCas9 proteins (500 nM) and pre-annealed crRNA:tracrRNA duplex (1:1, 500 nM) in standard cleavage buffer (described above) at 37° C. for 30 min. Reactions were resolved on 15% denaturing PAGE and visualized with a Phosphorimager or ImageQuant LAS 4000 imager. Reactions with 32P-labeled oligos were purified by phenol/chloroform extraction and ethanol precipitation before electrophoresis.

Example 8

Electrophoretic Mobility Shift Assay

FAM-labeled ssDNA oligonucleotides (IDT, 25-50 nM) were incubated with NmeCas9 (500 nM) and various small RNAs (500 nM) in standard cleavage buffer (without Mg2+) at room temperature for 8-10 min. The reactions were resolved by 6% Native PAGE at 4° C. and visualized by an ImageQuant LAS 4000 imager.

Example 9

Plasmid Construction

Plasmids used in this study are listed in accordance with Example I. *E. coli* Top10 competent cells (Invitrogen) were used for cloning. All plasmids were verified by DNA sequencing. Regular and overlapping PCRs for cloning were done using Platinum Pfx DNA Polymerase (Invitrogen). Protospacer plasmids (i.e., for example, pGCC2 or pYZEJS040 and their derivatives) for in vitro cleavage and *N. meningitidis* transformation assays were constructed as described previously. Zhang et al., 2013.

All PAM and cleavage site mutants of the protospacer plasmids were created by QuikChange (Agilent) mutagenesis. Plasmids for creating *N. meningitidis* ΔcrisprΔtracrRNA strains with sgRNA complementation were constructed by overlapping PCR or regular PCR and ligation as previously described. Zhang et al., 2013. The wild type NmeCas9 gene was cloned into the pMCSG7 vector to create the plasmid for overexpression of NmeCas9 protein, and derivative plasmids for mutant NmeCas9 proteins were constructed by QuikChange (Agilent) mutagenesis.

Example 10

Binding of SSB and RecA Proteins to ssDNA Substrates

FAM-labeled ssDNA oligonucleotide (IDT, Coralville Iowa) was incubated in standard cleavage buffer, with increasing concentrations of SSB (0.05, 0.5, 5, 50 ng/μL) or RecA (2, 20, 200 ng/μL) proteins (NEB) at 37° C. for 10 min. For cleavage assays, small RNAs (500 nM) and Nme-Cas9 (500 nM) were then added to the reaction, incubated at 37° C. for 30 min. For EMSAs, half of the binding reaction was supplied with 10% glycerol.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

REFERENCES

Anders, C., Niewoehner, O., Duerst, A., and Jinek, M. (2014). Structural basis of PAM-dependent target DNA recognition by the Cas9 endonuclease. Nature 513, 569-573.

Barrangou, R., Fremaux, C., Deveau, H., Richards, M., Boyaval, P., Moineau, S., Romero, D. A., and Horvath, P. (2007). CRISPR provides acquired resistance against viruses in prokaryotes. Science 315, 1709-1712.

Barrangou, R., and Marraffini, L. A. (2014). CRISPR-Cas systems: Prokaryotes upgrade to adaptive immunity. Mol. Cell 54, 234-244.

Bernick, D. L., Cox, C. L., Dennis, P. P., and Lowe, T. M. (2012). Comparative genomic and transcriptional analyses of CRISPR systems across the genus Pyrobaculum. Front Microbiol 3, 251.

Bikard, D., Hatoum-Aslan, A., Mucida, D., and Marraffini, L. A. (2012). CRISPR interference can prevent natural transformation and virulence acquisition during in vivo bacterial infection. Cell Host & Microbe 12, 177-186.

Bolotin, A., Quinquis, B., Sorokin, A., and Ehrlich, S. D. (2005). Clustered regularly interspaced short palindrome repeats (CRISPRs) have spacers of extrachromosomal origin. Microbiology 151, 2551-2561.

Briner, A. E., Donohoue, P. D., Gomaa, A. A., Selle, K., Slorach, E. M., Nye, C. H., Haurwitz, R. E., Beisel, C. L., May, A. P., and Barrangou, R. (2014). Guide RNA functional modules direct Cas9 activity and orthogonality. Mol. Cell 56, 333-339.

Brouns, S. J., Jore, M. M., Lundgren, M., Westra, E. R., Slijkhuis, R. J., Snijders, A. P.,
Dickman, M. J., Makarova, K. S., Koonin, E. V., and van der Oost, J. (2008). Small CRISPR RNAs guide antiviral defense in prokaryotes. Science 321, 960-964.

Chen, H., Choi, J., and Bailey, S. (2014). Cut site selection by the two nuclease domains of the Cas9 RNA-guided endonuclease. J. Biol. Chem. 289, 13284-13294.

Cho, S. W., Kim, S., Kim, J. M., and Kim, J. S. (2013). Targeted genome engineering in human cells with the Cas9 RNA-guided endonuclease. Nat. Biotechnol. 31, 230-232.

Cong, L., Ran, F. A., Cox, D., Lin, S., Barretto, R., Habib, N., Hsu, P. D., Wu, X., Jiang, W., Marraffini, L. A., et al. (2013). Multiplex genome engineering using CRISPR/Cas systems. Science 339, 819-823.

Deltcheva, E., Chylinski, K., Sharma, C. M., Gonzales, K., Chao, Y., Pirzada, Z. A., Eckert, M. R., Vogel, J., and Charpentier, E. (2011). CRISPR RNA maturation by trans-encoded small RNA and host factor RNase III. Nature 471, 602-607.

Deveau, H., Barrangou, R., Garneau, J. E., Labonte, J., Fremaux, C., Boyaval, P., Romero, D. A., Horvath, P., and Moineau, S. (2008). Phage response to CRISPR-encoded resistance in Streptococcus thermophilus. J. Bacteriol. 190, 1390-1400.

Dienstag, J. L. (2008). Hepatitis B virus infection. N. Engl. J. Med. 359, 1486-1500.

Doudna, J. A., and Charpentier, E. (2014). The new frontier of genome engineering with CRISPR-Cas9. Science 346, 1258096.

Esvelt, K. M., Mali, P., Braff, J. L., Moosburner, M., Yaung, S. J., and Church, G. M. (2013). Orthogonal Cas9 proteins for RNA-guided gene regulation and editing. Nat. Methods 10, 1116-1121.

Fonfara, I., Le Rhun, A., Chylinski, K., Makarova, K. S., Lecrivain, A. L., Bzdrenga, J., Koonin, E. V., and Charpentier, E. (2014). Phylogeny of Cas9 determines functional exchangeability of dual-RNA and Cas9 among orthologous type II CRISPR-Cas systems. Nucleic Acids Res. 42, 2577-2590.

Garneau, J. E., Dupuis, M. E., Villion, M., Romero, D. A., Barrangou, R., Boyaval, P., Fremaux, C., Horvath, P., Magadan, A. H., and Moineau, S. (2010). The CRISPR/Cas bacterial immune system cleaves bacteriophage and plasmid DNA. Nature 468, 67-71.

Gasiunas, G., Barrangou, R., Horvath, P., and Siksnys, V. (2012). Cas9-crRNA ribonucleoprotein complex mediates specific DNA cleavage for adaptive immunity in bacteria. Proc. Natl. Acad. Sci. USA 109, E2579-2586.

Gunderson, F. F., and Cianciotto, N. P. (2013). The CRISPR-associated gene cas2 of Legionella pneumophila is required for intracellular infection of amoebae. mBio 4, e00074-00013.

Hale, C., Kleppe, K., Terns, R. M., and Terns, M. P. (2008). Prokaryotic silencing (psi)RNAs in Pyrococcus furiosus. RNA 14, 2572-2579.

Hou, Z., Zhang, Y., Propson, N. E., Howden, S. E., Chu, L. F., Sontheimer, E. J., and Thomson, J. A. (2013). Efficient genome engineering in human pluripotent stem cells using Cas9 from Neisseria meningitidis. Proc. Natl. Acad. Sci. USA 110, 15644-15649.

Hsu, P. D., Lander, E. S., and Zhang, F. (2014). Development and applications of CRISPRCas9 for genome engineering. Cell 157, 1262-1278.

Hsu, P. D., Scott, D. A., Weinstein, J. A., Ran, F. A., Konermann, S., Agarwala, V., Li, Y., Fine, E. J., Wu, X., Shalem, O., et al. (2013). DNA targeting specificity of RNA-guided Cas9 nucleases. Nat. Biotechnol. 31, 827-832.

Hwang, W. Y., Fu, Y., Reyon, D., Maeder, M. L., Tsai, S. Q., Sander, J. D., Peterson, R. T., Yeh, J. R., and Joung, J. K. (2013). Efficient genome editing in zebrafish using a CRISPRCas system. Nat. Biotechnol. 31, 227-229.

Jiang, F., Zhou, K., Ma, L., Gressel, S., and Doudna, J. A. (2015). A Cas9-guide RNA complex preorganized for target DNA recognition. Science 348, 1477-1481.

Jiang, W., Bikard, D., Cox, D., Zhang, F., and Marraffini, L. A. (2013). RNA-guided editing of bacterial genomes using CRISPR-Cas systems. Nat. Biotechnol. 31, 233-239.

Jinek, M., Chylinski, K., Fonfara, I., Hauer, M., Doudna, J. A., and Charpentier, E. (2012). A programmable dual-RNA-guided DNA endonuclease in adaptive bacterial immunity. Science 337, 816-821.

Jinek, M., East, A., Cheng, A., Lin, S., Ma, E., and Doudna, J. (2013). RNA-programmed genome editing in human cells. eLife 2, e00471.

Jinek, M., Jiang, F., Taylor, D. W., Sternberg, S. H., Kaya, E., Ma, E., Anders, C., Hauer, M., Zhou, K., Lin, S., et al. (2014). Structures of Cas9 endonucleases reveal RNA-mediated conformational activation. Science 343, 1247997.

Johnston, C., Martin, B., Fichant, G., Polard, P., and Claverys, J. P. (2014). Bacterial transformation: distribution, shared mechanisms and divergent control. Nat. Rev. Microbiol. 12, 181-196.

Kawai, M., Uchiyama, I., and Kobayashi, I. (2005). Genome comparison in silico in Neisseria suggests integration of filamentous bacteriophages by their own transposase. DNA Res. 12, 389-401.

Kearns, N. A., Pham, H., Tabak, B., Genga, R. M., Silverstein, N. J., Garber, M., and Maehr, R. (2015). Functional annotation of native enhancers with a Cas9-histone demethylase fusion. Nat. Methods 12, 401-403.

Louwen, R., Horst-Kreft, D., de Boer, A. G., van der Graaf, L., de Knegt, G., Hamersma, M., Heikema, A. P., Timms, A. R., Jacobs, B. C., Wagenaar, J. A., et al. (2013). A novel link between Campylobacter jejuni bacteriophage defence, virulence and Guillain-Barre syndrome. Eur. J. Clin. Microbiol. Infect. Dis. 32, 207-226.

Makarova, K. S., Wolf, Y. I., Alkhnbashi, O. S., Costa, F., Shah, S. A., Saunders, S. J., Barrangou, R., Brouns, S. J. J., Charpentier, E., Haft, D. H., et al. (2015). An updated evolutionary classification scheme for CRISPR-Cas systems. Nat. Rev. Microbiol., in press.

Mali, P., Yang, L., Esvelt, K. M., Aach, J., Guell, M., DiCarlo, J. E., Norville, J. E., and Church, G. M. (2013). RNA-guided human genome engineering via Cas9. Science 339, 823-826. Marraffini, L. A., and Sontheimer, E. J. (2008). CRISPR interference limits horizontal gene transfer in staphylococci by targeting DNA. Science 322, 1843-1845.

Mojica, F. J., Diez-Villasenor, C., Garcia-Martinez, J., and Almendros, C. (2009). Short motif sequences determine the targets of the prokaryotic CRISPR defence system. Microbiology 155, 733-740.

Mojica, F. J., Diez-Villasenor, C., Garcia-Martinez, J., and Soria, E. (2005). Intervening sequences of regularly spaced prokaryotic repeats derive from foreign genetic elements. J. Mol. Evol. 60, 174-182.

Nishimasu, H., Ran, F. A., Hsu, P. D., Konermann, S., Shehata, S. I., Dohmae, N., Ishitani, R., Zhang, F., and Nureki, O. (2014). Crystal structure of Cas9 in complex with guide RNA and target DNA. Cell 156, 935-949.

Nunez, J. K., Kranzusch, P. J., Noeske, J., Wright, A. V., Davies, C. W., and Doudna, J. A. (2014). Cas1-Cas2 complex formation mediates spacer acquisition during CRISPR-Cas adaptive immunity. Nat. Struct. Mol. Biol. 21, 528-534.

Nunez, J. K., Lee, A. S., Engelman, A., and Doudna, J. A. (2015). Integrase-mediated spacer acquisition during CRISPR-Cas adaptive immunity. Nature 519, 193-198.

Pattanayak, V., Lin, S., Guilinger, J. P., Ma, E., Doudna, J. A., and Liu, D. R. (2013). High throughput profiling of off-target DNA cleavage reveals RNA-programmed Cas9 nuclease specificity. Nat Biotechnol 31, 839-843.

Pourcel, C., Salvignol, G., and Vergnaud, G. (2005). CRISPR elements in Yersinia pestis acquire new repeats by preferential uptake of bacteriophage DNA, and provide additional tools for evolutionary studies. Microbiology 151, 653-663.

Ran, F. A., Cong, L., Yan, W. X., Scott, D. A., Gootenberg, J. S., Kriz, A. J., Zetsche, B., Shalem, O., Wu, X., Makarova, K. S., et al. (2015). In vivo genome editing using Staphylococcus aureus Cas9. Nature 520, 186-191.

Rotman, E., and Seifert, H. S. (2014). The genetics of Neisseria species. Annu. Rev. Genet. 48, 405-431.

Sampson, T. R., Napier, B. A., Schroeder, M. R., Louwen, R., Zhao, J., Chin, C. Y., Ratner, H. K., Llewellyn, A. C., Jones, C. L., Laroui, H., et al. (2014). A CRISPR-Cas system enhances envelope integrity mediating antibiotic resistance and inflammasome evasion. Proc. Natl. Acad. Sci. USA 111, 11163-11168.

Sampson, T. R., Saroj, S. D., Llewellyn, A. C., Tzeng, Y. L., and Weiss, D. S. (2013). A CRISPR/Cas system mediates bacterial innate immune evasion and virulence. Nature 497, 254-257.

Sapranauskas, R., Gasiunas, G., Fremaux, C., Barrangou, R., Horvath, P., and Siksnys, V. (2011). The Streptococcus thermophilus CRISPR/Cas system provides immunity in Escherichia coli. Nucleic Acids Res. 39, 9275-9282.

Sontheimer, E. J., and Barrangou, R. (2015). The bacterial origins of the CRISPR genome editing revolution. Hum. Gene Ther. 26, 413-424.

Sternberg, S. H., Redding, S., Jinek, M., Greene, E. C., and Doudna, J. A. (2014). DNA interrogation by the CRISPR RNA-guided endonuclease Cas9. Nature 507, 62-67.

Tadokoro, T., and Kanaya, S. (2009). Ribonuclease H: molecular diversities, substrate binding domains, and catalytic mechanism of the prokaryotic enzymes. FEBS J. 276, 1482-1493.

Stols, L., Gu, M. Dieckman, L., Raffen, R., Collart, F. R., and Donnelly, M. I., (2002) A new vector for high-throughput, ligation-independent cloning encoding a tobacco etch virus protease cleavage site. Protein Expr. Purif. 25, 8-15.

van der Oost, J., Westra, E. R., Jackson, R. N., and Wiedenheft, B. (2014). Unravelling the structural and mechanistic basis of CRISPR-Cas systems. Nat. Rev. Microbiol. 12, 479-492.

Vercoe, R. B., Chang, J. T., Dy, R. L., Taylor, C., Gristwood, T., Clulow, J. S., Richter, C., Przybilski, R., Pitman, A. R., and Fineran, P. C. (2013). Cytotoxic chromosomal targeting by CRISPR/Cas systems can reshape bacterial genomes and expel or remodel pathogenicity islands. PLoS Genet. 9, e1003454.

Yosef, I., Goren, M. G., and Qimron, U. (2012). Proteins and DNA elements essential for the CRISPR adaptation process in Escherichia coli. Nucleic Acids Res. 40, 5569-5576. Zhang, Y., Ge, X., Yang, F., Zhang, L., Zheng, J., Tan, X., Jin, Z. B., Qu, J., and Gu, F. (2014). Comparison of non-canonical PAMs for CRISPR/Cas9-mediated DNA cleavage in human cells. Sci Rep 4, 5405.

Zhang, Y., Heidrich, N., Ampattu, B. J., Gunderson, C. W., Seifert, H. S., Schoen, C., Vogel, J., and Sontheimer, E. J. (2013). Processing-independent CRISPR RNAs limit natural transformation in Neisseria meningitidis. Mol. Cell 50, 488-503.

```
<160> NUMBER OF SEQ ID NOS: 165

<210> SEQ ID NO 1
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (7)..(8)
<223> OTHER INFORMATION: n is a, c, g, or t

<400> SEQUENCE: 1 nnnngann                                                                 8

<210> SEQ ID NO 2
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 2 nnnngttn                                                                 8

<210> SEQ ID NO 3
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: n is a, c, g, or t

<400> SEQUENCE: 3 nnnngatt                                                                 8

<210> SEQ ID NO 4
<211> LENGTH: 6
<212> TYPE: DNA
<213> ORGANISM: Artificial Sequence
<220> FEATURE:
<223> OTHER INFORMATION: Synthetic

<400> SEQUENCE: 4 ttaggg                                                                   6

<210> SEQ ID NO 5
<211> LENGTH: 5
<212> TYPE: DNA
<213> ORGANISM: Artificial Sequence
<220> FEATURE:
<223> OTHER INFORMATION: Synthetic

<400> SEQUENCE: 5
``` attcc                                                                                               5

<210> SEQ ID NO 6
<211> LENGTH: 3
<212> TYPE: DNA
<213> ORGANISM: Artificial Sequence
<220> FEATURE:
<223> OTHER INFORMATION: Synthetic

<400> SEQUENCE: 6 ctg                                                                                                 3

<210> SEQ ID NO 7
<211> LENGTH: 6
<212> TYPE: DNA
<213> ORGANISM: Artificial Sequence
<220> FEATURE:
<223> OTHER INFORMATION: Synthetic

<400> SEQUENCE: 7 ggggcc                                                                                              6

<210> SEQ ID NO 8
<211> LENGTH: 3
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is a, c, g, or t

<400> SEQUENCE: 8 ngg                                                                                                 3

<210> SEQ ID NO 9
<211> LENGTH: 3
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is a, c, g, or t

<400> SEQUENCE: 9 nag                                                                                                 3

<210> SEQ ID NO 10
<211> LENGTH: 3
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is a, c, g, or t

<400> SEQUENCE: 10 ngt                                                                                                 3

<210> SEQ ID NO 11
<211> LENGTH: 8
<212> TYPE: DNA
<213> ORGANISM: Artificial Sequence

```
<220> FEATURE:
<223> OTHER INFORMATION: Synthetic
<220> FEATURE:
<221> NAME/KEY: misc_feature
<222> LOCATION: (1)..(4)
<223> OTHER INFORMATION: n is a, c, g, or t

<400> SEQUENCE: 11 nnnngttt                                                                    8

<210> SEQ ID NO 12
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: n is a, c, g, or t

<400> SEQUENCE: 12 nnnngctt                                                                    8

<210> SEQ ID NO 13
<211> LENGTH: 7
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: n is a, c, g, or t

<400> SEQUENCE: 13 nnagaaw                                                                     7

<210> SEQ ID NO 14
<211> LENGTH: 7
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: n is a, c, g, or t

<400> SEQUENCE: 14 nnggaaw                                                                     7

<210> SEQ ID NO 15
<211> LENGTH: 7
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: n is a, c, g, or t

<400> SEQUENCE: 15 nnaggaw                                                                     7

<210> SEQ ID NO 16
<211> LENGTH: 7
<212> TYPE: DNA
```

```
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: n is a, c, g, or t

<400> SEQUENCE: 16 nnagggw                                                              7

<210> SEQ ID NO 17
<211> LENGTH: 4
<212> TYPE: DNA
<213> ORGANISM: Artificial Sequence
<220> FEATURE:
<223> OTHER INFORMATION: Synthetic

<400> SEQUENCE: 17 gatt                                                                 4

<210> SEQ ID NO 18
<211> LENGTH: 4
<212> TYPE: DNA
<213> ORGANISM: Artificial Sequence
<220> FEATURE:
<223> OTHER INFORMATION: Synthetic

<400> SEQUENCE: 18 gtat                                                                 4

<210> SEQ ID NO 19
<211> LENGTH: 4
<212> TYPE: DNA
<213> ORGANISM: Artificial Sequence
<220> FEATURE:
<223> OTHER INFORMATION: Synthetic

<400> SEQUENCE: 19 gctt                                                                 4

<210> SEQ ID NO 20
<211> LENGTH: 5
<212> TYPE: DNA
<213> ORGANISM: Artificial Sequence
<220> FEATURE:
<223> OTHER INFORMATION: Synthetic

<400> SEQUENCE: 20 gyaaa                                                                5

<210> SEQ ID NO 21
<211> LENGTH: 109
<212> TYPE: DNA
<213> ORGANISM: Artificial Sequence
<220> FEATURE:
<223> OTHER INFORMATION: Synthetic

<400> SEQUENCE: 21
taatacgact cactatagaa atgagaaccg ttgctacaat aaggccgtct gaaaagatgt    60
gccgcaacgc tctgccccct aaagcttctg ctttaagggg catcgttta              109

<210> SEQ ID NO 22
<211> LENGTH: 109
<212> TYPE: DNA
<213> ORGANISM: Artificial Sequence
```

```
<220> FEATURE:
<223> OTHER INFORMATION: Synthetic

<400> SEQUENCE: 22
taaacgatgc cccttaaagc agaagcttta aggggcagag cgttgcggca catcttttca    60
gacggcctta ttgtagcaac ggttctcatt tctatagtga gtcgtatta               109

<210> SEQ ID NO 23
<211> LENGTH: 65
<212> TYPE: DNA
<213> ORGANISM: Artificial Sequence
<220> FEATURE:
<223> OTHER INFORMATION: Synthetic

<400> SEQUENCE: 23
taatacgact cactataggg tgcgcggcgc attaccttta cgttgtagct ccctttctca    60
tttcg                                                                65

<210> SEQ ID NO 24
<211> LENGTH: 65
<212> TYPE: DNA
<213> ORGANISM: Artificial Sequence
<220> FEATURE:
<223> OTHER INFORMATION: Synthetic

<400> SEQUENCE: 24
cgaaatgaga aagggagcta caacgtaaag gtaatgcgcc gcgcacccta tagtgagtcg    60
tatta                                                                65

<210> SEQ ID NO 25
<211> LENGTH: 65
<212> TYPE: DNA
<213> ORGANISM: Artificial Sequence
<220> FEATURE:
<223> OTHER INFORMATION: Synthetic

<400> SEQUENCE: 25
taatacgact cactataggg tcctcagatt tagtattcag agttgtagct ccctttctca    60
tttcg                                                                65

<210> SEQ ID NO 26
<211> LENGTH: 65
<212> TYPE: DNA
<213> ORGANISM: Artificial Sequence
<220> FEATURE:
<223> OTHER INFORMATION: Synthetic

<400> SEQUENCE: 26
cgaaatgaga aagggagcta caactctgaa tactaaatct gaggacccta tagtgagtcg    60
tatta                                                                65

<210> SEQ ID NO 27
<211> LENGTH: 65
<212> TYPE: DNA
<213> ORGANISM: Artificial Sequence
<220> FEATURE:
<223> OTHER INFORMATION: Synthetic

<400> SEQUENCE: 27
taatacgact cactataggg tttcatggcg cgttcttgct ggttgtagct ccctttctca    60
tttcg                                                                65
```

<210> SEQ ID NO 28
<211> LENGTH: 65
<212> TYPE: DNA
<213> ORGANISM: Artificial Sequence
<220> FEATURE:
<223> OTHER INFORMATION: Synthetic

<400> SEQUENCE: 28
cgaaatgaga aagggagcta caaccagcaa gaacgcgcca tgaaaccta tagtgagtcg    60 tatta                                                                65

<210> SEQ ID NO 29
<211> LENGTH: 52
<212> TYPE: DNA
<213> ORGANISM: Artificial Sequence
<220> FEATURE:
<223> OTHER INFORMATION: Synthetic

<400> SEQUENCE: 29
taatacgact cactataggt gcgcggcgca ttacctttac gttgtagctc cc            52

<210> SEQ ID NO 30
<211> LENGTH: 53
<212> TYPE: DNA
<213> ORGANISM: Artificial Sequence
<220> FEATURE:
<223> OTHER INFORMATION: Synthetic

<400> SEQUENCE: 30
gggagctaca acgtaaaggt aatgcgccgc gcaccctata gtgagtcgta tta           53

<210> SEQ ID NO 31
<211> LENGTH: 49
<212> TYPE: DNA
<213> ORGANISM: Artificial Sequence
<220> FEATURE:
<223> OTHER INFORMATION: Synthetic

<400> SEQUENCE: 31
taatacgact cactataggg tgcgcggcgc attaccttta cgttgtagc                49

<210> SEQ ID NO 32
<211> LENGTH: 49
<212> TYPE: DNA
<213> ORGANISM: Artificial Sequence
<220> FEATURE:
<223> OTHER INFORMATION: Synthetic

<400> SEQUENCE: 32
gctacaacgt aaaggtaatg cgccgcgcac cctatagtga gtcgtatta                49

<210> SEQ ID NO 33
<211> LENGTH: 45
<212> TYPE: DNA
<213> ORGANISM: Artificial Sequence
<220> FEATURE:
<223> OTHER INFORMATION: Synthetic

<400> SEQUENCE: 33
taatacgact cactataggg tgcgcggcgc attaccttta cgttg                    45

<210> SEQ ID NO 34
<211> LENGTH: 45
<212> TYPE: DNA
<213> ORGANISM: Artificial Sequence
<220> FEATURE:
<223> OTHER INFORMATION: Synthetic

<400> SEQUENCE: 34
caacgtaaag gtaatgcgcc gcgcacccta tagtgagtcg tatta         45

<210> SEQ ID NO 35
<211> LENGTH: 41
<212> TYPE: DNA
<213> ORGANISM: Artificial Sequence
<220> FEATURE:
<223> OTHER INFORMATION: Synthetic

<400> SEQUENCE: 35
taatacgact cactataggg tgcgcggcgc attaccttta c            41

<210> SEQ ID NO 36
<211> LENGTH: 41
<212> TYPE: DNA
<213> ORGANISM: Artificial Sequence
<220> FEATURE:
<223> OTHER INFORMATION: Synthetic

<400> SEQUENCE: 36
gtaaaggtaa tgcgccgcgc accctatagt gagtcgtatt a            41

<210> SEQ ID NO 37
<211> LENGTH: 63
<212> TYPE: DNA
<213> ORGANISM: Artificial Sequence
<220> FEATURE:
<223> OTHER INFORMATION: Synthetic

<400> SEQUENCE: 37
taatacgact cactataggg tgcgcggcgc attaccttta cgttttagag ctatgctgtt    60
ttg                                                                 63

<210> SEQ ID NO 38
<211> LENGTH: 63
<212> TYPE: DNA
<213> ORGANISM: Artificial Sequence
<220> FEATURE:
<223> OTHER INFORMATION: Synthetic

<400> SEQUENCE: 38
caaaacagca tagctctaaa acgtaaaggt aatgcgccgc gcaccctata gtgagtcgta    60
tta                                                                 63

<210> SEQ ID NO 39
<211> LENGTH: 36
<212> TYPE: DNA
<213> ORGANISM: Artificial Sequence
<220> FEATURE:
<223> OTHER INFORMATION: Synthetic

<400> SEQUENCE: 39
taatacgact cactataggg tgcgcggcgc attacc                  36

<210> SEQ ID NO 40
<211> LENGTH: 36
<212> TYPE: DNA
<213> ORGANISM: Artificial Sequence
<220> FEATURE:
<223> OTHER INFORMATION: Synthetic

<400> SEQUENCE: 40
ggtaatgcgc cgcgcaccct atagtgagtc gtatta      36

<210> SEQ ID NO 41
<211> LENGTH: 38
<212> TYPE: DNA
<213> ORGANISM: Artificial Sequence
<220> FEATURE:
<223> OTHER INFORMATION: Synthetic

<400> SEQUENCE: 41
taatacgact cactataggg catgcgcggc gcattacc      38

<210> SEQ ID NO 42
<211> LENGTH: 38
<212> TYPE: DNA
<213> ORGANISM: Artificial Sequence
<220> FEATURE:
<223> OTHER INFORMATION: Synthetic

<400> SEQUENCE: 42
ggtaatgcgc cgcgcatgcc ctatagtgag tcgtatta      38

<210> SEQ ID NO 43
<211> LENGTH: 39
<212> TYPE: DNA
<213> ORGANISM: Artificial Sequence
<220> FEATURE:
<223> OTHER INFORMATION: Synthetic

<400> SEQUENCE: 43
taatacgact cactataggg gcatgcgcgg cgcattacc      39

<210> SEQ ID NO 44
<211> LENGTH: 39
<212> TYPE: DNA
<213> ORGANISM: Artificial Sequence
<220> FEATURE:
<223> OTHER INFORMATION: Synthetic

<400> SEQUENCE: 44
ggtaatgcgc cgcgcatgcc cctatagtga gtcgtatta      39

<210> SEQ ID NO 45
<211> LENGTH: 46
<212> TYPE: DNA
<213> ORGANISM: Artificial Sequence
<220> FEATURE:
<223> OTHER INFORMATION: Synthetic

<400> SEQUENCE: 45
taatacgact cactataggg ccgcatgcgc ggcgcattac ctttac      46

<210> SEQ ID NO 46
<211> LENGTH: 46
<212> TYPE: DNA
<213> ORGANISM: Artificial Sequence
<220> FEATURE:
<223> OTHER INFORMATION: Synthetic

<400> SEQUENCE: 46
gtaaaggtaa tgcgccgcgc atgcggccct atagtgagtc gtatta      46

<210> SEQ ID NO 47
<211> LENGTH: 51

<212> TYPE: DNA
<213> ORGANISM: Artificial Sequence
<220> FEATURE:
<223> OTHER INFORMATION: Synthetic

<400> SEQUENCE: 47
taatacgact cactataggg tgcgcggcgc attaccttta catatgatta t          51

<210> SEQ ID NO 48
<211> LENGTH: 51
<212> TYPE: DNA
<213> ORGANISM: Artificial Sequence
<220> FEATURE:
<223> OTHER INFORMATION: Synthetic

<400> SEQUENCE: 48
ataatcatat gtaaaggtaa tgcgccgcgc accctatagt gagtcgtatt a          51

<210> SEQ ID NO 49
<211> LENGTH: 86
<212> TYPE: DNA
<213> ORGANISM: Artificial Sequence
<220> FEATURE:
<223> OTHER INFORMATION: Synthetic

<400> SEQUENCE: 49
caagtctaat acgactcact atagggtcag cacggccagc aatccggcgt aaaggtaatg    60
cgccgcgcat gaggaataaa aatctg                                        86

<210> SEQ ID NO 50
<211> LENGTH: 86
<212> TYPE: DNA
<213> ORGANISM: Artificial Sequence
<220> FEATURE:
<223> OTHER INFORMATION: Synthetic

<400> SEQUENCE: 50 cagatttttta ttcctcatgc gcggcgcatt acctttacgc cggattgctg gccgtgctga   60
ccctatagtg agtcgtatta gacttg                                        86

<210> SEQ ID NO 51
<211> LENGTH: 59
<212> TYPE: DNA
<213> ORGANISM: Artificial Sequence
<220> FEATURE:
<223> OTHER INFORMATION: Synthetic

<400> SEQUENCE: 51
taatacgact cactataggt aatcggggat gtcggcggtt ttagagctat gctgttttg    59

<210> SEQ ID NO 52
<211> LENGTH: 59
<212> TYPE: DNA
<213> ORGANISM: Artificial Sequence
<220> FEATURE:
<223> OTHER INFORMATION: Synthetic

<400> SEQUENCE: 52
caaaacagca tagctctaaa accgccgaca tccccgatta cctatagtga gtcgtatta    59

<210> SEQ ID NO 53
<211> LENGTH: 59
<212> TYPE: DNA
<213> ORGANISM: Artificial Sequence
<220> FEATURE:

<223> OTHER INFORMATION: Synthetic

<400> SEQUENCE: 53
taatacgact cactataggg cgaggagctg ttcaccggtt ttagagctat gctgttttg    59

<210> SEQ ID NO 54
<211> LENGTH: 59
<212> TYPE: DNA
<213> ORGANISM: Artificial Sequence
<220> FEATURE:
<223> OTHER INFORMATION: Synthetic

<400> SEQUENCE: 54
caaaacagca tagctctaaa accggtgaac agctcctcgc cctatagtga gtcgtatta    59

<210> SEQ ID NO 55
<211> LENGTH: 37
<212> TYPE: DNA
<213> ORGANISM: Artificial Sequence
<220> FEATURE:
<223> OTHER INFORMATION: Synthetic

<400> SEQUENCE: 55
taatacgact cactataggt aatcggggat gtcggcg                            37

<210> SEQ ID NO 56
<211> LENGTH: 49
<212> TYPE: DNA
<213> ORGANISM: Artificial Sequence
<220> FEATURE:
<223> OTHER INFORMATION: Synthetic

<400> SEQUENCE: 56
taatacgact cactataggt caaaacagca tagcaagtta aaataaggc               49

<210> SEQ ID NO 57
<211> LENGTH: 25
<212> TYPE: DNA
<213> ORGANISM: Artificial Sequence
<220> FEATURE:
<223> OTHER INFORMATION: Synthetic

<400> SEQUENCE: 57
agcaccgact cggtgccact ttttc                                         25

<210> SEQ ID NO 58
<211> LENGTH: 60
<212> TYPE: DNA
<213> ORGANISM: Artificial Sequence
<220> FEATURE:
<223> OTHER INFORMATION: Synthetic

<400> SEQUENCE: 58
cagattttta ttcctcatgc gcggcgcatt acctttacgc cggattgctg gccgtgctga   60

<210> SEQ ID NO 59
<211> LENGTH: 60
<212> TYPE: DNA
<213> ORGANISM: Artificial Sequence
<220> FEATURE:
<223> OTHER INFORMATION: Synthetic

<400> SEQUENCE: 59
tcagcacggc cagcaatccg gcgtaaaggt aatgcgccgc gcatgaggaa taaaaatctg   60

```
<210> SEQ ID NO 60
<211> LENGTH: 60
<212> TYPE: DNA
<213> ORGANISM: Artificial Sequence
<220> FEATURE:
<223> OTHER INFORMATION: Synthetic

<400> SEQUENCE: 60
cagattttta ttcctcatgc gcggcgcatt acctttacgc cgctaagctg gccgtgctga      60

<210> SEQ ID NO 61
<211> LENGTH: 60
<212> TYPE: DNA
<213> ORGANISM: Artificial Sequence
<220> FEATURE:
<223> OTHER INFORMATION: Synthetic

<400> SEQUENCE: 61
tcagcacggc cagcttagcg gcgtaaaggt aatgcgccgc gcatgaggaa taaaaatctg      60

<210> SEQ ID NO 62
<211> LENGTH: 50
<212> TYPE: DNA
<213> ORGANISM: Artificial Sequence
<220> FEATURE:
<223> OTHER INFORMATION: Synthetic

<400> SEQUENCE: 62
attcagcacg gcatataatc atatgtaaag gtaatgcgcc gcgcatgcgg                 50

<210> SEQ ID NO 63
<211> LENGTH: 50
<212> TYPE: DNA
<213> ORGANISM: Artificial Sequence
<220> FEATURE:
<223> OTHER INFORMATION: Synthetic

<400> SEQUENCE: 63
attcagcacg gcatatatag atatgtaaag gtaatgcgcc gcgcatgcgg                 50

<210> SEQ ID NO 64
<211> LENGTH: 48
<212> TYPE: DNA
<213> ORGANISM: Artificial Sequence
<220> FEATURE:
<223> OTHER INFORMATION: Synthetic

<400> SEQUENCE: 64
tcatgcgcgg cgcattacct ttacgttgta gctccctttc tcatttcg                   48

<210> SEQ ID NO 65
<211> LENGTH: 64
<212> TYPE: DNA
<213> ORGANISM: Artificial Sequence
<220> FEATURE:
<223> OTHER INFORMATION: Synthetic

<400> SEQUENCE: 65
ccacctgctg aaggaatagt gcgcggcgca ttacctttac gttgtagctc cctttctcat      60
ttcg                                                                  64

<210> SEQ ID NO 66
<211> LENGTH: 40
<212> TYPE: DNA
<213> ORGANISM: Artificial Sequence
<220> FEATURE:
```

<223> OTHER INFORMATION: Synthetic

<400> SEQUENCE: 66
aagtttgaag gtgataccct tgttaataga atcgagttaa        40

<210> SEQ ID NO 67
<211> LENGTH: 60
<212> TYPE: DNA
<213> ORGANISM: Artificial Sequence
<220> FEATURE:
<223> OTHER INFORMATION: Synthetic

<400> SEQUENCE: 67 cagatttttta ttcctcatgc gcggcgcatt acctttacat atatgattgc tggccgtgct        60

<210> SEQ ID NO 68
<211> LENGTH: 60
<212> TYPE: DNA
<213> ORGANISM: Artificial Sequence
<220> FEATURE:
<223> OTHER INFORMATION: Synthetic

<400> SEQUENCE: 68
agcacggcca gcaatcatat atgtaaaggt aatgcgccgc gcatgaggaa taaaaatctg        60

<210> SEQ ID NO 69
<211> LENGTH: 60
<212> TYPE: DNA
<213> ORGANISM: Artificial Sequence
<220> FEATURE:
<223> OTHER INFORMATION: Synthetic

<400> SEQUENCE: 69 cagatttttta ttcctcatgc gcggcgcatt acctttacat atagattgct ggccgtgctg        60

<210> SEQ ID NO 70
<211> LENGTH: 60
<212> TYPE: DNA
<213> ORGANISM: Artificial Sequence
<220> FEATURE:
<223> OTHER INFORMATION: Synthetic

<400> SEQUENCE: 70
cagcacggcc agcaatctat atgtaaaggt aatgcgccgc gcatgaggaa taaaaatctg        60

<210> SEQ ID NO 71
<211> LENGTH: 60
<212> TYPE: DNA
<213> ORGANISM: Artificial Sequence
<220> FEATURE:
<223> OTHER INFORMATION: Synthetic

<400> SEQUENCE: 71 cagatttttta ttcctcatgc gcggcgcatt acctttacat atgattgctg gccgtgctga        60

<210> SEQ ID NO 72
<211> LENGTH: 60
<212> TYPE: DNA
<213> ORGANISM: Artificial Sequence
<220> FEATURE:
<223> OTHER INFORMATION: Synthetic

<400> SEQUENCE: 72
tcagcacggc cagcaatcat atgtaaaggt aatgcgccgc gcatgaggaa taaaaatctg        60

<210> SEQ ID NO 73
<211> LENGTH: 60
<212> TYPE: DNA
<213> ORGANISM: Artificial Sequence
<220> FEATURE:
<223> OTHER INFORMATION: Synthetic

<400> SEQUENCE: 73 cagatttta ttcctcatgc gcggcgcatt acctttacat agattgctgg ccgtgctgaa    60

<210> SEQ ID NO 74
<211> LENGTH: 60
<212> TYPE: DNA
<213> ORGANISM: Artificial Sequence
<220> FEATURE:
<223> OTHER INFORMATION: Synthetic

<400> SEQUENCE: 74
ttcagcacgg ccagcaatct atgtaaaggt aatgcgccgc gcatgaggaa taaaaatctg    60

<210> SEQ ID NO 75
<211> LENGTH: 60
<212> TYPE: DNA
<213> ORGANISM: Artificial Sequence
<220> FEATURE:
<223> OTHER INFORMATION: Synthetic

<400> SEQUENCE: 75 cagatttta ttcctcatgc gcggcgcatt acctttacat gattgctggc cgtgctgaag    60

<210> SEQ ID NO 76
<211> LENGTH: 60
<212> TYPE: DNA
<213> ORGANISM: Artificial Sequence
<220> FEATURE:
<223> OTHER INFORMATION: Synthetic

<400> SEQUENCE: 76
cttcagcacg gccagcaatc atgtaaaggt aatgcgccgc gcatgaggaa taaaaatctg    60

<210> SEQ ID NO 77
<211> LENGTH: 42
<212> TYPE: DNA
<213> ORGANISM: Artificial Sequence
<220> FEATURE:
<223> OTHER INFORMATION: Synthetic

<400> SEQUENCE: 77
ccaaggcgta cgtgaagcac cccgccgaca tccccgatta cc                      42

<210> SEQ ID NO 78
<211> LENGTH: 37
<212> TYPE: DNA
<213> ORGANISM: Artificial Sequence
<220> FEATURE:
<223> OTHER INFORMATION: Synthetic

<400> SEQUENCE: 78 cagatttta ttcctcatgc gcggcgcatt acctta                              37

<210> SEQ ID NO 79
<211> LENGTH: 36
<212> TYPE: DNA
<213> ORGANISM: Artificial Sequence
<220> FEATURE:
<223> OTHER INFORMATION: Synthetic

<400> SEQUENCE: 79
cagattttta ttcctcatgc gcggcgcatt accttt                36

<210> SEQ ID NO 80
<211> LENGTH: 35
<212> TYPE: DNA
<213> ORGANISM: Artificial Sequence
<220> FEATURE:
<223> OTHER INFORMATION: Synthetic

<400> SEQUENCE: 80
cagattttta ttcctcatgc gcggcgcatt acctt                 35

<210> SEQ ID NO 81
<211> LENGTH: 34
<212> TYPE: DNA
<213> ORGANISM: Artificial Sequence
<220> FEATURE:
<223> OTHER INFORMATION: Synthetic

<400> SEQUENCE: 81
cagattttta ttcctcatgc gcggcgcatt acct                  34

<210> SEQ ID NO 82
<211> LENGTH: 34
<212> TYPE: DNA
<213> ORGANISM: Artificial Sequence
<220> FEATURE:
<223> OTHER INFORMATION: Synthetic

<400> SEQUENCE: 82
cagattttta ttcctcatgc gcggcgcatt acct                  34

<210> SEQ ID NO 83
<211> LENGTH: 25
<212> TYPE: DNA
<213> ORGANISM: Artificial Sequence
<220> FEATURE:
<223> OTHER INFORMATION: Synthetic

<400> SEQUENCE: 83
tcagcacggc cagcaatccg gcgta                            25

<210> SEQ ID NO 84
<211> LENGTH: 24
<212> TYPE: DNA
<213> ORGANISM: Artificial Sequence
<220> FEATURE:
<223> OTHER INFORMATION: Synthetic

<400> SEQUENCE: 84
tcagcacggc cagcaatccg gcgt                             24

<210> SEQ ID NO 85
<211> LENGTH: 22
<212> TYPE: DNA
<213> ORGANISM: Artificial Sequence
<220> FEATURE:
<223> OTHER INFORMATION: Synthetic

<400> SEQUENCE: 85
tcagcacggc cagcaatccg gc                               22

<210> SEQ ID NO 86
<211> LENGTH: 24

<212> TYPE: DNA
<213> ORGANISM: Artificial Sequence
<220> FEATURE:
<223> OTHER INFORMATION: Synthetic

<400> SEQUENCE: 86
gcctgcatta ggcttgtttc atag                                          24

<210> SEQ ID NO 87
<211> LENGTH: 39
<212> TYPE: DNA
<213> ORGANISM: Artificial Sequence
<220> FEATURE:
<223> OTHER INFORMATION: Synthetic

<400> SEQUENCE: 87
actagtatag tcgacacttc gacgggaaat ccttatttc                          39

<210> SEQ ID NO 88
<211> LENGTH: 36
<212> TYPE: DNA
<213> ORGANISM: Artificial Sequence
<220> FEATURE:
<223> OTHER INFORMATION: Synthetic

<400> SEQUENCE: 88
gtcgactata ctagtcagcc gttgcgataa gcgaac                             36

<210> SEQ ID NO 89
<211> LENGTH: 24
<212> TYPE: DNA
<213> ORGANISM: Artificial Sequence
<220> FEATURE:
<223> OTHER INFORMATION: Synthetic

<400> SEQUENCE: 89
tggtgcaatt tctgtgttgg acgg                                          24

<210> SEQ ID NO 90

<400> SEQUENCE: 90

000

<210> SEQ ID NO 91
<211> LENGTH: 48
<212> TYPE: DNA
<213> ORGANISM: Artificial Sequence
<220> FEATURE:
<223> OTHER INFORMATION: Synthetic

<400> SEQUENCE: 91
gtaaaggtaa tgcgccgcgc atgagtttgg gattctagcc gttgtgag                48

<210> SEQ ID NO 92
<211> LENGTH: 49
<212> TYPE: DNA
<213> ORGANISM: Artificial Sequence
<220> FEATURE:
<223> OTHER INFORMATION: Synthetic

<400> SEQUENCE: 92
tcatgcgcgg cgcattacct ttacgttgta gctcccttc tcatttcgg                49

<210> SEQ ID NO 93
<211> LENGTH: 38

<212> TYPE: DNA
<213> ORGANISM: Artificial Sequence
<220> FEATURE:
<223> OTHER INFORMATION: Synthetic

<400> SEQUENCE: 93
tcgcttaatt aataaacgat gccccttaaa gcagaagc                    38

<210> SEQ ID NO 94
<211> LENGTH: 35
<212> TYPE: DNA
<213> ORGANISM: Artificial Sequence
<220> FEATURE:
<223> OTHER INFORMATION: Synthetic

<400> SEQUENCE: 94
tcgcttaatt aaaagcttta aggggcagag cgttg                       35

<210> SEQ ID NO 95
<211> LENGTH: 34
<212> TYPE: DNA
<213> ORGANISM: Artificial Sequence
<220> FEATURE:
<223> OTHER INFORMATION: Synthetic

<400> SEQUENCE: 95
tcgcttaatt aacggcacat cttttcagac ggcc                        34

<210> SEQ ID NO 96
<211> LENGTH: 35
<212> TYPE: DNA
<213> ORGANISM: Artificial Sequence
<220> FEATURE:
<223> OTHER INFORMATION: Synthetic

<400> SEQUENCE: 96
tcgcttaatt aatcagacgg ccttattgta gcaac                       35

<210> SEQ ID NO 97
<211> LENGTH: 35
<212> TYPE: DNA
<213> ORGANISM: Artificial Sequence
<220> FEATURE:
<223> OTHER INFORMATION: Synthetic

<400> SEQUENCE: 97
tcgcttaatt aaattgtagc aacggttctc atttc                       35

<210> SEQ ID NO 98
<211> LENGTH: 36
<212> TYPE: DNA
<213> ORGANISM: Artificial Sequence
<220> FEATURE:
<223> OTHER INFORMATION: Synthetic

<400> SEQUENCE: 98
tcgcttaatt aataaagcag aagctttaag gggcag                      36

<210> SEQ ID NO 99
<211> LENGTH: 25
<212> TYPE: DNA
<213> ORGANISM: Artificial Sequence
<220> FEATURE:
<223> OTHER INFORMATION: Synthetic

<400> SEQUENCE: 99
agcttctgct ttaaggggca ttaat    25

<210> SEQ ID NO 100
<211> LENGTH: 19
<212> TYPE: DNA
<213> ORGANISM: Artificial Sequence
<220> FEATURE:
<223> OTHER INFORMATION: Synthetic

<400> SEQUENCE: 100
taatgcccct taaagcaga    19

<210> SEQ ID NO 101
<211> LENGTH: 26
<212> TYPE: DNA
<213> ORGANISM: Artificial Sequence
<220> FEATURE:
<223> OTHER INFORMATION: Synthetic

<400> SEQUENCE: 101
gggagctaca acgtaaaggt aatgcg    26

<210> SEQ ID NO 102
<211> LENGTH: 42
<212> TYPE: DNA
<213> ORGANISM: Artificial Sequence
<220> FEATURE:
<223> OTHER INFORMATION: Synthetic

<400> SEQUENCE: 102
cctttacgtt gtagctcccc gttgctacaa taaggccgtc tg    42

<210> SEQ ID NO 103
<211> LENGTH: 23
<212> TYPE: DNA
<213> ORGANISM: Artificial Sequence
<220> FEATURE:
<223> OTHER INFORMATION: Synthetic

<400> SEQUENCE: 103
attgtagcaa cggttctcat ttc    23

<210> SEQ ID NO 104
<211> LENGTH: 44
<212> TYPE: DNA
<213> ORGANISM: Artificial Sequence
<220> FEATURE:
<223> OTHER INFORMATION: Synthetic

<400> SEQUENCE: 104
atgagaaccg ttgctacaat caacgctctg ccccttaaag cttc    44

<210> SEQ ID NO 105
<211> LENGTH: 30
<212> TYPE: DNA
<213> ORGANISM: Artificial Sequence
<220> FEATURE:
<223> OTHER INFORMATION: Synthetic

<400> SEQUENCE: 105
tttcgggagc tacaacgtaa aggtaatgcg    30

<210> SEQ ID NO 106
<211> LENGTH: 46
<212> TYPE: DNA
<213> ORGANISM: Artificial Sequence
<220> FEATURE:
<223> OTHER INFORMATION: Synthetic

<400> SEQUENCE: 106
cctttacgtt gtagctcccg aaacgttgct acaataaggc cgtctg       46

<210> SEQ ID NO 107
<211> LENGTH: 35
<212> TYPE: DNA
<213> ORGANISM: Artificial Sequence
<220> FEATURE:
<223> OTHER INFORMATION: Synthetic

<400> SEQUENCE: 107
tacttccaat ccaatgccat ggctgccttc aaacc       35

<210> SEQ ID NO 108
<211> LENGTH: 33
<212> TYPE: DNA
<213> ORGANISM: Artificial Sequence
<220> FEATURE:
<223> OTHER INFORMATION: Synthetic

<400> SEQUENCE: 108
ttatccactt ccaatgtttt aacggacagg cgg       33

<210> SEQ ID NO 109
<211> LENGTH: 29
<212> TYPE: DNA
<213> ORGANISM: Artificial Sequence
<220> FEATURE:
<223> OTHER INFORMATION: Synthetic

<400> SEQUENCE: 109
gctcgaattc cgatcatatt caataaccc       29

<210> SEQ ID NO 110
<211> LENGTH: 29
<212> TYPE: DNA
<213> ORGANISM: Artificial Sequence
<220> FEATURE:
<223> OTHER INFORMATION: Synthetic

<400> SEQUENCE: 110
agaaccatcc gttctgctct atacctcg       29

<210> SEQ ID NO 111
<211> LENGTH: 40
<212> TYPE: DNA
<213> ORGANISM: Artificial Sequence
<220> FEATURE:
<223> OTHER INFORMATION: Synthetic

<400> SEQUENCE: 111
tcatgacatc ctcagattta gtattcagaa tatgatttta       40

<210> SEQ ID NO 112
<211> LENGTH: 40
<212> TYPE: DNA
<213> ORGANISM: Artificial Sequence
<220> FEATURE:
<223> OTHER INFORMATION: Synthetic

<400> SEQUENCE: 112
taaaatcata ttctgaatac taaatctgag gatgtcatga       40

<210> SEQ ID NO 113
<211> LENGTH: 48
<212> TYPE: DNA
<213> ORGANISM: Artificial Sequence
<220> FEATURE:
<223> OTHER INFORMATION: Synthetic

<400> SEQUENCE: 113
ggguccucag auuuaguauu cagaguugua gcucccuuuc ucauuucg            48

<210> SEQ ID NO 114
<211> LENGTH: 91
<212> TYPE: DNA
<213> ORGANISM: Artificial Sequence
<220> FEATURE:
<223> OTHER INFORMATION: Synthetic

<400> SEQUENCE: 114
aaaugagaac cguugcuaca auaaggccgu cugaaaagau gugccgcaac gcucugcccc    60
uuaaagcuuc ugcuuuaagg ggcaucguuu a                                  91

<210> SEQ ID NO 115
<211> LENGTH: 14
<212> TYPE: DNA
<213> ORGANISM: Artificial Sequence
<220> FEATURE:
<223> OTHER INFORMATION: Synthetic

<400> SEQUENCE: 115
cagatttagt attc            14

<210> SEQ ID NO 116
<211> LENGTH: 15
<212> TYPE: DNA
<213> ORGANISM: Artificial Sequence
<220> FEATURE:
<223> OTHER INFORMATION: Synthetic

<400> SEQUENCE: 116
ttaaaatcat attct            15

<210> SEQ ID NO 117
<211> LENGTH: 60
<212> TYPE: DNA
<213> ORGANISM: Artificial Sequence
<220> FEATURE:
<223> OTHER INFORMATION: Synthetic

<400> SEQUENCE: 117 cagatttta ttcctcatgc gcggcgcatt acctttacgc cggattgctg gccgtgctga    60

<210> SEQ ID NO 118
<211> LENGTH: 60
<212> TYPE: DNA
<213> ORGANISM: Artificial Sequence
<220> FEATURE:
<223> OTHER INFORMATION: Synthetic

<400> SEQUENCE: 118
tcagcacggc cagcaatccg gcgtaaaggt aatgcgccgc gcatgaggaa taaaaatctg    60

<210> SEQ ID NO 119
<211> LENGTH: 48
<212> TYPE: DNA
<213> ORGANISM: Artificial Sequence -continued
<220> FEATURE:
<223> OTHER INFORMATION: Synthetic

<400> SEQUENCE: 119
gggugcgcgg cgcauuaccu uuacguugua gcucccuuuc ucauuucg          48

<210> SEQ ID NO 120
<211> LENGTH: 11
<212> TYPE: DNA
<213> ORGANISM: Artificial Sequence
<220> FEATURE:
<223> OTHER INFORMATION: Synthetic

<400> SEQUENCE: 120 atatgattt a                                                   11

<210> SEQ ID NO 121
<211> LENGTH: 11
<212> TYPE: DNA
<213> ORGANISM: Artificial Sequence
<220> FEATURE:
<223> OTHER INFORMATION: Synthetic

<400> SEQUENCE: 121
taaaatcata t                                                  11

<210> SEQ ID NO 122
<211> LENGTH: 10
<212> TYPE: DNA
<213> ORGANISM: Artificial Sequence
<220> FEATURE:
<223> OTHER INFORMATION: Synthetic

<400> SEQUENCE: 122
gccggattgc                                                    10

<210> SEQ ID NO 123
<211> LENGTH: 10
<212> TYPE: DNA
<213> ORGANISM: Artificial Sequence
<220> FEATURE:
<223> OTHER INFORMATION: Synthetic

<400> SEQUENCE: 123
gcaatccggc                                                    10

<210> SEQ ID NO 124
<211> LENGTH: 12
<212> TYPE: DNA
<213> ORGANISM: Artificial Sequence
<220> FEATURE:
<223> OTHER INFORMATION: Synthetic

<400> SEQUENCE: 124
atataatcat at                                                 12

<210> SEQ ID NO 125
<211> LENGTH: 12
<212> TYPE: DNA
<213> ORGANISM: Artificial Sequence
<220> FEATURE:
<223> OTHER INFORMATION: Synthetic

<400> SEQUENCE: 125
atatatagat at                                                 12

```
<210> SEQ ID NO 126
<211> LENGTH: 38
<212> TYPE: DNA
<213> ORGANISM: Artificial Sequence
<220> FEATURE:
<223> OTHER INFORMATION: Synthetic

<400> SEQUENCE: 126
atggtcgtcg cgcaacaaaa ccccgctact cggcgatt                               38

<210> SEQ ID NO 127
<211> LENGTH: 38
<212> TYPE: DNA
<213> ORGANISM: Artificial Sequence
<220> FEATURE:
<223> OTHER INFORMATION: Synthetic

<400> SEQUENCE: 127
aatcgccgag tagcggggtt ttgttgcgcg acgaccat                               38

<210> SEQ ID NO 128
<211> LENGTH: 48
<212> TYPE: DNA
<213> ORGANISM: Artificial Sequence
<220> FEATURE:
<223> OTHER INFORMATION: Synthetic

<400> SEQUENCE: 128
ggggcgcaac aaaaccccgc tactguugua gcucccuuuc ucauuucg                    48

<210> SEQ ID NO 129
<211> LENGTH: 32
<212> TYPE: DNA
<213> ORGANISM: Artificial Sequence
<220> FEATURE:
<223> OTHER INFORMATION: Synthetic

<400> SEQUENCE: 129
acatcctcag atttagtatt cagaatatga tt                                     32

<210> SEQ ID NO 130
<211> LENGTH: 32
<212> TYPE: DNA
<213> ORGANISM: Artificial Sequence
<220> FEATURE:
<223> OTHER INFORMATION: Synthetic

<400> SEQUENCE: 130
aatcatattc tgaatactaa atctgaggat gt                                     32

<210> SEQ ID NO 131
<211> LENGTH: 28
<212> TYPE: DNA
<213> ORGANISM: Artificial Sequence
<220> FEATURE:
<223> OTHER INFORMATION: Synthetic

<400> SEQUENCE: 131
ggguccucag auuuaguauu cagaguug                                          28

<210> SEQ ID NO 132
<211> LENGTH: 16
<212> TYPE: DNA
<213> ORGANISM: Artificial Sequence
<220> FEATURE:
<223> OTHER INFORMATION: Synthetic
```

<400> SEQUENCE: 132
agatatagta ttcaga                                                        16

<210> SEQ ID NO 133
<211> LENGTH: 16
<212> TYPE: DNA
<213> ORGANISM: Artificial Sequence
<220> FEATURE:
<223> OTHER INFORMATION: Synthetic

<400> SEQUENCE: 133
agatttacta ttcaga                                                        16

<210> SEQ ID NO 134
<211> LENGTH: 16
<212> TYPE: DNA
<213> ORGANISM: Artificial Sequence
<220> FEATURE:
<223> OTHER INFORMATION: Synthetic

<400> SEQUENCE: 134
agatttagta tacaga                                                        16

<210> SEQ ID NO 135
<211> LENGTH: 16
<212> TYPE: DNA
<213> ORGANISM: Artificial Sequence
<220> FEATURE:
<223> OTHER INFORMATION: Synthetic

<400> SEQUENCE: 135
agatttagta ttcagt                                                        16

<210> SEQ ID NO 136
<211> LENGTH: 16
<212> TYPE: DNA
<213> ORGANISM: Artificial Sequence
<220> FEATURE:
<223> OTHER INFORMATION: Synthetic

<400> SEQUENCE: 136
tcatttagta ttcaga                                                        16

<210> SEQ ID NO 137
<211> LENGTH: 16
<212> TYPE: DNA
<213> ORGANISM: Artificial Sequence
<220> FEATURE:
<223> OTHER INFORMATION: Synthetic

<400> SEQUENCE: 137
agattatgta ttcaga                                                        16

<210> SEQ ID NO 138
<211> LENGTH: 16
<212> TYPE: DNA
<213> ORGANISM: Artificial Sequence
<220> FEATURE:
<223> OTHER INFORMATION: Synthetic

<400> SEQUENCE: 138
agatttagta aacaga                                                        16

<210> SEQ ID NO 139

```
<211> LENGTH: 16
<212> TYPE: DNA
<213> ORGANISM: Artificial Sequence
<220> FEATURE:
<223> OTHER INFORMATION: Synthetic

<400> SEQUENCE: 139
agatttagta ttcact                                                    16

<210> SEQ ID NO 140
<211> LENGTH: 36
<212> TYPE: DNA
<213> ORGANISM: Artificial Sequence
<220> FEATURE:
<223> OTHER INFORMATION: Synthetic

<400> SEQUENCE: 140
ttcctcatgc gcggcgcatt acctttacgc cggatt                              36

<210> SEQ ID NO 141
<211> LENGTH: 36
<212> TYPE: DNA
<213> ORGANISM: Artificial Sequence
<220> FEATURE:
<223> OTHER INFORMATION: Synthetic

<400> SEQUENCE: 141
aatccggcgt aaaggtaatg cgccgcgcat gaggaa                              36

<210> SEQ ID NO 142
<211> LENGTH: 28
<212> TYPE: DNA
<213> ORGANISM: Artificial Sequence
<220> FEATURE:
<223> OTHER INFORMATION: Synthetic

<400> SEQUENCE: 142
gggugcgcgg cgcauuaccu uuacguug                                       28

<210> SEQ ID NO 143
<211> LENGTH: 16
<212> TYPE: DNA
<213> ORGANISM: Artificial Sequence
<220> FEATURE:
<223> OTHER INFORMATION: Synthetic

<400> SEQUENCE: 143
ggcggattac ctttac                                                    16

<210> SEQ ID NO 144
<211> LENGTH: 16
<212> TYPE: DNA
<213> ORGANISM: Artificial Sequence
<220> FEATURE:
<223> OTHER INFORMATION: Synthetic

<400> SEQUENCE: 144
cgcgcataac ctttac                                                    16

<210> SEQ ID NO 145
<211> LENGTH: 16
<212> TYPE: DNA
<213> ORGANISM: Artificial Sequence
<220> FEATURE:
<223> OTHER INFORMATION: Synthetic

<400> SEQUENCE: 145
```

```
ggcgcattac cattac                                             16

<210> SEQ ID NO 146
<211> LENGTH: 16
<212> TYPE: DNA
<213> ORGANISM: Artificial Sequence
<220> FEATURE:
<223> OTHER INFORMATION: Synthetic

<400> SEQUENCE: 146
ggcgcattac ctttag                                             16

<210> SEQ ID NO 147
<211> LENGTH: 16
<212> TYPE: DNA
<213> ORGANISM: Artificial Sequence
<220> FEATURE:
<223> OTHER INFORMATION: Synthetic

<400> SEQUENCE: 147
cccgcattac ctttac                                             16

<210> SEQ ID NO 148
<211> LENGTH: 16
<212> TYPE: DNA
<213> ORGANISM: Artificial Sequence
<220> FEATURE:
<223> OTHER INFORMATION: Synthetic

<400> SEQUENCE: 148
ggcgctatac ctttac                                             16

<210> SEQ ID NO 149
<211> LENGTH: 16
<212> TYPE: DNA
<213> ORGANISM: Artificial Sequence
<220> FEATURE:
<223> OTHER INFORMATION: Synthetic

<400> SEQUENCE: 149
ggcgcattac gattac                                             16

<210> SEQ ID NO 150
<211> LENGTH: 16
<212> TYPE: DNA
<213> ORGANISM: Artificial Sequence
<220> FEATURE:
<223> OTHER INFORMATION: Synthetic

<400> SEQUENCE: 150
ggcgcattac cttttg                                             16

<210> SEQ ID NO 151
<211> LENGTH: 145
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(24)
<223> OTHER INFORMATION: n is a, c, g, t or u

<400> SEQUENCE: 151
nnnnnnnnnn nnnnnnnnnn nnnnguugua gcucccuuuc ucauuucgga aacgaaauga     60
```

```
gaaccguugc uacaauaagg ccgucugaaa agaugugccg caacgcucug ccccuuaaag    120
cuucugcuuu aagggcauc guuua                                          145
```

<210> SEQ ID NO 152
<211> LENGTH: 26
<212> TYPE: DNA
<213> ORGANISM: Artificial Sequence
<220> FEATURE:
<223> OTHER INFORMATION: Synthetic

<400> SEQUENCE: 152

```
caagtgatac gccattacta tgccat                                         26
```

<210> SEQ ID NO 153
<211> LENGTH: 35
<212> TYPE: DNA
<213> ORGANISM: Artificial Sequence
<220> FEATURE:
<223> OTHER INFORMATION: Synthetic

<400> SEQUENCE: 153

```
tacctatggc atagtaatgg cgtatcactt ggact                               35
```

<210> SEQ ID NO 154
<211> LENGTH: 35
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (31)..(31)
<223> OTHER INFORMATION: n is a, c, g, or t

<400> SEQUENCE: 154

```
agtccaagtg atacgccatt actatgccat nggta                               35
```

<210> SEQ ID NO 155
<211> LENGTH: 16
<212> TYPE: DNA
<213> ORGANISM: Artificial Sequence
<220> FEATURE:
<223> OTHER INFORMATION: Synthetic

<400> SEQUENCE: 155

```
ttagggttag ggttag                                                    16
```

<210> SEQ ID NO 156
<211> LENGTH: 28
<212> TYPE: DNA
<213> ORGANISM: Artificial Sequence
<220> FEATURE:
<223> OTHER INFORMATION: Synthetic

<400> SEQUENCE: 156

```
ctaaccctaa ccctaaccct aaccctaa                                       28
```

<210> SEQ ID NO 157
<211> LENGTH: 99
<212> TYPE: RNA
<213> ORGANISM: Artificial Sequence
<220> FEATURE:
<223> OTHER INFORMATION: Synthetic

<400> SEQUENCE: 157

```
guuaggguua ggguuagggu uguuugagag cuagaaaaua gcaagucaaa uaaggcuagu    60
```
ccguuaucaa cuugaaaaag uggcaccgag ucggugcuu                                99

<210> SEQ ID NO 158
<211> LENGTH: 11
<212> TYPE: DNA
<213> ORGANISM: Artificial Sequence
<220> FEATURE:
<223> OTHER INFORMATION: Synthetic

<400> SEQUENCE: 158
ttgctgagat t                                                              11

<210> SEQ ID NO 159
<211> LENGTH: 12
<212> TYPE: DNA
<213> ORGANISM: Artificial Sequence
<220> FEATURE:
<223> OTHER INFORMATION: Synthetic

<400> SEQUENCE: 159
ttgctgatga tt                                                             12

<210> SEQ ID NO 160
<211> LENGTH: 13
<212> TYPE: DNA
<213> ORGANISM: Artificial Sequence
<220> FEATURE:
<223> OTHER INFORMATION: Synthetic

<400> SEQUENCE: 160
ttgctgatag att                                                            13

<210> SEQ ID NO 161
<211> LENGTH: 14
<212> TYPE: DNA
<213> ORGANISM: Artificial Sequence
<220> FEATURE:
<223> OTHER INFORMATION: Synthetic

<400> SEQUENCE: 161
ttgctgatat gatt                                                           14

<210> SEQ ID NO 162
<211> LENGTH: 15
<212> TYPE: DNA
<213> ORGANISM: Artificial Sequence
<220> FEATURE:
<223> OTHER INFORMATION: Synthetic

<400> SEQUENCE: 162
ttgctgatat agatt                                                          15

<210> SEQ ID NO 163
<211> LENGTH: 16
<212> TYPE: DNA
<213> ORGANISM: Artificial Sequence
<220> FEATURE:
<223> OTHER INFORMATION: Synthetic

<400> SEQUENCE: 163
ttgctgatat atgatt                                                         16

<210> SEQ ID NO 164
<211> LENGTH: 17
<212> TYPE: DNA

```
<213> ORGANISM: Artificial Sequence
<220> FEATURE:
<223> OTHER INFORMATION: Synthetic

<400> SEQUENCE: 164
ttgctgatat atagatt                                                17

<210> SEQ ID NO 165
<211> LENGTH: 18
<212> TYPE: DNA
<213> ORGANISM: Artificial Sequence
<220> FEATURE:
<223> OTHER INFORMATION: Synthetic

<400> SEQUENCE: 165
ttgctgatat atatgatt                                               18
```

We claim:

1. A composition comprising a *Neisseria meningitidis* Cas9 (NmeCas9) enzyme and a guide RNA (gRNA) sequence, wherein said gRNA lacks a transactivating CRISPR RNA (tracrRNA) sequence.

2. The composition of claim 1, wherein said gRNA sequence comprises a CRISPR RNA (crRNA) sequence.

3. The composition of claim 1, wherein said composition further comprises a single stranded deoxyribonucleic acid (ssDNA) sequence.

4. The composition of claim 1, wherein said composition does not comprise a double stranded deoxyribonucleic acid (dsDNA) sequence.

5. The composition of claim 3, wherein said ssDNA sequence comprises a protospacer adjacent motif (PAM).

6. The composition of claim 2, wherein said crRNA sequence comprises at least one complementary region to said PAM.

7. The composition of claim 3, wherein said ssDNA sequence lacks a PAM.

8. The composition of claim 3, wherein said crRNA sequence comprises at least one complementary sequence to said ssDNA.

9. The composition of claim 1, wherein said gRNA sequence is seventeen nucleotides.

10. The composition of claim 1, wherein said NmeCas9 protein comprises intact HNH domain.

11. The composition of claim 2, wherein said crRNA sequence comprises a mutated CRISPR repeat region.

12. The composition of claim 2, wherein said crRNA sequence does not have a CRISPR repeat region.

13. The composition of claim 5, wherein said ssDNA comprises a linker sequence adjacent to said PAM.

14. The composition of claim 13, wherein said linker sequence is approximately 2-6 nucleotides.

15. The composition of claim 13, wherein said linker sequence is 4 nucleotides.

* * * * *